United States Patent
Ganjam

(10) Patent No.: US 10,892,034 B2
(45) Date of Patent: Jan. 12, 2021

(54) USE OF HOMOLOGY DIRECT REPAIR TO RECORD TIMING OF A MOLECULAR EVENT

(71) Applicant: Microsoft Technology Licensing, LLC, Redmond, WA (US)

(72) Inventor: Kris K. Ganjam, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 115 days.

(21) Appl. No.: 15/625,998

(22) Filed: Jun. 16, 2017

(65) Prior Publication Data

US 2018/0004890 A1   Jan. 4, 2018

Related U.S. Application Data

(60) Provisional application No. 62/357,828, filed on Jul. 1, 2016, provisional application No. 62/399,190, filed on Sep. 23, 2016, provisional application No. 62/487,671, filed on Apr. 20, 2017.

(51) Int. Cl.

| | | |
|---|---|---|
| *G16B 25/00* | (2019.01) | |
| *G16B 40/00* | (2019.01) | |
| *G16B 99/00* | (2019.01) | |
| *C12N 15/90* | (2006.01) | |
| *C12N 15/10* | (2006.01) | |
| *C12Q 1/6816* | (2018.01) | |
| *C12N 15/11* | (2006.01) | |
| *G06N 5/02* | (2006.01) | |

(52) U.S. Cl.
CPC ........... *G16B 25/00* (2019.02); *C12N 15/102* (2013.01); *C12N 15/111* (2013.01); *C12N 15/90* (2013.01); *C12N 15/902* (2013.01); *C12Q 1/6816* (2013.01); *G06N 5/02* (2013.01); *G16B 40/00* (2019.02); *G16B 99/00* (2019.02); *C12N 2310/20* (2017.05)

(58) Field of Classification Search
None
See application file for complete search history.

(56) References Cited

U.S. PATENT DOCUMENTS

| | | |
|---|---|---|
| 7,056,724 B2 | 6/2006 | Wong et al. |
| 7,659,590 B2 | 2/2010 | Boland et al. |
| 9,384,320 B2 | 7/2016 | Church |
| 9,957,526 B2 | 5/2018 | Holmes et al. |
| 2002/0061528 A1 | 5/2002 | Gardner et al. |
| 2005/0053968 A1 | 3/2005 | Bharadwaj et al. |
| 2012/0003630 A1 | 1/2012 | Collins et al. |
| 2012/0296857 A1 | 11/2012 | Burns et al. |
| 2014/0315310 A1 | 10/2014 | Lu et al. |
| 2015/0133315 A1 | 5/2015 | Jacobson et al. |
| 2015/0225801 A1 | 8/2015 | Cai et al. |
| 2015/0261664 A1 | 9/2015 | Goldman et al. |
| 2015/0269313 A1 | 9/2015 | Church |
| 2015/0368639 A1 | 12/2015 | Gill et al. |
| 2016/0168592 A1 | 6/2016 | Church et al. |
| 2016/0312313 A1 | 10/2016 | Kotula et al. |
| 2016/0333363 A1 | 11/2016 | Srivastava |
| 2017/0096680 A1 | 4/2017 | Lu et al. |
| 2017/0369870 A1 | 12/2017 | Gill et al. |
| 2018/0002725 A1 | 1/2018 | Ganjam |
| 2018/0002748 A1 | 1/2018 | Ganjam |
| 2018/0004537 A1 | 1/2018 | Ganjam |

FOREIGN PATENT DOCUMENTS

| | | |
|---|---|---|
| KR | 20150027756 A | 3/2015 |
| KR | 20160001455 A | 1/2016 |
| WO | WO2013/169867 A1 | 11/2013 |
| WO | WO2015/176990 A1 | 11/2015 |
| WO | WO2015/199614 A1 | 12/2015 |
| WO | WO2016/025719 A1 | 2/2016 |
| WO | WO2016/040594 A1 | 3/2016 |
| WO | WO2016/059610 A1 | 4/2016 |
| WO | WO2016/183438 A1 | 11/2016 |
| WO | WO2016/205728 A1 | 12/2016 |
| WO | 2018005117 A1 | 1/2018 |

(Continued)

OTHER PUBLICATIONS

Andrianantoandro, Ernesto, et al. "Synthetic biology: new engineering rules for an emerging discipline." Molecular systems biology 2.1 (2006): 2006-0028.*
Sheth, Ravi U., and Harris H. Wang. "DNA-based memory devices for recording cellular events." Nature Reviews Genetics (2018): 1.*
Wikipedia, "Homology directed repair," Jul. 15, 2019 download from "https://en.wikipedia.org/wiki/Homology_directed_repair".*
Schmidt, Florian, and Randall J. Platt. "Applications of CRISPR-Cas for synthetic biology and genetic recording." Current Opinion in Systems Biology 5 (2017): 9-15.*
Ben-Aroya, et al., "Making temperature-sensitive mutants", In Proceedings of the Methods in Enzymology, Mar. 1, 2010, 23 Pages.
Dow, et al., "Inducible in vivo genome editing with CRISPR-Cas9", Retrieved From: https://www.ncbi.nlm.nih.gov/pmc/articles/PMC4390466/pdf/nihms-658413.pdf, Apr. 1, 2015, 14 Pages.

(Continued)

*Primary Examiner* — G Steven Vanni
(74) *Attorney, Agent, or Firm* — Newport IP, LLC; Benjamin A. Keim

(57) ABSTRACT

A log of molecular events experienced by a cell and timing indicators for those events are stored in existing polynucleotides through a process of creating a double strand break ("DSB") in a polynucleotide and inserting a new polynucleotide sequence by repairing the DSB with homology directed repair ("HDR"). The presence, order, and number of new polynucleotide sequences provides a log of events and timing of those events. Cellular mechanisms for creating the DSB and/or repairing with HDR are regulated by intra- or extra-cellular signals. When the log is created in the DNA of a cell, the changes may be heritably passed to subsequent generations of the cell. A correlation between the cellular signals and sequence of inserted HDR templates allows for identification of events and the timing experienced by the cell.

18 Claims, 14 Drawing Sheets
Specification includes a Sequence Listing.

(56) References Cited

FOREIGN PATENT DOCUMENTS

| WO | 2018005289 A2 | 1/2018 |
|---|---|---|
| WO | 2018005289 A3 | 1/2018 |
| WO | 2018005782 A1 | 1/2018 |
| WO | 2018005824 A1 | 1/2018 |

OTHER PUBLICATIONS

Dow, et al., "Inducible in vivo genome editing with CRISPR-Cas9", In Journal of the Nature Biotechnology, vol. 33, No. 4, Apr. 1, 2015, 7 Pages.
Espeso, et al., "pH regulation is a major determinant in expression of a fungal penicillin biosynthetic gene", In the EMBO Journal, vol. 12, Issue 10, Oct. 1, 1993, pp. 3947-3956.
Fan, et al., "Combinatorial labeling of single cells for gene expression cytometry", In Proceedings of the Science, vol. 347, No. 6222, Feb. 5, 2015, 8 Pages.
Fan, H Christina., et al., "Expression profiling. Combinatorial labeling of single cells for gene expression cytometry", Retrieved From: http://science.sciencemag.org/content/347/6222/1258367, vol. 347, Issue 6222, Feb. 6, 2015, 10 Pages.
Heid, et al., "Real time quantitative PCR", In the Book of Genome Research, vol. 6, Issue 10, Oct. 1, 1996, pp. 986-994.
Hossein Tabatabaei Yazdi, et al., "GBlocks Gene Fragments—Related Decoded Articles", Retrieved From: https://web.archive.org/web/20150912022743/http://www.idtdna.com/pages/products/genes/gblocks-gene-fragments/decoded-articles/decoded/2013/12/13/crispr-and-cas9-for-flexible-genome-editing, Sep. 18, 2015, 10 Pages.
Hussain, Faiza, et al., "Engineered temperature compensation in a synthetic genetic clock", Retrieved From: http://www.pnas.org/content/pnas/111/3/972.full.pdf, Jan. 21, 2014, pp. 972-977.
Lafountaine, et al., "Delivery and therapeutic applications of gene editing technologies ZFNs, TALENs, and CRISPR/Cas9", In International Journal of Pharmaceutics, vol. 494, Aug. 13, 2015, pp. 180-194.
Macosko, et al., "Highly Parallel genome-wide expression profiling of individual cells using nanoliter droplets", In Proceedings of the Cell, vol. 161, Issue 5, May 1, 2015, pp. 1202-1214.
Mali, et al., "Supplementary information for RNA-Guided Human Genome Engineering via Cas9", In Journal of Science, vol. 339, Issue 6121, Jan. 3, 2013, 35 Pages.
Neupert, Juliiane, et al., "Design of simple synthetic RNA thermometers for temperature-controlled gene expression in *Escherichia coli*", In Nucleic Acids Research, vol. 36, No. 19 e124, Aug. 27, 2008, 9 Pages.
Nitsche, et al., "Different real-time PCR formats compared for the quantitative detection of human cytomegalovirus DNA", In the Clinical Chemistry, vol. 45, Issue 11, Jan. 1, 1999, pp. 1932-1937.
O'Driscoll, et al., "Synthetic DNA :The Next Generation of Big Data Storage", In Journal of Science, vol. 4, Issue 3, May 1, 2013, 4 Pages.
"International Search Report and Written Opinion Issued in PCT Application No. PCT/US2017/037731", dated Sep. 25, 2017, 12 Pages.
"International Search Report and Written Opinion Issued in PCT Application No. PCT/US2017/039976", dated Oct. 18, 2017, 12 Pages.
"International Search Report and Written Opinion Issued in PCT Application No. PCT/US2017/040046", dated Oct. 10, 2017, 14 Pages.
Vishwakarma, et al., "High Density Data Storage in Dna Using an Efficient Message Encoding Scheme", In International Journal of Information Technology Convergence and Services, vol. 2, Issue 2, Apr. 30, 2012, pp. 41-46.
Yazdi, et al., "A Rewritable, Random-Access DNA-Based Storage System", In Journal of Scientific Reports, vol. 5, Sep. 18, 2015, 10 Pages.

"Non-Final Office Action issued in U.S. Appl. No. 15/623,925", dated Aug. 28, 2018, 12 Pages.
"International Application Serial No. PCT/US2017/039063, Invitation to Pay Additional Fees and Partial Search Report dated Oct. 5, 2017", 14 pgs.
Danino, Tal, et al., "A synchronized quorum of genetic clocks", *Nature*, vol. 463, (2010), 326-330.
Kulkarni, A. S., et al., "Stimulation of Homology-Directed Repair at I-SceI-Induced DNA Breaks during the Permissive Life Cycle of Human Cytomegalovirus", *Journal of Virology*, 85(12), (Jun. 2011), 6049-6054.
Ryback, Brendan M, et al., "Design and analysis of a tunable synchronized oscillator", *Journal of Biological Engineering*, 7(26), (2013), 1-10.
U.S. Appl. No. 62/357,828, Ganjam, et al., Storage Through Iterative DNA Editing, filed Jul. 1, 2016, 20 pages.
U.S. Appl. No. 62/399,190, Ganjam, Kris K, Storage Through Iterative DNA Editing, filed Sep. 23, 2016, 79 pages.
U.S. Appl. No. 62/487,671, Ganjam, Kris K., Mechanisms for Molecular Event Logging, filed Apr. 20, 2017, 92 pages.
"Addgene", Retrieved on: Sep. 14, 2016 Available at: https://www.addgene.org/crispr/guide/, 17 pages.
Bate, G, "Bits and genes: A comparison of the natural storage of information in DNA and digital magnetic recording", In Journal of IEEE Transactions on Magnetics, vol. 14, Issue 5, Published on: Sep. 1978, 2 pages.
Bonnet, et al., "Rewritable digital data storage in live cells via engineered control of recombination directionality", In Journal of PNAS, vol. 109, No. 23, Jun. 5, 2012, pp. 8884-8889.
Byrne, Michael, "Scientists Built a Biological Computer inside a Cell", Published on: Jul. 21, 2016, Available at: http://motherboard.vice.com/read/engineers-develop-key-building-block-for-sophisticated-bio-computers, 6 pages.
Caliando, et al., "Targeted DNA degradation using a CRISPR device stably carried in the host genome", In Journal of Nature communications, vol. 6, May 19, 2015, 10 pages.
Chu, et al., "Increasing the efficiency of homology-directed repair for CRISPR-Cas9-induced precise gene editing in mammalian cells," Nature Biotechnology, published online Mar. 24, 2015, 9 pages.
"CRISPR/Cas Tools", Retrieved on: Sep. 14, 2016 Available at: https://en.wikipedia.org/wiki/CRISPR/Cas_Tools, 3 pages.
Davis, et al., "Homology-directed repair of DNA icks via pathways distinct from canonical double-strand break repair," PNAS, www.pnas.org/cgi/doi/10.1073/pnas.1400236111, Feb. 2014, 9 pages.
Defrangesco, Ralph M., "Biological Cells as Storage Devices", In Proceedings of Ninth International Conference on Information Technology: New Generations, Apr. 16, 2012, pp. 897-898.
"Editas medicine", Retrieved on: Sep. 14, 2016, Available at: http://www.editasmedicine.com/, 1 page.
Farboud, et al., "Dramatic Enhancement of Genome Editing by CRISPR/Cas9 Through Improved Guide RNA Design," Genetics, vol. 199, 959-971, Apr. 2015, 18 pages.
Fusi, et al, "In Silico Predictive Modeling of CRISPR/Cas9 Guide Efficiency", BioRxiv, 2015, http://dx.doi.org/10.1101/021568, 31 pages.
Gao, et al. "DNA-guided genome editing using the Natronobacterium gregoryi Argonaute", In Journal of Nature Biotechnology, vol. 34, May 2, 2016, 8 pages.
Gearing, Mary, "Cpf1: A New Tool for CRISPR Genome Editing", Published on: Oct. 14, 2015, Available at: http://blog.addgene.org/cpf1-a-new-tool-for-crispr-genome-editing, 5 pages.
Glaser, et al., "Statistical Analysis of Molecular Signal Recording", PLos Comput. Biol., 2013, vol. 9 (7), e1003145, 14 pages.
He, et al., "Knock-in of large reporter genes in human cells via CRISPR/Cas9-induced homology-dependent and Independent DNA repair", In Journal of Nucleic Acids Research, vol. 44, No. 9, Feb. 4, 2016, pp. 1-14.
Heler, et al., "Mutations in Cas9 Enhance the Rate of Acquisition of Viral Spacer Sequences during the CRISPR-Cas Immune Response," Molecular Cell 65, 168-175, Jan. 2017, 9 pages.

(56) References Cited

OTHER PUBLICATIONS

Hsiao, et al., "A population based temporal logic gate for timing and recording chemical events", In Journal of Molecular Systems Biology, vol. 12, Issue 869, May 17, 2016, pp. 1-14.
Irving, Michael, "New record for storing digital data in DNA", Published on: Jul. 11, 2016 Available at: http://newatlas.com/dna-data-storage-record/44273/, 5.
Ji, et al. "Specific Gene Repression by CRISPRi System Transferred through Bacterial Conjugation", In Publication of ACS Synthetic Biology, vol. 3, Issue 12, Dec. 2014, pp. 929-931.
Kalhor, et al., "Rapidly evolving homing CRISPR barcodes", In Journal of Nature Methods, vol. 14, Dec. 5, 2016, 3 pages.
Kawane, et al., "DNA Degradation and Its Defects," Cold Spring Harb Perspect Biol 2014;6:a016394, 15 pages.
Keskin, et al., "Transcript-RNA-templated DNA recombination and repair," Nature 515, Nov. 20, 2014, 436-439.
Khoso, Mikal, "Storing Digital Data in DNA", Published on: May 18, 2016 Available at: http://www.northeastern.edu/levelblog/2016/05/18/storing-data-dna/, 3 pages.
Kim, et al., "Synthetic in vitro transcriptional oscillators," Molecular Systems Biology 7:465, 2011, 15 pages.
Kowalczykowski, "Chapter 7, Homologous Recombination Proteins and their Potential Applications in Gene Targeting Technology," CRC Press, Inc., 1995, 44 pages.
Kowalczykowski, "In vitro reconstitution of homologous recombinaton reactions," Experientia 50 (1994), Birkhauser Verlag, Ch-4010 Basel/Switzerland, 13 pages.
Krejci, et al., "Homologous recombination and its regulation," Nucleic Acids Research, 2012, vol. 40, No. 13, Mar. 2012, 24 pages.
Kumar, et al., "Secret data writing using DNA sequences", In Proceedings of International Conference on Emerging Trends in Networks and Computer Communications, Apr. 22, 2011, pp. 402-405.
Kupferschmidt, Kai, "Genome editor CRISPR helps trace growth of embryos and maybe cancer next", http://www.sciencemag.org/news/2016/05/genome-editor-crispr-helps-trace-growth-embryos-and-maybe-cancer-next, Published on: May 26, 2016, 9 pages.
Lakin, et al., "Modelling, Simulating and Verifying Turing-Power, Strand Displacement Systems," International Conference on DNA Computing and Molecular Programming, Sep. 2011, 15 pages.
Lebar, et al., "A bistable genetic switch based on designable DNA-binding domains", In Journal of Nature Communications, vol. 5, Sep. 29, 2014, pp. 1-13.
Lee, "Genome editing in vivo with the delivery of Cas9 ribonucleoprotein and donor DNA complexed to gold nanoparticles," abstract, 5th International Conference and Exhibition on Cell and Gene Therapy May 2016, 1 page.
Lee, et al., "RNA-Guided Genome Editing in *Drosophila* with the Purified Cas9 Protein", In Journal of G3 Bethesda, vol. 4, Jul. 2014, pp. 1291-1295.
Lenz, et al., "Temporal and spatial oscillations in bacteria," Nature Reviews Microbiology, vol. 9, Aug. 2011, 14 pages.
Lewin, "Chapter 8 Recombination of DNA," ttp://www.bx.psu.edu/~ross/workmg/RecombineDNACh8.htm, downloaded Jun. 27, 2017, 28 pages.
Li, et al., "Harnessing homologous recombination in vitro to generate recombinant DNA via SLIC," Nature Methods, vol. 4, No. 3, Mar. 2007, 7 pages.
Limbachiya, et al., "On optimal family of codes for archival DNA storage", In Proceedings of Seventh International Workshop on Signal Design and its Applications in Communications, Sep. 14, 2015, pp. 123-127.
Marblestone, et al., "Physical Principles for Scalable Neural Recording", Frontiers in Computational Neuroscience, 2013, vol. 7, Article 137, 34 pages.
Marblestone, et al., "Rosetta Brains: A Strategy for Molecularly-Annotated Connectomics", 2014, https://arxiv.org/abs/1404.5103, 18 pages.

Maruyama, et al., "Increasing the efficiency of precise genome editing with CRISPR-Cas9 by inhibition of nonhomologous end joining," Nature Biotechnology, vol. 33, No. 5, May 2015, 9 pages.
Mcdade, Joel, "The PAM Requirement and Expanding CRISPR Beyond SpCas9", Published on: Nov. 12, 2015, Available at: http://blog.addgene.org/the-pam-requirement-and-expanding-crispr-beyond-spcas9 , 6 pages.
McKenna, et al., Whole organism lineage tracing by combinatorial and cumulative genome editing,: Science, published online May 26, 2016, doi: 10,1126/science.aaf7907, 13 pages.
McKenna, et al., "Whole organism lineage tracing by combinatorial and cumulative genome editing," bioRxiv, May 11, 2016, http://dx.doi.org/10.1101/052712, May 11, 2016, 34 pages.
Morrical, "DNA-Pairing and Annealing Processes in Homologous Recombination and Homology-Directed Repair," Cold Spring Harb Perspect Bio 2015;7:a016444, 2015, 21 pages.
Nelles, et al., "Programmable RNA Tracking in Live Cells with CRISPR/Cas9," Cell, 165, 488-496, Apr. 2016, 10 pages.
Nielsen, et al., "Multi-input CRISPRCas genetic circuits that interface host regulatory networks", In Journal of Molecular Systems Biology, vol. 10, Nov. 24, 2014, pp. 1-11.
Farzadfard, et al., "Genomically Encoded Analog Memory with Precise in Vivo DNA Writing in Living Cell Populations", In Science, vol. 346, Issue 6211, Nov. 14, 2014, 9 Pages.
Jusiak, et al., "Engineering Synthetic Gene Circuits in Living Cells with CRISPR Technology", In Publication of Trends in Biotechnology, vol. 34, Issue 7, Jul. 2016, pp. 535-547.
"International Search Report and Written Opinion Issued in PCT Application No. PCT/US2017/039063", dated Jan. 10, 2018, 21 Pages.
O'Neill, et al., "Circadian rhythnms persist without transcription in a eukaryote," Nature, vol. 467, Issue 7331, doi:10.1038/nature09654, Jan. 2011, 11 pages.
Perli, et al., "Continuous genetic recording with self-targeting CRISPR-Cas in human cells", In Journal of Science, vol. 353, Issue 6304, Sep. 9, 2016, 4 pages.
Petersen, "A strand graph semantics for DNA-based computation," Theor Comput Sci. 632: doi:10.1016/j.tcs.2015.07.041, Jun. 2016, 50 pages.
Prindle, et al., "A sensing array of radically coupled genetic 'biopixels'," Nature, http://www.nature.com/nature/journal/v481/n7379/abs/nature10722.html, 2011, 19 pages.
Prindle, et al.,. "Rapid and tunable post-translational coupling of genetic circuits," Nature. vol. 508, Issue 7496, Apr. 2017, 15 pages.
Proudfoot, "Ending the message: poly(A) signals then and now," Genes & Development 25:1770-1782 Cold Spring Harbor Laboratory Press, 2011, 14 pages.
Purcell, et al., "A comparative analysis of synthetic genetic oscillators," Journal of the Royal Society Interface, http://rsif.royalsocietypublishing.org/content/7/52/1503, Jun. 2010, 22 pages.
Qi, et al., "Repurposing CRISPR as an RNA-guided platform for sequence-specific control of gene expression", In Journal of Cell, vol. 152, Issue 5, Feb. 28, 2013, pp. 1173-1183.
Ran, et al., "Double Nicking by RNA-Guided CRISPR Cas9 for Enhanced Genome Editing Specificity," Cell 154, 1380-1389, Sep. 2013, 10 pages.
Raymond, et al., "Deinococcus radiodurans RNA ligase exemplifies a novel ligase clade with a distinctive N-terminal module that is important for 5'-PO4 nick sealing and ligase adenylylation but dispensable for phosphodiester formation at an adenylylated nick," Nucleic Acids Research, vol. 35, No. 3, Jan. 2007, 11 pages.
Reilly, Patrick, "Why is mRNA fed into the CRISPR Cas9 system and not DNA", Published on: Jun. 5, 2015, Available at: https://www.quora.com/Why-is-mRNA-fed-into-the-CRISPR-Cas9-system-and-not-DNA, 2 pages.
Roquet, et al., Synthetic recombinase-based state machines in living cells, published in Sciencemag.org on Jul. 2016, 15 pages.
Sekiguchi, et al., "Ligation of RNA-Containing Duplexes by Vaccinia DNA Ligase," Biochemistry, Americal Chemical Society, May 1997, 7 pages.
Shimanovsky, et al., "Hiding Data in DNA", In Proceedings of the Revised Papers from the 5th International Workshop on Information Hiding, Oct. 7, 2002, 15 pages.

(56) References Cited

OTHER PUBLICATIONS

Shipman, et al., "Molecular Recordings by Directed CRISPR Spacer Acquisition", Science, 2016, 16 pages.
Shipman, et al., "Molecular recordings by directed CRISPR spacer acquisition", In Journal of Science, vol. 353, Issue 6298, Sep. 9, 2016, 3 pages.
Silas, et al., "Direct CRISPR spacer acquisition from RNA by a natural reverse transcriptase-Cas1 fusion protein," Science, vol. 351 Issue 6276, Feb. 26 2016, 14 pages.
Sriskanda, et al., "Specificity and fidelity of strand joining by Chlorella virus DNA ligase," Nucleic Acids Research, vol. 26, No. 15, Apr. 1998, 6 pages.
Stricker, et al., "A fast, robust and tunable synthetic gene oscillator," Nature, vol. 456, Nov. 2008, 38 pages.
Tamsir, et al., "Robust multicellular computing using genetically encoded NOR gates and chemical 'wires'", In Journal of Nature, vol. 469, Dec. 8, 2010, pp. 1-4.
Tigges, et al., "A tunable synthetic mammalian oscillator," Nature, vol. 457, Jan. 2009, doi:10.1038/nature07616, 4 pages.
Trafton, Anne, "Engineers program human cells to store complex histories in their DNA", Published on: Aug. 18, 2016, Available at: http://phys.org/news/2016-08-human-cells-complex-histories-dna.html, 4 pages.
Trafton, Anne, "Human DNA cells genetically engineered to store memories and complex histories", Published on: Aug. 23, 2016, Available at: https://futuristech.info/posts/human-dna-cells-genetically-engineered-to-store-memories-and-complex-histories, 3 pages.
Tsai, "Robust, Tunable Biological Oscillatons from Interlinked Positive and Negative Feedback Loops," Science, vol. 321, Jul. 2008, 19 pages.
Unciuleac, et al., "Characterization of a novel eukaryal nick-sealing RNA ligase from Naegleria Gruberi," RNA, vol. 21, 824-832, Mar. 2015, 10 pages.
Waters, Virginia L., "Conjugation between bacterial and mammalian cells", In Journal of Nature Genetics, vol. 29, Nov. 19, 2001, pp. 375-376.
Weinberg, et al., "Large-scale design of robust genetic circuits with multiple inputs and outputs for mammalian cells," published in Nature Biotechnology Jan. 2017, 12 pages.
Weintraub, Karen, "CRISPR gene-editing system unleashed on RNA", http://www.nature.com/news/crispr-gene-editing-system-unleashed-on-ma-1.20030, Published on: Jun. 3, 2016, 3 pages.
"Cas9", Retrieved on: Sep. 14, 2016 Available at: https://en.wikipedia.org/wiki/Cas9, 6 pages.
"CRISPR interference", Retrieved on: Sep. 14, 2016 Available at: https://en.wikipedia.org/wiki/CRISPR_interference, 4 pages.
"Gene drive ", Retrieved on: Sep. 14, 2016, Available at: https://en.wikipedia.org/wiki/Gene_drive, 4 pages.
Williams, Sarah C.P, "DNA tape recorder stores a cell's memories", Published on: Nov. 23, 2014, Available at: http://www.sciencemag.org/news/2014/11/dna-tape-recorder-stores-cells-memories, 9 pages.
Woods, et al., "A Statistical Approach Reveals Designs for the Most Robust Stochastic Gene Oscillators", In Journal of ACS Synthetic Biology, Feb. 2, 2016, pp. 459-470.
Wu, et al, "Target specificity of the CRISPR-Cas9 system," Quant Biol, Jun. 2014; (2): 59-70. https://www.ncbi.nlm.nih.gov/pmc/articles/PMC4338555/, 19 pages.
Yang, et al., "Enrichment of G2/M cell cycle phase in human pluripotent stem cells enhances HDR-mediated gene repair with customizable endonucleases," Nature.com/scientificreports/ Feb. 2016, 15 pages.
Yang, et al., "Permanent Genetic Memory with less than 1-Byte Capacity", Nat. Methods, 2014, vol. 11 (12), pp. 1261-1266.
Yin, et al., "Thereapeutic genome editing by combined viral and non-viral delivery of CRISPR system components in vivo," Nat Biotechnol. 34(3), Mar. 2016, 15 pages.
Yordanov, et al., "Functional Analysis of Large-scale DNA Strand Displacement Circuits," International Conference on DNA Computing and Molecular Programming, Sep. 2013, 15 pages.
Yosef, et al., "Proteins and DNA elements essential for the CRISPR adaptation process in *Escherichia coli*," Nucleic Acids Research, 40 (12), Jul. 2012, 9 pages.
Zuris, et al , "Cationic lipid-mediated delivery of proteins enables efficient protein-based genome editing in vitro and in vivo," Nature Biotechnology, published online Oct. 30, 2014, 60 pages.
"Final Office Action Issued in U.S. Appl. No. 15/623,925", dated Jan. 22, 2019, 6 Pages.
"Final Office Action Issued in U.S. Appl. No. 15/626,021", dated Feb. 11, 2019, 7 Pages.
"Final Office Action Issued in U.S. Appl. No. 15/626,020", dated May 31, 2019, 17 Pages.
Wingler, et al., "Reiterative Recombination for the in vivo assembly of libraries of multigene pathways", In Proceedings of the National Academy of Sciences, Sep. 13, 2011, 6 Pages.
"Non-Final Office Action Issued in U.S. Appl. No. 15/623,925", dated May 8, 2019, 12 Pages.
"Non Final Office Action Issued in U.S. Appl. No. 15/626,020", dated Oct. 31, 2018, 17 Pages.
"Non Final Office Action Issued in U.S. Appl. No. 15/626,021", dated Sep. 24, 2018, 10 Pages.
Findlay, et al., "Saturation Editing of Genomic Regions by Multiplex Homology-Directed Repair", In Journal Nature, vol. 513, Issue 7516, Sep. 3, 2014, pp. 120-123.
Paquet, et al., "Efficient Introduction of Specific Homozygous and Heterozygous Mutations Using CRISPR/Cas9", In Journal Nature, vol. 533, Issue 7601, Apr. 27, 2016, pp. 125-129.
Quetier, Francis, "The CRISPR-Cas9 technology: Closer to the ultimate toolkit for targeted genome editing", In Proceedings of the Plant Science, vol. 242, Sep. 8, 2015, pp. 65-76.
Sorek, et al., "CRISPR-Mediated Adaptive Immune Systems in Bacteria and Archaea", In Proceedings of the Annual Review of Biochemistry, vol. 82, Mar. 11, 2013, pp. 237-266.
Sun, et al., "Recent advances in targeted genome engineering in mammalian systems", In Proceedings of the Biotechnology journal, vol. 7, Issue 9, Jul. 10, 2012, pp. 1074-1087.
Wang, et al., "Genetic screens in human cells using the CRISPR/Cas9 system", Retrieved from: https://www.ncbi.nlm.nih.gov/pmc/articles/PMC3972032/, Jan. 3, 2014, 12 Pages.
"Non Final Office Action Issued in U.S. Appl. No. 15/626,021", dated Jul. 12, 2019, 10 Pages.
Mali, et al., "RNA-Guided Human Genome Engineering via Cas9", In Journal of Science, vol. 339, Issue 6121, Feb. 15, 2013, 8 Pages.
Pierce, et al., "XRCC3 promotes homology-directed repair of DNA damage in mammalian cells", In Journal of the Genes & development, vol. 13, Issue 20, Oct. 15, 1999, pp. 2633-2638.
"Final Office Action Issued in U.S. Appl. No. 15/623,925", dated Nov. 25, 2019, 12 Pages.
"Final Office Action Issued in U.S. Appl. No. 15/626,021", dated Nov. 22, 2019, 9 Pages.
"Search Report Issued in European patent Application No. 19185657.4", dated Dec. 9, 2019, 8 Pages.
"Office Action Issued in European Patent Application No. 17742885.1", dated Feb. 20, 2020, 7 Pages.
"Extended Search Report Issued in European Patent Application No. 19185656.6", dated Mar. 13, 2020, 8 Pages.
"Office Action Issued in European Patent Application No. 17736842.0", dated May 11, 2020, 3 Pages.
"Office Action Issued in European Patent Application No. 17736842.0", dated Aug. 18, 2020, 5 pages.

* cited by examiner

HDR Template for Timing Indicator

USE OF HOMOLOGY DIRECT REPAIR TO RECORD TIMING OF A MOLECULAR EVENT

CROSS-REFERENCE TO RELATED APPLICATION

This application claims the benefit of U.S. Provisional Patent Application Ser. No. 62/357,828 filed on Jul. 1, 2016, entitled "Storage Through Iterative DNA Editing," U.S. Provisional Application Ser. No. 62/399,190 filed on Sep. 23, 2016, entitled "Storage Through Iterative DNA Editing," and 62/487,671 filed on Apr. 20, 2017, entitled "Mechanisms for Molecular Event Logging" all of which are expressly incorporated herein by reference in their entirety. This application is related to U.S. Patent Application entitled "Molecular State Machines" with U.S. patent application Ser. No. 15/626,020 and U.S. Patent Application entitled "Barcodes for Identification of Gene Expression" with U.S. patent application Ser. No. 15/626,021, both filed the same day as this application and the entirety of which are both expressly incorporated herein by reference.

BACKGROUND

The ability to sense and record information through microscopic, inexpensive and easy-to-fabricate devices (i.e., cells) has dramatic potential for numerous sensing applications including diagnostic health measurements within an organism or sensing physical phenomena on a larger scale such as environmental toxin levels in a river. Furthermore, the ability to log the internal state of a single cell provides many opportunities for deeper understanding and research into how individual biological cells operate in both health and disease states within their normal, living context. The ability to create such logs is further enhanced by a mechanism that can track the timing of logged events.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

Internal and external states or stimuli (e.g., temperature, pH, levels of a given molecule, membrane-bound receptors for light, chemicals, or other stimuli or measurable quantity that may be transduced via proteins and/or ribonucleic acid (RNA)) of a cell may be recorded into a stable polynucleotide (e.g., deoxyribonucleic acid (DNA), RNA, or DNA-RNA hybrids) memory that resides within the cell. This record of the sensed states or stimuli may be heritable and passed to subsequent cellular generations. The record can be read by sequencing of the polynucleotide. Thus, the stable polynucleotide creates a record analogous to a log file of states or stimuli experienced by the cell. Particular nucleic acid sequences may also be incorporated into the stable polynucleotide in response to events that occur at known times. Use of the time-correlated inserts can provide temporal information together with the record of the sensed states or stimuli.

Precise gene editing techniques such as CRISPR/Cas (Clustered regularly interspaced short palindromic repeats/CRISPR associated protein) systems and TALEN (transcription activator-like effector nucleases) enable manipulation of polynucleotides in a way that incorporates pre-determined polynucleotide sequences into an existing polynucleotide. With these techniques, a record may be sequentially written to a polynucleotide so that the signal being recorded does not require any external control signals and may be performed through automatic, periodic sampling of an input state. The cell may be modified by addition of a vector that includes genes or an operon which creates gene products used for logging molecular events. Timing of events may be recorded by manually exposing the cell to a condition that results in incorporation of a particular sequence that can later be correlated with the time of exposure. Use of a gene oscillator or other cellular machinery that creates a periodic signal can also be used to trigger the insertion of polynucleotide sequences that record the passage of time.

A polynucleotide in the cell may be cut to create a double strand break ("DSB"). A new polynucleotide sequence may be inserted into the DSB using homology directed repair ("HDR"). Making the DSB and integrating the HDR templates in response to signals creates a record in the polynucleotide of events experienced by the cell and their timing.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
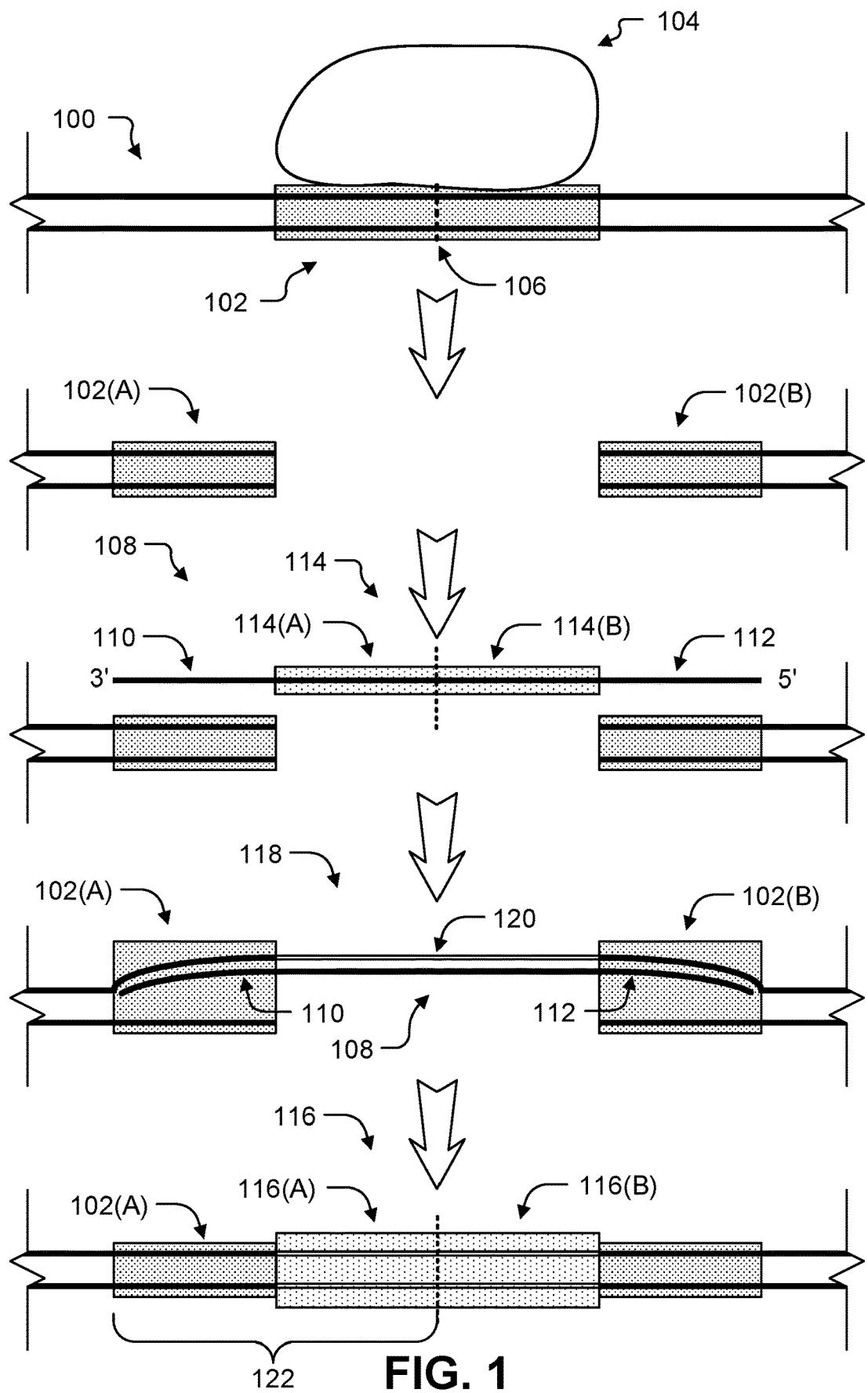
FIG. 1 shows a schematic representation of cutting dsDNA with an enzyme and inserting new DNA by HDR.

This disclosure presents techniques for recording molecular events sensed by a cell and timing associated with those events in the genetic material of that cell. The molecular events and the timing events, referred to as "clock signals," are both integrated into genetic material of the cell creating a stable, heritable record. The cell can be modified to incorporate known polynucleotide sequences when exposed to particular signals. This provides a log of the molecular events sensed by the cell. The cell can also be modified to incorporate known polynucleotide sequences at specific time points either manually triggered or in response to a natural or synthetic cellular cycle. Both molecular events and timing may be recorded together to provide a log that indicates the time specific molecular events were experienced by the cell. Alternatively, either may be implemented separately to provide a log of molecular events without timing information or to track passage of time independent of specific molecular events.

The genetic material is a "polynucleotide" which is often DNA but may also be RNA or a hybrid combination of DNA and RNA. The polynucleotide may or may not include one or more artificial nucleotides (e.g isoguanine, isocytosine, diaminopurine, etc.). References to "DNA" herein are understood to include all types of polynucleotides unless context specifically indicates otherwise. The detectable, molecular event may be an intra-cellular or extra-cellular event that results in generation of a signal that can be detected by a cellular system. Examples of molecular events include exposure to a chemical, a change in temperature, exposure to light (or dark), exposure to radiation, the presence of an antigen, a change in ionic concentration such as pH, etc. The molecular event may represent an external environmental condition or internal condition experienced by the cell. Timing indicators are also included in the genetic material of the cell. Timing indicators may be generated by manual action such as periodically exposing the cell to a condition that results in integration of a known sequence of DNA into the genome. This timing can be recorded and then later identification of these in such sequences may be correlated with the recorded times. Alternatively, the cell may be modified to include a mechanism such as a genetic oscillator that periodically causes integration of DNA into the genome. The timing of the oscillations can be used to identify the relative difference in time between two different instances in which DNA was integrated into the genome.

The cellular system that detects the molecular event may include an extra-cellular receptor that responds to conditions outside the cell or an intra-cellular receptor that responds to conditions within the cell. The cellular system may communicate a signal detected by a receptor through a signaling pathway that ultimately results in modification of a polynucleotide. The signaling pathway may be an "engineered signaling pathway" that is a natural signaling pathway modified in part or an entirely synthetic pathway that is added to the cell. A signaling pathway may cause changes in a polynucleotide by controlling the expression of a gene product. Expression may be controlled by interaction between the signaling pathway and an inducible promoter. A promoter is a region of DNA that initiates transcription of a particular gene. In response to the signal, the signaling pathway may either turn on an inducible promoter, which increases transcription of the associated gene, or repress a promoter, which decreases transcription of the associated gene. The gene product from a gene controlled by the promoter is the component that is used to modify the polynucleotide. For example, the gene product may be an enzyme that cuts the polynucleotide or the gene product may be another polynucleotide that is used to modify the polynucleotide that already exists in the cell.

Modification of the polynucleotide in the cell may be performed through homology directed repair ("HDR"). HDR uses a template polynucleotide (usually DNA but RNA may also be used) to repair a double-stranded break ("DSB") in the polynucleotide. The repair removes the DSB and, based on the design of the template polynucleotide, referred to as an "HDR template" in this disclosure, may also add an additional polynucleotide sequence at the point of repair. Thus, a signal may cause a DSB to be created and then repaired through HDR in a way that adds a particular, additional polynucleotide sequence into the genetic material of the cell. Thereafter, presence of this polynucleotide sequence in the cell is an indication that the cell has experienced a particular molecular event. Design of engineered signaling pathways and homology repair templates creates an arbitrary association between a particular signal and a particular polynucleotide sequence. Similarly, HDR may be used to add polynucleotide sequences that represent particular time points. Thus, the molecular mechanism for integrating a new sequence into a polynucleotide is the same, but the significance is different depending on whether it was triggered by a particular molecular event or by something that occurred with a known timing.

By way of example only, a bacterial cell may be modified with a receptor that detects a particular chemical. The signal generated by that receptor may be passed through a signaling pathway to a promoter that increases the transcription of an HDR template that adds a particular DNA sequence, e.g. ACTAGA, to the genomic DNA of the bacterial cell when repairing a DSB. An enzyme creates a DSB at a predetermined position in the genomic DNA of the bacterial cell. The particular location of this DSB is specific based on the properties of the enzyme and is designed to be repaired by the corresponding HDR template. The chemical is detected by the receptor, which in turn leads to increased transcription of the homology repair template. When many copies of the homology repair template are present, one of those copies may be used to repair the DSB and add the sequence ACTAGA to the genomic DNA of the bacterial cell. Addition of the HDR template in response to detection of the chemical adds a new DNA sequence which itself may include a cut site for a different enzyme (e.g., there may be a cut site in the middle of the ACTAGA sequence). This other enzyme can create a DSB in the DNA added by the HDR template into which a second HDR template is incorporated that correlates with a time. The second HDR template may add, for example, the sequence GCT at the location of the cut site. This bacterial cell may be designed so that there are no cut sites for this other enzyme until after detection of the chemical and incorporation of the first HDR template. Thus, this construction adds a time indicator with each log of exposure to the chemical. Later, analysis of the DNA of the bacterial cell by DNA sequencing can detect the sequence ACT-GCT-AGA which then serves as a record that the cell was exposed to this particular chemical and indicates that the cell was exposed at the time that the second HDR template was available.

Homology Directed Repair

HDR is a mechanism in cells to repair DSBs. The most common form of HDR is homologous recombination. The HDR repair mechanism can be used by the cell when there is a homologous piece of DNA present to repair the DSB. HDR is considered a highly accurate mechanism for DSB repair due to the requirement of sequence homology between the damaged and intact donor strands of DNA. The process is nearly error-free if the DNA template used for repair is identical to the original DNA sequence at the DSB, or it can introduce very specific mutations into the damaged DNA if there are differences between the DNA template use for repair and the original DNA sequence. This disclosure discusses use of a homology repair template that adds a new DNA sequence at the point of the DSB as part of the repair process.

HDR includes homologous recombination (HR) and single-strand annealing (SSA) (Lieber. 2010 Annu. Rev. Biochem. 79:181-211). The most common form of HDR is HR which has the longest sequence homology requirements between the donor and acceptor DNA. Other forms of HDR include single-stranded annealing (SSA) and breakage-induced replication, and these require shorter sequence homology relative to HR. HDR at nicks (single-stranded breaks) can occur via a mechanism distinct from HDR at DSBs (Davis and Maizels. PNAS (0027-8424), 111 (10), p. E924-E932).

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

By "hybridizable" or "complementary" or "substantially complementary" it is meant that a polynucleotide (e.g. DNA or RNA) comprises a sequence of nucleotides that enables it to non-covalently bind, to another polynucleotide in a sequence-specific, antiparallel, manner (i.e., a polynucleotide specifically binds to a complementary polynucleotide) under the appropriate in vitro and/or in vivo conditions of temperature and solution ionic strength. As is known in the art, Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

It is understood in the art that the sequence of polynucleotide need not be 100% complementary to that of its target polynucleotide to be specifically hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target polynucleotide sequence to which they are targeted. For example, an antisense polynucleotide in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. Percent complementarity between particular stretches of polynucleotide sequences within polynucleotides can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

FIG. 1 shows an illustrative schematic of operations to add a new DNA sequence into a double-stranded DNA (dsDNA) 100 through HDR. The new DNA sequence may become the record of a molecular event experienced by a cell containing the dsDNA 100. The dsDNA 100 includes a target site 102 that directs an enzyme 104 to create a DSB in the dsDNA 100 within the target site 102 at a specific cut site 106. The DSB may be created with blunt ends or with sticky ends depending on the specific enzyme and technique for making the DSB. The target site 102 is a sequence of DNA recognized by an enzyme that creates DSBs in dsDNA. By "enzyme reactive conditions" it is meant that any necessary conditions are available in an environment (i.e., such factors as temperature, pH, and lack of inhibiting substances) which will permit the enzyme to function. Enzyme reactive conditions can be either in vitro, such as in a test tube, or in vivo, such as within a cell.

The target site 102 may be intentionally introduced into the dsDNA 100 to enable the manipulations described below. Alternatively, a pre-existing portion of the dsDNA 100 may be selected as the target site 102. If a pre-existing portion of the dsDNA 100 is selected as the target site 102, then the sequence of other components of the system will be designed with reference to the sequence of the target site 102. In some implementations, the target site 102 is unique such that there is only one target site 102 in the entire dsDNA strand and/or only one target site 102 throughout all the DNA in the cell. The dsDNA 100 may be genomic DNA inside a living prokaryotic or eukaryotic cell, DNA introduced to a living cell such as a plasmid or vector, or DNA in a cell-free system. The dsDNA 100 may exist as either linear or circular DNA prior to introduction of the DSB.

The enzyme 104 that creates the DSB may be any protein, protein-RNA complex, or protein-DNA complex (including multimeric complexes) that has the property of creating a DSB in dsDNA at the cut site 106. Non-limiting examples of suitable enzymes include restriction enzymes, homing endonucleases, zinc-finger nucleases (ZFNs), transcription activator-like effector nucleases (TALENs), CRISPR/Cas, and NgAgo. These types of enzymes are all examples of site-specific nucleases that are capable of causing a DSB at a cut site 106 within a target site 102. Further details about site-specific nucleases are provided below.

After creating a DSB at the cut site 106, the target site 102 is split into two subsequences 102(A), 102(B) on either side of the DSB. Each of the two subsequences 102(A), 102(B) may, in an implementation, be between 5 and 20 nucleotides (nt) in length. Thus, the target site 102 may, in an implementation, be between 10 and 40 nt in length. In some implementations, the two subsequences 102(A), 102(B) may contain identical DNA sequences. The cut site 106 may be located in the middle of the target site 102 or it may be located elsewhere within the target site 102. The schematic shown in FIG. 1 illustrates a DSB with blunt ends, but as described above DSBs with sticky ends are also covered within the scope of this disclosure.

AN HDR template 108 is brought into proximity of the dsDNA 100 with the DSB. The HDR template 108 is single strand (ss) DNA or ssRNA. The HDR template repairs the DSB and inserts a polynucleotide sequence through the process of homology directed repair. HDR templates used to create specific mutations or insert new elements into a gene require a certain amount of homology surrounding the target site that will be modified. Thus, the HDR template 108 includes a 3'-end sequence 110 complementary to the first subsequence of the target site 102(A) and a 5'-end sequence 112 complementary to a second subsequence of the target site 102(B). Because they are complementary sequences, the length of the 3-end sequence 110 and the 5'-end sequence 112 are the same or about the same as the respective subsequences of the target site 102(A), 102(B). Thus, both 3-end sequence 110 and the 5'-end sequence 112 may be between 5 and 20 nt in length. The middle portion of the HDR template 108 contains a region 114 encoding a second target site 116. This middle region 114 may contain two subsequences 114(A), 114(B) on either side of the point where the second target site 116 will be cut by a second enzyme. The length of the two subsequences 114(A), 114(B) in the middle portion 114 of the HDR template 108 may be different than the lengths of the two subsequences 102(A), 102(B) but may follow the same size range and be between five and 20 nt in length. Thus, the total length of the HDR template 108 may be between about 20 and 80 nt. Because the middle region 114 encodes a second target site 116, the HDR template 108 itself provides the basis for this process to be repeated iteratively. So long as a signal is detected by a cell and the components for creating a DSB and performing HDR are available, this process may continue until the signal ceases. Thus, a length of the inserted DNA may correlate with a duration of the signal.

The HDR template 108 then repairs the DSB through HDR. The efficiency of HDR may be low, and in some conditions, other repair mechanisms can predominate. The efficiency of HDR is determined in part by the concentration of donor DNA present at the time of repair, the length of the homology arms of the donor DNA, the cell cycle, and the activity of the endogenous repair systems. An overabundance of the HDR template 108 may be provided to increase efficiency of HDR. The overabundance of the HDR template 108 may be provided to a cell-free system by adding additional copies of the ssRNA or ssDNA manually or with the use of microfluidics. The HDR template 108 may also be provided, in overabundance if desired, by placing a gene encoding the HDR template 108 under control of a strong promoter and/or by having multiple copies of the gene encoding the HDR template 108 all undergoing transcription. In an implementation, this promoter may be regulated by a signaling pathway that responds to a signal. When the signal is detected, the promoter is turned on and more copies of the HDR template 108 are generated.

The 5'-ended DNA strand is resected at the DSB to create a 3' overhang. This will serve as both a substrate for proteins required for strand invasion and a primer for DNA repair synthesis. The HDR template 108 can then displace one strand of the homologous DNA duplex and pair with the other; this causes formation of hybrid DNA referred to as the displacement loop ("D loop") 118. The recombination intermediates can then be resolved to complete the DNA repair process. As mentioned above, an overabundance of the HDR template 108 may be provided. One of ordinary skill in the art will understand how to perform HDR with dsDNA 100 having a DSB and an HDR template 108. Possible protocols for performing HDR are provided in Jie Liu et al., *In Vitro Assays for DNA Pairing in Recombination-Associated DNA Synthesis*, 745 Methods Mol. Bio. 363 (2011); Gratz, S. et al., *Highly specific and efficient CRISPR/Cas9-catalyzed homology-directed repair in Drosophila*, 196 Genetics 967 (2014); Richardson, C. C. et al., *Enhancing homology-directed genome editing by catalytically active and inactive CRISPR-Cas9 using asymmetric donor DNA*, 34 Nature Biotechnology 399 (2016); and Lin, S. et al., *Enhanced homology-directed human genome engineering by controlled timing of CRISPR/Cas9 delivery*, eLIFE (2014).

After the HDR template 108 invades the dsDNA, the D loop 118 is formed by hybridization of the 3'-end sequence 110 to the first subsequence 102(A) of the target site 102 and hybridization of the 5'-end sequence 112 to the second subsequence 102(B) of the target site 102. DNA polymerase synthesizes new ssDNA 120 complementary to the middle portion 114 of one strand of the dsDNA 100. DNA ligase joins the sugar-phosphate backbone of the newly synthesized ssDNA 120 with the remainder of that strand of the dsDNA 100. This forms one strand of the second target site 116.

Hybridization requires that the two polynucleotides contain complementary sequences, although mismatches between bases are possible. The conditions appropriate for hybridization between two polynucleotides depend on the length of the polynucleotides and the degree of complementation which are variables well known in the art. The greater the degree of complementation between two nucleotide sequences, the greater the value of the melting temperature ($T_m$) for hybrids of polynucleotides having those sequences. For hybridizations between polynucleotides with short stretches of complementarity (e.g. complementarity over 35 nt or less, 30 nt or less, 25 nt or less, 22 nt or less, 20 nt or less, or 18 nt or less) the position of mismatches becomes important. This is understood by one of ordinary skill in the art and described in Sambrook, J. and Russell, W., Molecular Cloning: A Laboratory Manual, Third Edition, Cold Spring Harbor Laboratory Press, Cold Spring Harbor (2001) at sec. 11.7-11.8. Typically, the length for a hybridizable polynucleotide is at least about 10 nt. Illustrative minimum lengths for a hybridizable polynucleotide are: at least about 15 nt; at least about 20 nt; at least about 22 nt; at least about 25 nt; and at least about 30 nt). Furthermore, the skilled artisan will recognize that the temperature, pH, and wash solution salt concentration may be adjusted as necessary according to factors such as length of the region of complementation and the degree of complementation.

Following repair of the first strand of the dsDNA 100, the second strand of the dsDNA 100 is repaired by DNA polymerase and DNA ligase using the sequence of the new ssDNA 120 in the repaired, first strand as a template. This completes the repair of the dsDNA 100 resulting in dsDNA that includes the second target site 116 inserted within the first target site 102.

DNA polymerases are enzymes that synthesize DNA molecules from individual deoxyribonucleotides. During this process, DNA polymerase "reads" an existing DNA strand to create a new, complementary strand. DNA ligase is a specific type of enzyme, a ligase, that facilitates the joining of DNA strands together by catalyzing the formation of a phosphodiester bond. It plays a role in repairing single-strand breaks. The mechanism of DNA ligase is to form two covalent phosphodiester bonds between 3' hydroxyl ends of one nucleotide, ("acceptor") with the 5' phosphate end of another ("donor"). The DNA ligase from bacteriophage T4 is the ligase most-commonly used in laboratory research. It can ligate cohesive or "sticky" ends of DNA, oligonucleotides, as well as RNA and RNA-DNA hybrids, but not single-stranded polynucleotides. It can also ligate blunt-ended DNA.

Note that the HDR template 108 includes two types of regions: end regions and a middle region. The end regions are homologous to one of the strands of the dsDNA 100 on either side of the DSB. Here, the homologous regions are shown by the 3-end sequence 110 and the 5'-end sequence 112. The homology need not be 100% but only to the extent that the 3'-end sequence 110 and the 5'-end sequence 112 hybridize to one strand of the dsDNA 100. The middle region is the middle portion 114 of the HDR template 108 that encodes the sequence of the second target site 116. Independently varying both the end regions and the middle region allows for creation of multiple different HDR templates 108 from a relatively limited set of end regions and middle regions. Thus, the middle region of an inserted HDR template 108 need not have the same target site 102 or cut site 106 as the dsDNA 100 it is being inserted into.

Following HDR, the dsDNA 100 includes the first subsequence 102(A) of the first target site 102 followed by the first subsequence 116(A) of the second target site 116. The DNA sequence 122 represented by this order of the two subsequences 102(A), 116(A) of the two target sites may represent a particular signal combination (e.g., temperature above 30° C. followed by pH under 5). As mentioned above, a length of the subsequence 102(A) is from five to 20 nt and the length of the subsequence 114(A) is also from five to 20 nt. Thus, in an implementation, the total length of the DNA sequence 122 is from 10 to 40 nt.

HDR, however, is not the only way to repair a DSB. Non-Homologous End-Joining (NHEJ) is a pathway that repairs double-strand breaks in DNA and may be favored over HDR in many conditions. NHEJ is referred to as "non-homologous" because the break ends are directly ligated without the need for a homologous template. NHEJ is active throughout the cell cycle and has a higher capacity for repair, as there is no requirement for a repair template (sister chromatid or homologue) or extensive DNA synthesis. NHEJ also finishes repair of most types of breaks in tens of minutes—an order of magnitude faster than HDR. Thus, in many cells there is competition between HDR and NHEJ. If the ratio of HDR to NHEJ is high enough, HDR will continue. However, in the presence of NHEJ some of the DSBs formed by the enzyme 104 will rejoin without an insert.

NHEJ is consequently the principle means by which DSBs are repaired in natural cells. NHEJ-mediated repair is prone to generating indel errors. Indel errors generated in the course of repair by NHEJ are typically small (1-10 nt) but extremely heterogeneous. There is consequently about a two-thirds chance of causing a frameshift mutation. Thus, it may be desirable to minimize NHEJ and increase the probability that a DSB will be repaired by HDR. The likelihood of HDR being used may be improved by inhibiting components of the NHEJ process. Addition of small molecules such as NU7441 and KU-0060648 is one technique for inhibiting NHEJ through inhibition of DNA-dependent protein kinase, catalytic subunit ("DNA-PKcs"). Techniques for enhancing HDR efficiency in this way are described in Maruyama, et al., *Increasing the efficiency of precise genome editing with CRISPR-Cas9 by inhibition of nonhomologous end joining.* 33(5) Nature Biotechnology, 538 (2015) and Robert, et. al., *Pharmacological inhibition of DNA-PK stimulates Cas9-mediated genome editing.* 7 Genome Medicine 93 (2015). In an implementation, HDR efficiency may be improved by suppressing the molecules KU70, KU80, and/or DNA ligase IV, which are involved in the NHEJ pathway. In addition to the suppression, the Cas9 system, EB55K, and/or E4orf6 may be expressed to further increase HDR efficiency and reduce NHEJ activity. Techniques for enhancing HDR efficiency in this way are described in Chu et al., *Increasing the efficiency of homology-directed repair for CRISPR-Cas9-induced precise gene editing in mammalian cells.* 33(5) Nature Biotechnology, 543 (2015). Further, use of a single-stranded DNA oligo donor (ssODN) has been shown to improve the rate of HDR and knockin efficiency by up to 60% in Richardson et al., *Enhancing homology-directed genome editing by catalytically active and inactive CRISPR-Cas9 using asymmetric donor DNA,* 34(3) Nature Biotechnology 339 (2016).

Figure 2:
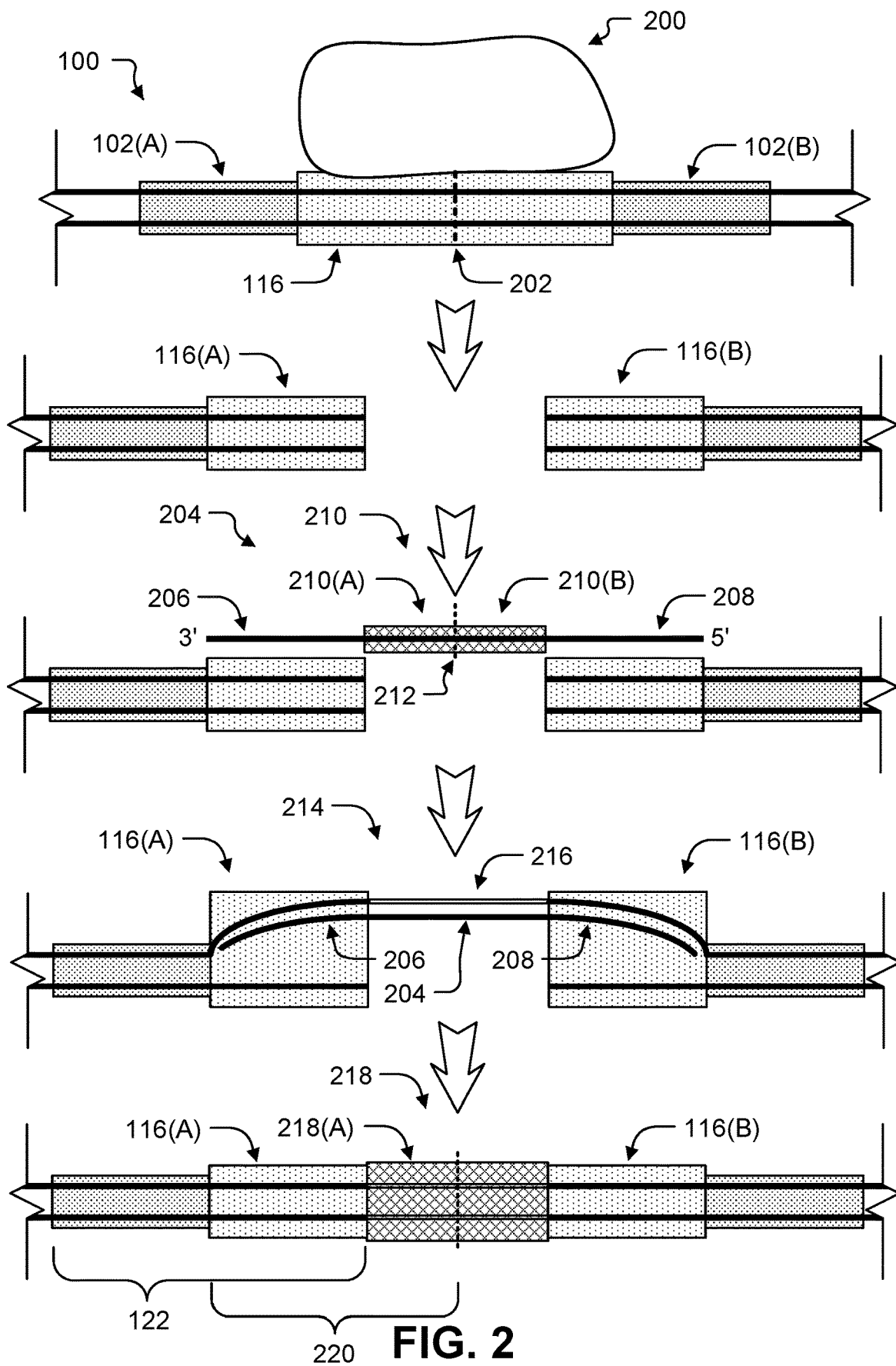
FIG. 2 shows a schematic representation of cutting the dsDNA of FIG. 1 and inserting additional DNA by HDR.

FIG. 2 shows schematic illustrations of further manipulations performed on the dsDNA 100 molecule of FIG. 1. A second enzyme 200 creates a second DSB at a second cut site 202 in the second target site 116. The second target site 116 has a different sequence than the first target site 102, and thus, the second enzyme 200 recognizes a different DNA sequence than the first enzyme 104. Creating a DSB in the second target site 116 at the cut site 202 creates the first subsequence 116(A) of the second target site 116 on one side of the cut site 202 and a second subsequence 116(B) of the second target site 116 on the other side of the cut site 202. In some implementations, the first subsequence 116(A) and the second subsequence 116(B) may have the same sequence. Thus, the first subsequence 116(A) and a second subsequence 116(B) may have the same nucleotide length. Also, if the first subsequence 116(A) and the second subsequence 116(B) are the same sequence, the second target site 116 may be thought of as having a single subsequence repeated once with a cut site 202 in the middle.

A second HDR template 204 contacts the dsDNA 100 to provide a template for HDR of the DSB. The second HDR template 204 includes a 3'-end region 206 that is homologous to one strand of the dsDNA 100 within the first subsequence 116(A) of the second target site 116. The second HDR template 204 also include a 5'-end region 208 that is homologous to one strand of the dsDNA 100 within the second subsequence 116(B) of the second target site 116. The second HDR template 204 also includes a portion in the middle 210 that encodes a third target site for a third enzyme. The middle region 210 includes a first subsequence 210(A) on one side of a third cut site 212 and a second subsequence 210(B) on other side of the third cut site 212.

Annealing of the second HDR template 204 to one strand of the dsDNA 100 creates a D loop 214 by hybridization of the 3'-end sequence 206 to the subsequence 116(A) and hybridization of the 5'-end sequence 208 to the subsequence 116(B). DNA polymerase and DNA ligase repair the strand of the dsDNA 100 to which the second HDR template 204 is hybridized by creating new DNA 216. The second strand of the dsDNA 100 is then repaired using the first strand as a template.

The dsDNA 100 now includes the third target site 218 inserted into the middle of the second target site 116 (which is itself inserted in the middle of the first target site 102). The order of the subsequence 116(A) followed by the subsequence 218(A) may create a record of a second combination of detected signals. Thus, the growing string of inserted DNA sequences can provide an ordered log of molecular events experienced by a cell. This process can repeat to record any number of molecular events.

Addition of HDR templates into existing DNA using the mechanisms described above may be regulated by signaling pathways as described in detail below. The encoding scheme described herein allows for insertion of DNA sequences representing an unbounded length. AN HDR template that does not include a cut site may be added once, end the process of HDR, and create a record that a specified signal was detected. The dsDNA in a cell may have multiple different target sites at different locations that include different cut sites and are homologous to different HDR templates. This provides for orthogonal recording of signals without any linkage between the signals. For example, a first target site may be configured to integrate a first HDR template if the cell is exposed to radiation, a second target site may be configured to integrate a second HDR template if the cell is exposed to hydrocarbons, and a third target site may be configured to integrate a third HDR template if the cell is exposed to light. Each cell configured in this way will create independent logs of the signals (e.g., radiation, hydrocarbons, and light) that it was exposed to. A cell may be modified to have any number of orthogonal target sites.

The three target sites may be represented as $X_1X_2$, $Y_1Y_2$, and $Z_1Z_2$. The first portion of the target site (e.g, $X_1$, $Y_1$, or $Z_1$) corresponds to subsequence 102(A) or subsequence 116(A) shown in FIG. 1. The remaining portion of the target site (e.g., $X_2$, $Y_2$, or $Z_2$) corresponds to subsequence 102(B) or subsequence 116(B) shown in FIG. 1. Thus, each X, Y, and Z represents a DNA sequence of about 5 to 20 nt such as, for example only, ACTGAA, GCCTCAT, TGACG, etc. In some implementations $X_1=X_2$, etc., but in other implementations the first portion of a target site may be different in sequence and/or length from the remaining portion of the target site.

The HDR templates all have end regions that are homologous to one of the target sites. Thus, the HDR templates will have sequences of the structure: $X_1aX_2$, $Y_1bY_2$, and $Z_1cZ_2$ where "a," "b," and "c" represent DNA sequences of the middle regions. Recall that the middle region of the HDR templates may itself encode a target site. Thus, for example, a may represent $X_1X_2$, b may represent $Z_1Z_2$, and c may represent a different target site $W_1W_2$. If the middle region does encode a target site, integration of an HDR template into dsDNA may be followed by further integration of the same or a different HDR template. Insertion of an HDR template into dsDNA that has been itself created by integration of an HDR template is referred to in this disclosure as "iterative integration."

Thus, a design using iterative integration of a single HDR template may record the presence of a signal and the length of the signal. For example, the HDR template may be XaXXaX and the initial insertion site may be XX. Iterative integration will result in a sequence that is represented by:

XXaXaXaXaX . . . XaXaXaXaXX

This sequence can keep growing continuously while the signal is detected. A potential problem is that the HDR templates may be cut by the same enzyme that creates a DSB at the insertion site because both include the sequence XX which is recognized by the enzyme used for this logging. Physical separation, splicing, self-excising elements, homologous bridges, or methylation may be used to prevent or decrease the amount of HDR templates that are cut before integration into the dsDNA.

In one configuration, the continued detection of multiple signals may be recorded by appropriately designed HDR templates and insertion sites. AN HDR template with a sequence XaYYaX is expressed when a first signal "a" is detected. Similarly, an HDR template YbXXbY is expressed when a second signal "b" is detected. Initially, the cell may include a target site XX or YY. If the cell only includes the target site XX, presence of signal "b" will not be recorded until the HDR template associated with signal "a" is first integrated into the DNA of the cell. As each HDR template provides the target site for the other, alternating exposure to signals "a" and "b" or continued exposure to both signals leads to continued integration of the HDR templates. This alternating, iterative addition will result in a sequence represented by:

XaYbXaYbX . . . XbYaXbYaX

This provides sequential recording of signals "a" and "b" independent of the relative concentrations of the HDR templates XaYYaX and YbXXbY. This technique for logging multiple signals at the same location in DNA may be expanded to cover three, four, or even more different signals.

In one configuration, multiple signals may be associated with HDR templates that have the same target sites. For example, a first signal "a" and a second signal "b" may be associated respectively with the HDR templates XaXXaX and XbXXbX. Either HDR template may be integrated into the target site XX. Once integrated, both HDR templates also include the target site XX allowing for iterative addition of either or both. In most conditions, the level of relative incorporation of the two HDR templates will be proportional to the relative concentrations of HDR templates. The amount of each HDR template present in the cell may be designed to be proportional to the strength, frequency, and/or duration of the corresponding signal. For example, if signal "a" is strong and constant the cell may produce a relatively large amount of the XaXXaX template. When signal "b" is present, the amount of the XbXXbX template may increase and then that HDR template is also integrated into the DNA of the cell. So long as all components are present, iterative insertion of these two templates depends on relative strengths of signals "a" and "b" and will result in a sequence represented by:

X[a|b]X[a|b]X . . . X[a|b]X[a|b]X
where [a|b] is a or b. The relative amount of "a" vs. "b" in the DNA provides a record of which signal was strongest and changes from a period of "a" dominance to a period of "b" dominance indicates a temporal change in the relative signal strengths. This configuration may be expanded to include three, four, or more different signals and HDR templates. Analysis of the DNA sequence created by this iterative and competitive integration of multiple HDR templates may be performed over defined lengths of nucleotides which represent periods of time. The lengths of nucleotides may be analyzed by considering a series of sliding windows (e.g., a 10,000 nt stretch of the DNA) and determining the relative level of Xa vs. Xb in a given window. This provides information about the relative strength of signals "a" and "b" during a given period of time.

One way of using this configuration is in a cell that has constitutive expression (rather than in response to a signal) of the first HDR template XaXXaX. This template will be expressed and present in the cell at a constant level. It may be thought of as a background signal. The level of the second HDR template XbXXbX will vary depending on the strength of signal "b." Thus, the amount of the XbXXbX template integrated into the DNA indicates the relative strength of signal "b" as compared to the baseline established by expression of XaXXaX.

Another way of using the configuration described above is to use the presence of one of the HDR templates in the DNA of the cell as a temporal indication like a time stamp. For example, the concentration of the first HDR template may respond to the detection of a signal. If the signal is continually present, then the HDR template XaXXaX will be iteratively introduced into the DNA of the cell. As described above, the length of the insertion will depend on the duration that the signal "a" is present. Intentionally exposing the cell to signal "b" at known time points provides references point in the DNA that can be correlated to the known times of exposure to signal "b." When exposed to signal "b," the expression of the second HDR template XbXXbX increases to a level greater than the expression of XaXXaX (e.g., the second HDR template may be regulated by a stronger promoter or present in more copies than the first HDR template). Thus, each point in the DNA that has an insertion of XbXbXb . . . indicates a time when the cell was exposed to "b" For example, if the cell is exposed to signal "b" every 24 hours, each string of DNA between XbXbXb . . . sequences represents the activity of signal "a" during that 24-hour period.

The above configurations may be combined to record multiple signals sequentially regardless of relative strength and also to record the strongest signal based on competing HDR templates. There may be multiple classes of HDR templates with each class having multiple different HDR templates transcribed in response to different signals. For example, there may be two classes of HDR templates XaYYaX and YbXXbY. Because these two HDR templates integrate into the target site created by addition of the other (i.e., the template that integrates into XX adds the target site YY and the template that integrates into YY adds the target site XX) they will alternate. Thus, the DNA will incorporate first an HDR template from the "a" class then an HDR template from the "b" class. Each class of HDR template includes two (but may include any number) HDR templates with partially different sequences that correspond to different signals. Thus, a signal "$a_1$" may cause increased expression of the HDR template $Xa_1YYa_1X$ and a signal "$a_2$" may cause increased expression of the HDR template $Xa_2YYa_2X$.

Similarly, a signal "$b_1$" may cause increased expression of the HDR template $Yb_1XXb_1Y$ and a signal "$b_2$" may cause increased expression of the HDR template $Yb_2XXb_2Y$. If the cell begins with DNA that includes the insertion site XX, then first one of the "a" HDR templates will be integrated based on the relative concentrations of the $Xa_1YYa_1X$ and of the $Xa_2YYa_2X$ HDR templates. Doing so creates a YY insertion site and is followed by integrating one of the "b" HDR templates again based on relative concentrations.

In one implementation, each class of the HDR template may record values associated with a particular type of molecular event. For example, the "a" class of HDR templates may indicate temperature experienced by the cell with $Xa_1YYa_1X$ expressed if the temperature is below 32° C. and $Xa_2YYa_2X$ expressed if the temperature is above 42° C. Thus, integration of the "a" class of HDR templates creates a record of relative temperature. The "b" class of HDR templates may be associated with a different type of signal such as salinity. The HDR template $Yb_1XXb_1Y$ may be expressed when the cell is in an environment with salinity below 0.600 M and $Yb_2XXb_2Y$ may be expressed when the cell is in an environment with salinity above 0.700 M. Thus, the record created in the DNA of this cell shows temperature high/low and salinity high/low. Each is recorded in turn so there is a log created over time showing changes in two different signals. Of course, any number of different gradations or levels of variables may be tracked by having distinct HDR templates under the control of appropriate promoter.

In one example implementation, using Cas9 as the nuclease with a PAM sequence of NNNNGATTT as the enzyme, three target sites may be:

$X_1$ = TAGCCGTATCGAGCATCGATG|CGCNNNNGATT = $X_2$ $Y_1$ = GATCGATGGACTCTGCATCTA|TCGNNNNGATT = $Y_2$ $Z_1$ = CGGGACGATCGATCGGGCTAG|ACTNNNNGATT = $Z_2$

Where the PAM sequence is indicated by bold, $X_1$ is (SEQ ID NO: 1), $X_2$ is (SEQ ID NO: 2), $Y_1$ is (SEQ ID NO: 3), $Y_2$ is (SEQ ID NO: 4), $Z_1$ is (SEQ ID NO: 5), and $Z_2$ is (SEQ ID NO: 6). Note that each of $X_1$, $Y_1$, and $Z_1$ are 21 nt long.

Each of the target sites is recognized by a corresponding guide ssDNA that cuts the dsDNA at the location indicated by the "^" below. They should have a trans-activating crRNA (tracrRNA) that is a small trans-encoded RNA for attaching to Cas9 appended to the end. The crRNAs are incorporated into effector complexes, where the crRNA guides the complex to the target site and the Cas proteins create a DSB in the polynucleotide. The respective ssDNA sequences are:

(SEQ ID NO: 1)
$gX_1$ = TAGCCGTATCGAGCATCGATG^CGC (SEQ ID NO: 3)
$gY_1$ = GATCGATGGACTCTGCATCTA^TCG (SEQ ID NO: 5)
$gZ_1$ = CGGGACGATCGATCGGGCTAG^ACT

Then a homology directed repair sequence of $X_1Y_1Y_2X_2$ is: TAGCCGTATCGAGCATCGATG|GATC-GATGGACTCTGCATCTA|TCGNNNNGAT-T|CGCNNNNGATT (SEQ ID NO: 7) and a homology directed repair sequence of $Y_1X_1X_2Y_2$ is: GATC-GATGGACTCTGCATCTA|TAGCCGTATCGAGCATC-GATG|CGCNNNNGATT|TCGNNNNGATT (SEQ ID NO:

8). Other homology directed repair sequences can be designed according to the same pattern.

An initial cut of the target site $X_1X_2$ will create a DSB that appears as (only one strand of the dsDNA is shown):

... TAGCCGTATCGAGCATCGATG CGCNNNNGATT ...

After HDR with $X_1Y_1Y_2X_2$, one strand of the dsDNA will have the following sequence that now includes the target site $Y_1Y_2$ indicated by italics:

(SEQ ID NO: 7)
TAGCCGTATCGAGCATCGATG|*GATCGATGGACTCTGCATCTA*||
TCGNNNNGATT|CGCNNNNGATT.

The dsDNA is now able to be cut by a Cas9 that has $Y_1$ creating a DSB at the location represented by "||". HDR may be performed with $Y_1X_1X_2Y_2$, for example, further adding to the dsDNA and completing another iteration of encoding. This may be continued with various sequences of cuts and HDR templates to record any series of molecular events.

Signaling Pathways

Figure 3:
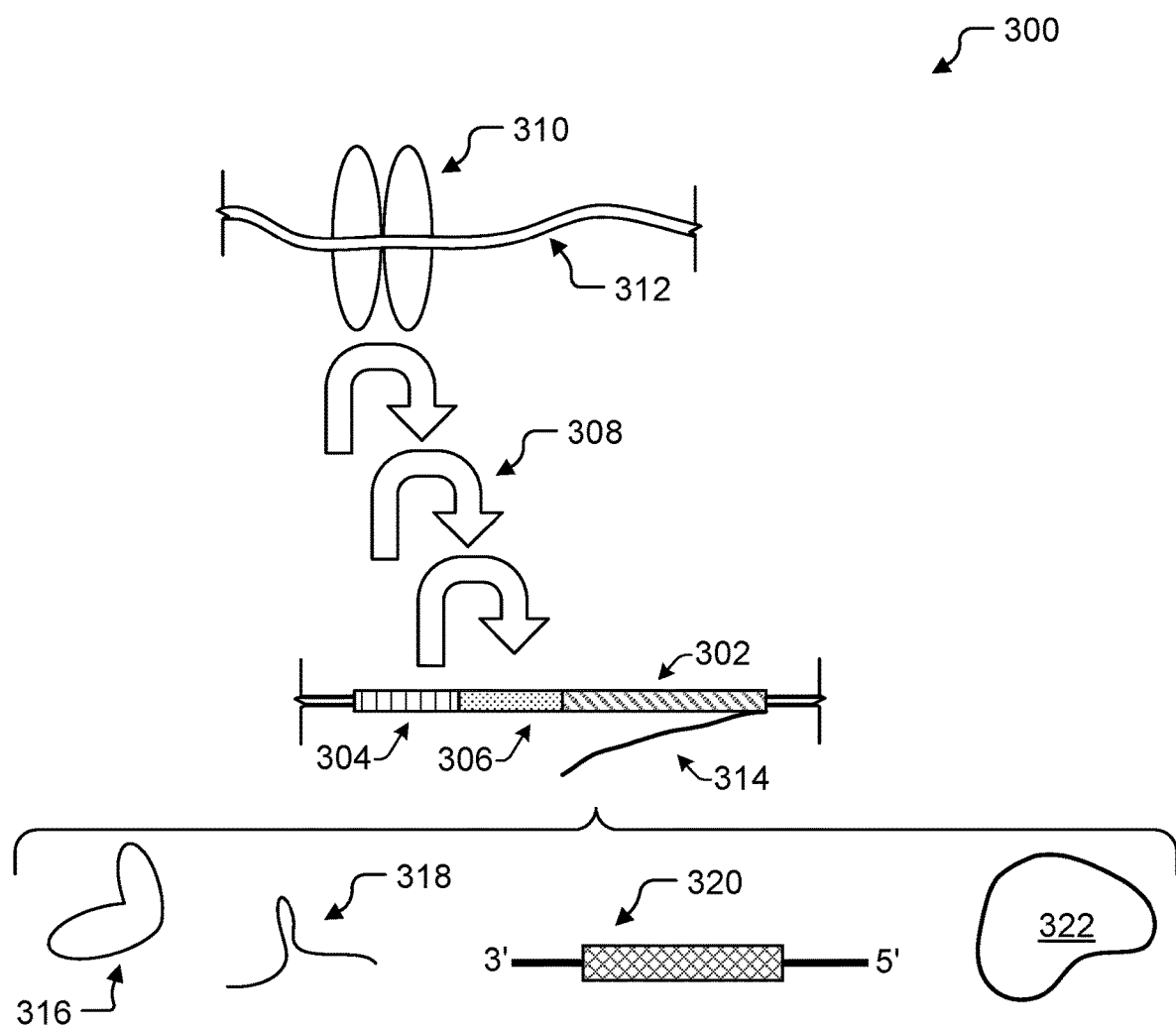
FIG. 3 shows illustrative components for controlling expression of a gene product based on a signaling pathway.

FIG. 3 shows a diagram 300 of an illustrative signaling pathway that regulates expression of a gene. The signaling pathway may be an engineered signaling pathway that is created or modified in some way to be different from a wild-type signaling pathway. The signaling pathway controls the expression of a gene 302 that is under the control of a promoter 304 and may also be under the control of an operator 306. A promoter is a region of DNA that initiates transcription of a particular gene. Promoters are located near the transcription start sites of genes, on the same strand and upstream on the DNA (towards the 5' region of the sense strand). Illustrative promoters are described below. The sequence of the promoter region controls the binding of the RNA polymerase and transcription factors. An operator is a segment of DNA to which a repressor binds to decrease or stop gene expression. A "transcription factor" is a protein that binds near the beginning of the coding sequence (transcription start site) for a gene or functional mRNA. Transcription factors are necessary for recruiting DNA polymerase to transcribe DNA. A transcription factor can function as a repressor, which can bind to the operator to prevent transcription. The gene 302, the promoter 304, and the operator 306 are on a dsDNA molecule that may be genomic DNA of a cell or other DNA such as a plasmid or vector. In some implementations, the promoter 304 may respond to signals such as temperature or pH and thus the promotor 304 itself may be the signaling pathway.

The repressor (and/or "knockdown") may be a protein or mRNA (small hairpin loops (shRNA), interfering mRNA (RNAi or siRNA)) that binds to DNA/RNA and blocks either attachment of the promoter, blocks elongation of the polymerase during transcription, or blocks mRNA from translation. In addition to repressors, the CRISPR/Cas9 system itself may be used for sequence-specific repression of gene expression in prokaryotic and eukaryotic cells. Specifically, the technique of CRISPR interference (CRISPRi) uses catalytically dead Cas9 lacking endonuclease activity to regulate genes in an RNA-guided manner. Catalytically inactive Cas9 may be created by introducing point mutations into the Cas9 protein such as at the two catalytic residues (D10A and H840A) of the gene encoding Cas9. In doing so, dCas9 is unable to cleave dsDNA but retains the ability to target DNA. Targeting specificity for CRISPRi is determined by complementary base pairing of a guide RNA (gRNA) to the genomic loci. The gRNA may be designed to target a specific promoter. The complex catalytically dead Cas9 and the gRNA will block activation of the promoter and turn off expression of any gene regulated by that promoter.

The signaling pathway may include a signaling cascade 308 that carries a signal from a first messenger (i.e., the initial signal) and eventually results in activation, or alternatively suppression, of either the promoter 304 or the operator 306. The initial signal that sets the signaling cascade 308 into action may be an internal or external signal. The signaling pathway may be a trans-membrane signaling pathway that includes an external receptor 310 which detects extracellular signals and communicates the signal across a membrane 312. The membrane 312 may be a cell wall, lipid bilayer, artificial cell wall, or synthetic membrane.

In one implementation, the external receptor 310 may be a G protein-coupled receptor (GPCR). GPCRs constitute a large protein family of receptors, that sense molecules outside the membrane 312 and activate the signaling cascade 308 and, ultimately, cellular responses. The GPCR is activated by an external signal in the form of a ligand or other signal mediator. This creates a conformational change in the GPCR, causing activation of a G protein. Further effect depends on the type of G protein. G proteins are subsequently inactivated by GTPase activating proteins, known as RGS proteins. The ligands that bind and activate these GPCRs include light-sensitive compounds, odors, pheromones, hormones, neurotransmitters, etc. and vary in size from small molecules to peptides to large proteins. When a ligand binds to the GPCR it causes a conformational change in the GPCR, which allows it to act as a guanine nucleotide exchange factor (GEF). The GPCR can then activate an associated G protein by exchanging its bound GDP for a GTP. The G protein's a subunit, together with the bound GTP, can then dissociate from the β and γ subunits to further affect intracellular signaling proteins or target functional proteins directly depending on the a subunit type.

In one implementation, the external receptor 310 may be a photosensitive membrane protein. Photoreceptor proteins are light-sensitive proteins involved in the sensing and response to light in a variety of organisms. Photoreceptor proteins typically consist of a protein moiety and a non-protein photopigment that reacts to light via photoisomerization or photoreduction, thus initiating a change of the receptor protein that triggers the signaling cascade 308. Pigments found in photoreceptors include retinal (retinylidene proteins, for example rhodopsin in animals), flavin (flavoproteins, for example cryptochrome in plants and animals) and bilin (biliproteins, for example phytochrome in plants). One example of engineered use of light-sensitive proteins is found in Tamsir, A. et al., *Robust Multicellular Computing Using Genetically Encoded NOR Gates and Chemical 'Wires'*, 469 Nature 214 (2011).

The external receptor 310, in some implementations, may also be a membrane-bound immunoglobulin (mIg). A membrane-bound immunoglobulin is the membrane-bound form of an antibody. Membrane-bound immunoglobulins are composed of surface-bound IgD or IgM antibodies and associated Ig-α and Ig-β heterodimers, which are capable of signal transduction through the signaling cascade 308 in response to activation by an antigen.

In one implementation, the external receptor 310 may be a Notch protein. The Notch protein spans the cell membrane, with part of it inside and part outside. Ligand proteins binding to the extracellular domain induce proteolytic cleavage and release of the intracellular domain, which enters the cell to modify gene expression. The receptor may be triggered via direct cell-to-cell contact, in which the transmembrane proteins of the cells in direct contact form the ligands that bind the notch receptor. Signals generated by the Notch protein may be carried to an operon by the Notch cascade which consists of Notch and Notch ligands as well as intracellular proteins transmitting the notch signal.

In one implementation, temperature may activate the signaling pathway. Thus, by altering the temperature, expression of the gene 302 may be up or down regulated. Temperature sensing molecules that occur naturally in single celled organisms include heat shock proteins and certain RNA regulatory molecules, such as riboswitches. Heat shock proteins are proteins that are involved in the cellular response to stress. One example of a heat shock protein that responds to temperature is the bacterial protein DnaK. Temperatures elevated above normal physiological range can cause DnaK expression to become up-regulated. DnaK and other heat shock proteins can be utilized for engineered pathways that respond to temperature. Riboswitches are a type of RNA molecule that can respond to temperature in order to regulate protein translation. An example of a temperature-regulated engineered pathway that has utilized a riboswitch can be found in Neupert, J. et al., *Design of simple synthetic RNA thermometers for temperature-controlled gene expression in Escherichia coli,* 36(19) Nucleic Acids Res., e124, (2008). Another example of a temperature-sensitive molecule that can be utilized to regulate engineered cell pathways is a temperature-sensitive mutant protein. Single mutations can be made to proteins, which cause the proteins to become unstable at high temperatures, yet remain functional at lower temperatures. Methods for synthesizing temperature-sensitive mutant proteins can be found in Ben-Aroya, S. et al., *Making Temperature-Sensitive Mutants,* 470 Methods Enzymology 181 (2010). An example of a temperature-controlled engineered pathway that utilizes a temperature-sensitive mutant can be found in Hussain, F. et al., *Engineered temperature compensation in a synthetic genetic clock,* 111(3) PNAS 972 (2014).

In one implementation, ion concentration or pH may activate the signaling pathway. With signaling pathways of this type, placing a cell in a different ionic environment or altering pH surrounding the cell may be used to control the availability of a given HDR template or enzyme. Examples of cellular sensing molecular mechanisms that detect ionic strength or pH include many viral proteins, such as herpes simplex virus gB, rubella virus envelope protein, influenza hemagglutinin, and vesicular stomatitis virus glycoprotein. An example of a natural cellular pathway that is regulated by pH is penicillin production by *Aspergillus nidulans* as described in Espeso, E. et al., *pH Regulation is a Major Determinant in Expression of a Fungal Penicillin Biosynthetic Gene,* 12(10) EMBO J. 3947 (1993). Another example of a pH-sensitive molecule that can be utilized to regulate engineered cell pathways is a pH-sensitive mutant protein. Single mutations can be made to proteins, which can cause the proteins to become less stable in either acidic or basic conditions. For example, pH-sensitive antibodies can bind to an antigen at an optimal pH, but are unable to bind to an antigen at a non-optimal pH. A technique for creating pH-sensitive antibodies that can be used for engineered signaling pathways can be found in Schroter, C. et al., *A generic approach to engineer antibody pH-switches using combinatorial histidine scanning libraries and yeast display,* 7(1) MAbs 138 (2015). These and other similar sensing mechanisms may be engineered to affect the behavior of a promoter 304 or operator 306.

The gene 302 encodes for gene product 314 that may ultimately be the basis for a number of components in an HDR system. For example, the gene product 314 may be translated into protein, used directly as RNA, or reverse transcribed into DNA. In one implementation, the gene product 314 may be translated into a nuclease 316 that creates DSBs such as, for example, enzyme 104 shown in FIG. 1, or enzyme 200 shown in FIG. 2. The nuclease 316 may be a Cas enzyme such as Cas9, Cas1, or Cas2.

For example, the *S. pyogenes* Cas9 system from the Clustered Regularly-Interspaced Short Palindromic Repeats-associated (CRISPR-Cas) family is an effective genome engineering enzyme that catalyzes double-stranded breaks and generates mutations at DNA loci targeted by a gRNA. The native gRNA is comprised of a 20 nucleotide (nt) Specificity Determining Sequence (SDS), which specifies the DNA sequence to be targeted, and is immediately followed by a 80 nt scaffold sequence, which associates the gRNA with Cas9. In addition to sequence homology with the SDS, targeted DNA sequences possess a Protospacer Adjacent Motif (PAM) (5'-NGG-3') immediately adjacent to their 3'-end in order to be bound by the Cas9-sgRNA complex and cleaved. When a double-stranded break is introduced in the target DNA locus in the genome, the break is repaired by either homologous recombination (when a repair template is provided) or error-prone non-homologous end joining (NHEJ) DNA repair mechanisms, resulting in mutagenesis of targeted locus. Even though the normal DNA locus encoding the gRNA sequence is perfectly homologous to the gRNA, it is not targeted by the standard Cas9-gRNA complex because it does not contain a PAM.

In a wild-type CRISPR/Cas system, gRNA is encoded genomically or episomally (e.g., on a plasmid). Following transcription, the gRNA forms a complex with Cas9 endonuclease. This complex is then "guided" by the specificity determining sequence (SDS) of the gRNA to a DNA target sequence, typically located in the genome of a cell. For Cas9 to successfully bind to the DNA target sequence, a region of the target sequence must be complementary to the SDS of the gRNA sequence and must be immediately followed by the correct protospacer adjacent motif (PAM) sequence (e.g. "NGG"). Thus, in a wild-type CRISPR/Cas9 system, the PAM sequence is present in the DNA target sequence but not in the gRNA sequence (or in the sequence encoding the gRNA).

The PAM sequence is typically a sequence of nucleotides located adjacent to (e.g., within 10, 9, 8, 7, 6, 5, 4, 3, 3, or 1 nucleotide(s) of) an SDS sequence). A PAM sequence is "immediately adjacent to" an SDS sequence if the PAM sequence is contiguous with the SDS sequence (that is, if there are no nucleotides located between the PAM sequence and the SDS sequence). In some implementations, a PAM sequence is a wild-type PAM sequence. Examples of PAM sequences include, without limitation, NGG, NGR, NNGRR (T/N), NNNNGATT, NNAGAAW, NGGAG, and NAAAAC, AWG, CC. In some implementations, a PAM sequence is obtained from *Streptococcus pyogenes* (e.g., NGG or NGR). In some implementations, a PAM sequence is obtained from *Staphylococcus aureus* (e.g., NNGRR(T/N)). In some implementations, a PAM sequence is obtained from *Neisseria meningitidis* (e.g., NNNNGATT). In some implementations, a PAM sequence is obtained from *Streptococcus thermophilus* (e.g., NNAGAAW or NGGAG). In some implementations, a PAM sequence is obtained from *Treponema denticola* NGGAG (e.g., NAAAAC). In some implementations, a PAM sequence is obtained from *Escherichia coli* (e.g., AWG). In some implementations, a PAM sequence is obtained from *Pseudomonas auruginosa* (e.g., CC). Other PAM sequences are contemplated. A PAM sequence is typically located downstream (i.e., 3') from the SDS, although in some embodiments a PAM sequence may be located upstream (i.e., 5') from the SDS.

In one implementation, the gene product 314 encodes for gRNA 318 that is used by the Cas enzyme 316 to target a specific DNA sequence. The system may be designed to have all components needed for performing HDR other than the gRNA 318. Thus, transcription of the gRNA in response to a signal provides the last component needed to perform HDR and results in incorporation of an HDR template thereby creating a log of the molecular event. Alternatively, the gRNA 318 may be used not to cut dsDNA but to turn off a promoter through use of CRISPRi guide RNA. CRISPRi guide RNA directs the Cas enzyme 316 to bind to the promoter 304 and prevent transcription of the gene 302. In this design, the presence of a signal would stop the insertion of a particular HDR template.

A gRNA is a component of the CRISPR/Cas system. A "gRNA" (guide ribonucleic acid) herein refers to a fusion of a CRISPR-targeting RNA (crRNA) and a trans-activation crRNA (tracrRNA), providing both targeting specificity and scaffolding/binding ability for Cas9 nuclease. A "crRNA" is a bacterial RNA that confers target specificity and requires tracrRNA to bind to Cas9. A "tracrRNA" is a bacterial RNA that links the crRNA to the Cas9 nuclease and typically can bind any crRNA. The sequence specificity of a Cas DNA-binding protein is determined by gRNAs, which have nucleotide base-pairing complementarity to target DNA sequences. Thus, Cas proteins are "guided" by gRNAs to target DNA sequences. The nucleotide base-pairing complementarity of gRNAs enables, in some embodiments, simple and flexible programming of Cas binding. Nucleotide base-pair complementarity refers to distinct interactions between adenine and thymine (DNA) or uracil (RNA), and between guanine and cytosine. In some embodiments, a gRNA is referred to as a stgRNA. A "stgRNA" is a gRNA that complexes with Cas9 and guides the stgRNA/Cas9 complex to the template DNA from which the stgRNA was transcribed.

The length of a gRNA may vary. In some embodiments, a gRNA has a length of 20 nucleotides to 200 nucleotides, or more. For example, a gRNA may have a length of 20 to 175, 20 to 150, 20 to 100, 20 to 95, 20 to 90, 20 to 85, 20 to 80, 20 to 75, 20 to 70, 20 to 65, 20 to 60, 20 to 55, 20 to 50, 20 to 45, 20 to 40, 20 to 35, or 20 to 30 nt.

In one implementation, the gene product 314 may itself be or may encode for an HDR template 320. The HDR template 320 may be, for example, the HDR template 108 shown FIG. 1 or the HDR template 204 shown in FIG. 2. The gene product 314, although it is a ssRNA, may be capable of functioning as an HDR template 320 due to the ability of RNA to hybridize with DNA. RNA transcript-mediated HDR has been shown to function successfully in eukaryotic cells. See Keskin, H. et al., *Transcript-RNA-templated DNA recombination and repair,* 515 Nature 436 (2014) and Storici. F. et al., *RNA-templated DNA repair,* 447 Nature 338 (2007). If RNA is used as the HDR template, the cell may be further modified to reduce or remove enzymes that degrade RNA-DNA hybrids. In one implementation, the cell using RNA as the HDR template may be *S. cerevisiae*. Additionally, complementary DNA (cDNA), resulting from reverse-transcription of mRNA, and/or transcript RNA itself may aid DSB repair via HDR. Moreover, splicing of both expressed RNA and potentially of mRNA can change the sequence of RNA that serves as a template for reverse transcriptase to synthesize cDNA. Thus, the cDNA used as an HDR template may have a different sequence, due to splicing, than genomic or other DNA encoding the initial RNA transcript. The gene product 314 may also be converted to ssDNA by reverse transcriptase and used as the HDR template 320 in the form of DNA.

The gene product 314 may also be translated into some other enzyme product 322. The other enzyme product 322 represents another enzyme that may be used for logging of molecular events through HDR. Both DNA Taq polymerase and DNA ligase are examples of other enzyme products used for performing HDR. In a system that lacks one or both of these enzymes, regulated addition through control of gene expression is a way to regulate the ability to perform HDR. Other enzymes such as transcription factors are another type of other enzyme products 322. Transcription factors expressed from a first gene may be used to activate the promoter or operator of a second gene. There may be greater need for addition of other enzyme products 322 in a cell-free system or in a minimal cell than in a biological cell that includes wild-type cellular machinery.

Figure 4:
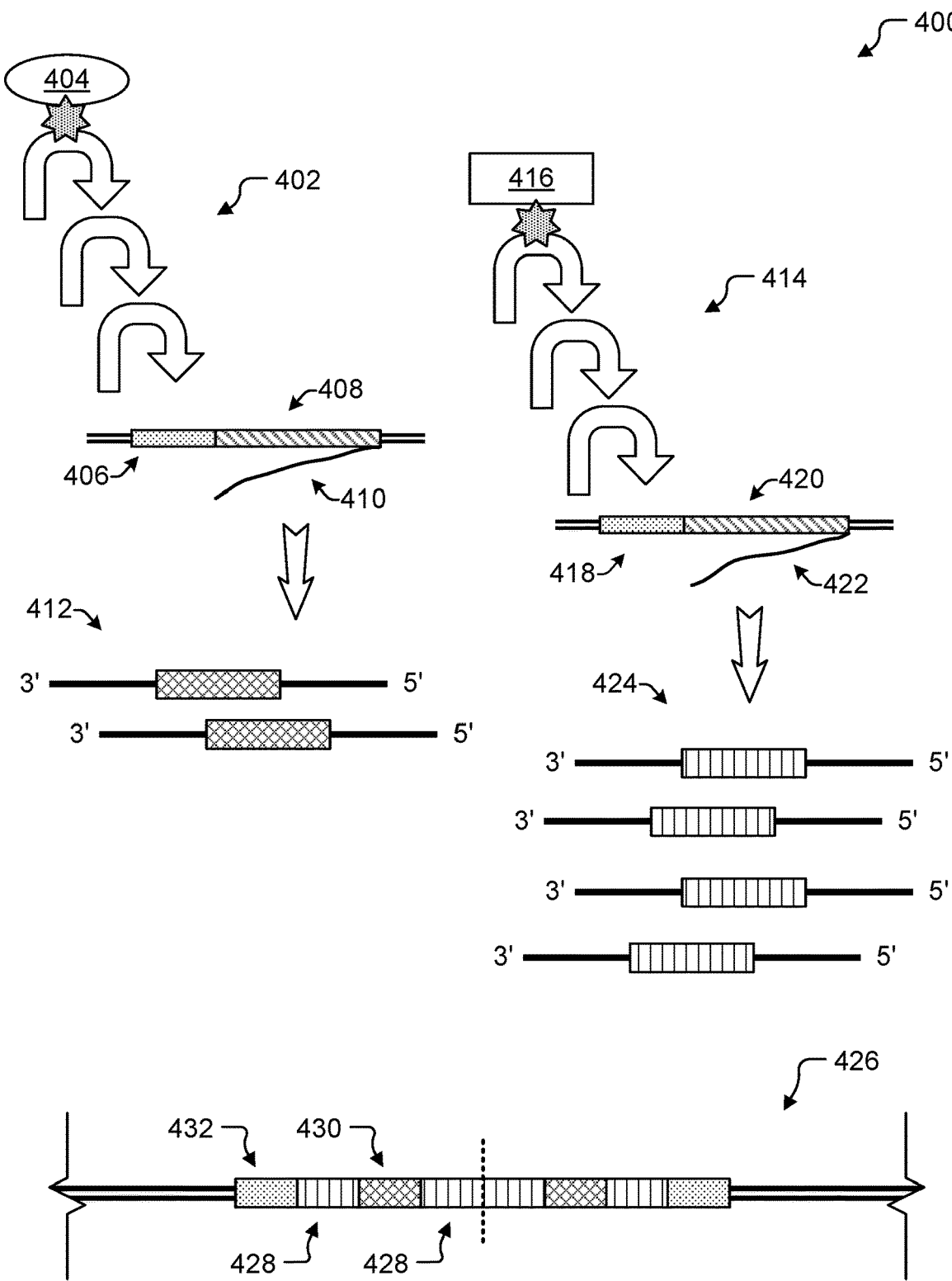
FIG. 4 shows illustrative components for creating a log of multiple signals in a way that records relative signal strength.

FIG. 4 shows a diagram 400 of two illustrative signaling pathways that create different gene products at levels responsive to strengths of the respective signals. A first signaling pathway 402 responds to a first signal 404 by increasing activity of a first promoter 406 which controls transcription of a first gene 408. The first signaling pathway 402 and the first signal 404 may be any of the signaling pathways or types of signals discussed in this disclosure. The first gene 408 creates a first gene product 410 that may be any of the types of gene products shown in FIG. 3. For purposes of illustration, the first gene product 410 is shown as encoding a first homology repair template 412. Thus, an increase in the first signal 404 leads to an increase in the synthesis of the first homology repair template 412.

Similarly, a second signaling pathway 414 is responsive to a second signal 416 by increasing activity of a second promoter 418 which controls transcription of a second gene 420. The second gene 420 encodes a second gene product 422. The second gene product 422 may be any of the types of gene products discussed in FIG. 3. The second gene product 422 may be the same or a different type of gene product than the first gene product 410. In this diagram 400, the second gene product 422 is shown as a second homology repair template 424. The amount of the second homology repair template 424 is thus regulated by the strength of the second signal 416.

If, for example, the second signal 416 is stronger and/or more frequent than the first signal 404, the cell will create a greater number of copies of the second homology repair template 424 than of the first homology repair template 412. The respective signaling pathways 402, 414 and the promoters 406, 418 may be selected to maintain a similar ratio of correspondence between respective signal strengths and synthesis of homology repair templates 412, 424. For example, the respective signaling pathways 402, 414 may be the same except for the portion of the signaling pathway directly involved in sensing the primary signal. The promoters 406, 418 may also be similar and different only in one aspect such as the specific transcription factor used to activate the promoter.

In this example, the second homology repair template 424 is present at a concentration that is twice as much as the first homology repair template 412. This indicates that the second signal 416 is approximately twice as strong as the first signal 404. Because the concentration of the second HDR template 424 is twice that of the first HDR template 412, for each HDR event it is twice as likely that the second homology repair template 424 will be integrated into a section of dsDNA 426. Thus, over a prolonged period of iterative integration of homology repair templates, it is likely that a sequence 428 from the second homology repair template 424 will be twice as common as a sequence 430 from the first homology repair template 412. The dsDNA 426 may include, for example, a target site 432 into which either the first homology repair template 412 or the second homology repair template 424 may be inserted. The relative amount of integration of the sequence 428 from the second homology repair template 424 and the sequence 430 of the first homology repair template 412 into the dsDNA 426 reflects the relative concentrations of the first homology repair template 412 and the second homology repair template 424. Specifically, in this example, the sequence 428 of the second homology repair template 424 is present twice as often as the sequence 430 from the first homology repair template 412. Thus, the first HDR template 412 and the second HDR template 424 integrate into the dsDNA 426 in proportion to their respective concentrations.

If the strength of one or more of signals 404, 416 in this example system changes over time then the relative concentrations of the corresponding HDR templates 412, 424 will also change. This change over time may be observed by analyzing the sequence of the dsDNA 426 and observing throughout different portions of that sequence how the ratio of the sequence 428 of the second homology repair template 424 to the sequence 430 of the first homology repair template 412 varies. This temporal analysis may be implemented, for example, by analyzing a sliding window of nucleotides of the dsDNA 426 and counting the number of times the sequence 428 from the second homology repair template 424 is found and the number of times the sequence 430 of the first homology repair template 412 is found. The sliding window may be any length such as, for example 500 nt, 1000 nt, 5000 nt, etc.

Figure 5:
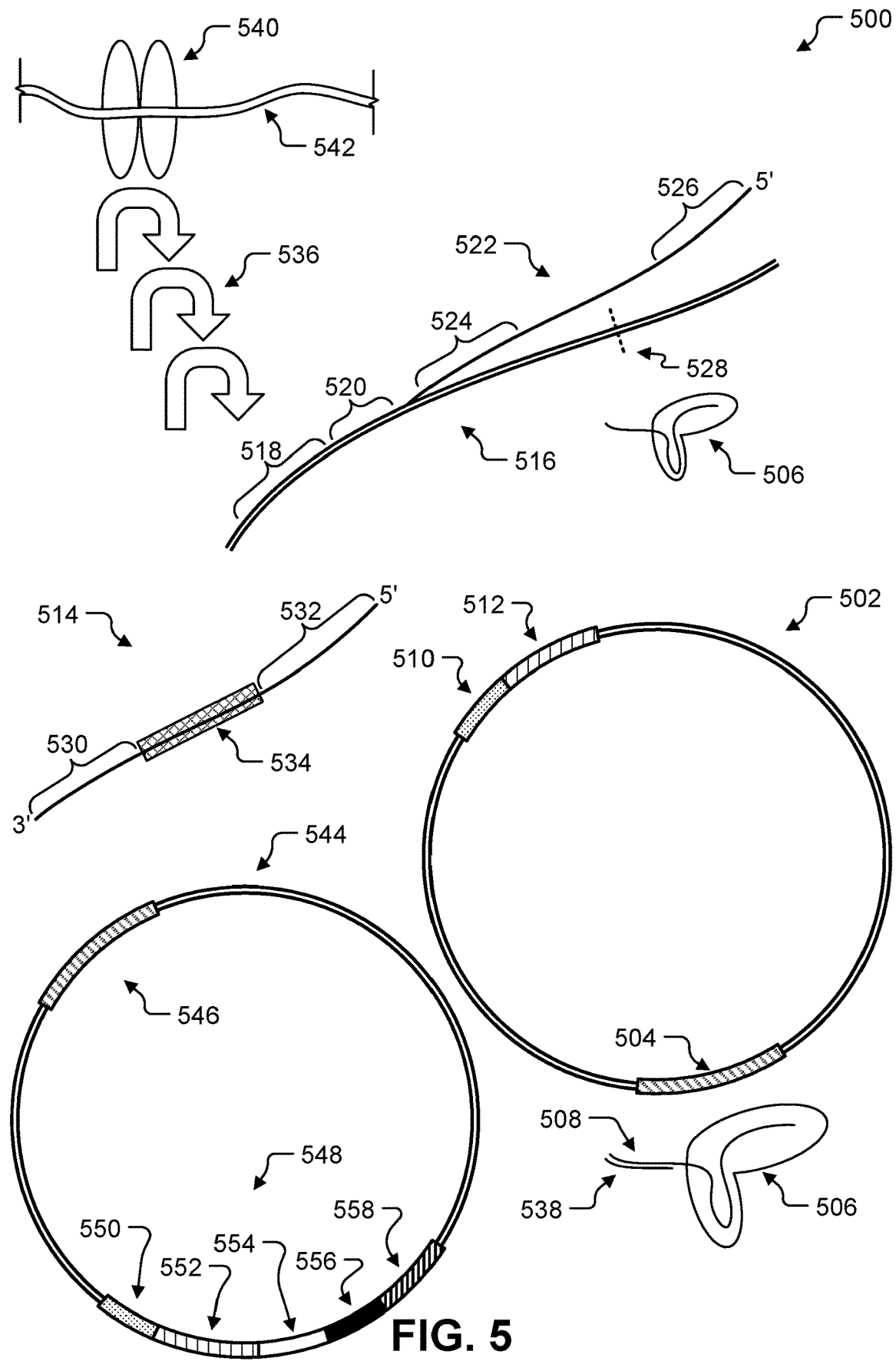
FIG. 5 show illustrative components of a cell for inserting new DNA into existing dsDNA.

FIG. 5 shows an illustrative cell 500 that is capable of heritability storing a log of events experienced by the cell 500. The cell 500 may be an *E. coli* cell, a *Saccharomyces cerevisiae* cell, or a cell from another single-celled organism. It may also be a cell from a multi-cellular organism grown in culture. Some human cell lines that may be used for cell culture include DU145, H295R, HeLa, KBM-7, LNCaP, MCF-7, MDA-MB-468, PC3, SaOS-2, SH-SY5Y, T47D, THP-1, U87, and National Cancer Institute's 60 cancer cell line panel (NCI60).

The cell 500 may contain a dsDNA molecule 502 that has a first target site 504. The cell 500 may also contain a first enzyme 506 that is configured to create a DSB at a cut site within the first target site 504. For example, the first enzyme 506 may be a CRISPR/Cas system comprising a gRNA 508 that includes a spacer region (also called a proto-spacer element or targeting sequence) of about 20 nt that is complementary to one strand of the dsDNA 502 at the first target site 504.

The dsDNA molecule 502 may also include a promoter 510 and a gene encoding a homology repair template 512 such as homology repair template 514 shown in this figure.

The dsDNA molecule 502 may be a vector or plasmid introduced to the cell 500 by any suitable method. A "vector" is a polynucleotide molecule, such as a DNA molecule derived, for example, from a plasmid, bacteriophage, yeast or virus, into which a polynucleotide can be inserted or cloned. One type of vector is a "plasmid," which refers to a circular double-stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, lentiviruses, replicative defective lentiviruses, adenoviruses, replication defective adenoviruses, and adeno-associated viruses). Viral vectors also include polynucleotides carried by a virus for transfection into a host cell. Moreover, certain vectors are capable of directing the expression of genes to which they are operatively-linked. Such vectors are referred to herein as "expression vectors." Common expression vectors of utility in recombinant DNA techniques are often in the form of plasmids. Plasmids suitable for expressing embodiments of the present invention, methods for inserting nucleic acid sequences into a plasmid, and methods for delivering recombinant plasmids to cells of interest are known in the art.

A vector may contain one or more unique restriction sites and can be capable of autonomous replication in a defined host cell including a target cell or tissue or a progenitor cell or tissue thereof (e.g. bacterial vectors having a bacterial origin of replication and episomal mammalian vectors), or be integrable with the genome of the defined host such that the cloned sequence is reproducible (e.g., non-episomal mammalian vectors). Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

Several aspects of the invention relate to vector systems comprising one or more vectors, or vectors as such. Vectors can be designed for expression of transcripts (e.g. nucleic acid transcripts, proteins, or enzymes) in prokaryotic or eukaryotic cells. For example, transcripts can be expressed in bacterial cells such as *Escherichia coli*, insect cells (using baculovirus expression vectors), yeast cells, or mammalian cells. Suitable host cells are discussed further in Goeddel, *Gene Expression Technology: Methods In Enzymology*, 185, Academic Press. San Diego, Calif. (1990). Alternatively, the recombinant expression vector can be transcribed and translated in vitro, for example using T7 promoter regulatory sequences and T7 polymerase.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). Expression of proteins in prokaryotes is most often carried out in *E. coli* with vectors containing constitutive or inducible promoters directing the expression of proteins. Examples of suitable inducible *E. coli* expression vectors include pTrc (Amrann et al., (1988) Gene 69:301-315) and pET 11d (Studier et al., *Gene Expression Technology: Methods In Enzymology* 185, Academic Press, San Diego, Calif. (1990) 60-89).

In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). For other suitable expression systems for both prokaryotic and eukaryotic cells see, e.g., Chapters 16 and 17 of Sambrook, et al., *Molecular Cloning: A Laboratory Manual.* 2nd ed., Cold Spring Harbor Laboratory, Cold Spring Harbor Laboratory Press, Cold Spring Harbor, N.Y., 1989.

Appropriate DNA segments may be inserted into a vector by a variety of procedures. In general, DNA sequences may be inserted into an appropriate restriction endonuclease site(s) by procedures known in the art, which may be performed without undue experimentation by a skilled artisan. A DNA segment in an expression vector may be operatively linked to an appropriate expression control sequence(s) (i.e., a promoter such as 510) to direct synthesis. As used herein, a "promoter" is a DNA regulatory region capable of binding RNA polymerase and initiating transcription of a downstream (3' direction) coding or non-coding sequence. For purposes of defining the present invention, the promoter sequence is bounded at its 3' terminus by the transcription initiation site and extends upstream (5'direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention. A promoter may also contain sub-regions at which regulatory proteins and molecules may bind, such as RNA polymerase and other transcription factors. Promoters may be constitutive, inducible, activatable, repressible, tissue-specific or any combination thereof.

Promoters may include any promoter known in the art for expression either in vivo or in vitro. Promoters which may be used in embodiments of the present invention may include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). The promoters which may be used in embodiments of the present invention may also be inducible, such that expression may be decreased or enhanced or turned "on" or "off." For example, promoters which respond to a particular signal (e.g., small molecule, metabolite, protein, molecular modification, ion concentration change, electric charge change, action potential, radiation, UV, and light) may also be used. Additionally, a tetracycline-regulatable system employing any promoter such as, but not limited to, the U6 promoter or the H1 promoter, may be used. By way of example and not of limitation, promoters which respond to a particular stimulus may include, e.g., heat shock protein promoters, and Tet-off and Tet-on promoters.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

A promoter drives expression or drives transcription of the nucleic acid sequence that it regulates. Herein, a promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter is referred to as an "endogenous promoter."

In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/ or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR). Contemplated herein, in some embodiments, are RNA pol II and RNA pol III promoters. Promoters that direct accurate initiation of transcription by an RNA polymerase II are referred to as RNA pol II promoters. Examples of RNA pol II promoters for use in accordance with the present disclosure include, without limitation, human cytomegalovirus promoters, human ubiquitin promoters, human histone H2A1 promoters and human inflammatory chemokine CXCL 1 promoters. Other RNA pol II promoters are also contemplated herein. Promoters that direct accurate initiation of transcription by an RNA polymerase III are referred to as RNA pol III promoters. Examples of RNA pol III promoters for use in accordance with the present disclosure include, without limitation, a U6 promoter, a HI promoter and promoters of transfer RNAs, 5S ribosomal RNA (rRNA), and the signal recognition particle 7SL RNA.

Illustrative promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc. Cells, such as cells in culture, may be transfected or transformed with the dsDNA molecule 502. Transfection is the process of deliberately introducing naked or purified polynucleotides into eukaryotic animal cells. Transformation refers to DNA transfer in bacteria and non-animal eukaryotic cells, including plant cells. Transfection may be performed using viruses or mechanical methods. Viral transfection introduces foreign DNA into a cell by a virus or viral vector. Transfection with a virus may introduce the DNA into the genome of the host cell. Mechanical transfection typically involves opening transient pores or "holes" in the cell membrane to allow the uptake of material. Transfection can be carried out using calcium phosphate (i.e. tricalcium phosphate), by electroporation, microinjection, gene gun, impalefection, hydrostatic pressure, continuous infusion, sonication, lipofection, nanoparticles containing the dsDNA molecule 502 (e.g., mesoporous silica nanoparticles or gold nanoparticles) or by mixing a cationic lipid with the material to produce liposomes which fuse with the cell membrane and deposit their cargo inside. Nanoparticles used to introduce foreign DNA may be ionically charged or have targeting ligands to deliver to specific cells or sites.

One viral transfection technique for transferring genetic material to hard-to-transfect cells is recombinant adeno-associated virus (AAV) delivery. This is a type of viral transduction that does not integrate into the host genome. AAV-based systems have been used successfully to introduce the gene for *S. pyogenes* Cas9 (SpCas9) together with its optimal promoter and polyadenylation signal using the AAVpro CRISPR/Cas9 Helper Free System (AAV2) available from Takara Bio USA, Inc.

Conjugation may also be used to introduce the dsDNA molecule 502 into a cell. Although conjugation in nature occurs more frequently in bacteria, transfer of genetic material from bacterial to mammalian cells is also possible. See Waters V. L., *Conjugation between bacterial and mammalian cells.* 29 (4) Nature Genetics 375 (2001).

The cell 500 may also include a gene 516 under the control of a promoter 518 and an operator 520. The gene 516 may encode a ssRNA sequence 522 comprising a 3'-end sequence 524 and a 5'-end sequence 526. AN HDR template 514 may be generated from the gene 516. In one implementation, the HDR template 514 is the ssRNA sequence 522 itself. The 3'-end sequence 524 and the 5'-end sequence 526 are complementary to one strand of a dsDNA molecule 502 over at least part of a target site 504. Homology between the 3'-end sequence 524 and the 5'-end sequence 526 allows the ssRNA sequence 522 to hybridize with portions of the dsDNA on either side of a DSB created at a cut site in the target site 504.

In implementations in which the gene 516 directly encodes the HDR template 514, the gene 516 will encode a cut site 528 that may be cut by an enzyme such as the first enzyme 506. Unless protected from the enzyme, the cut site 528 in the gene 516 may be unintentionally cut when the enzyme contacts the gene 516.

One technique for protecting the cut site 528 from the first enzyme 506 is physical separation. In a cell-free system, such as one that uses microfluidics, the gene 516 may be maintained in one chamber and the ssRNA sequence 522 may be moved from the chamber containing the gene 516 into a different chamber where the enzyme 506 is present.

Physical separation may also be used in cellular implementations. The gene 516 and the enzyme 506 may be contained in different cellular chambers. In one implementation, the gene 516 may be in the nucleus and the enzyme may be outside the nucleus in the cytoplasm or in another cellular chamber. The gene 516 may remain in the nucleus if it is part of the cell's genome. A nuclear export signal (NES) may be used to keep the enzyme, or other component of the system, out of the nucleus. A NES is a short amino acid sequence of four hydrophobic residues in a protein that targets it for export from the cell nucleus to the cytoplasm through the nuclear pore complex using nuclear transport. Similarly, a nuclear localization signal (NLS) may be used to keep the enzyme in the nucleus. A NLS is an amino acid sequence that tags a protein for import into the cell nucleus by nuclear transport. Typically, a NLS consists of one or more short sequences of positively charged lysines or arginines exposed on the protein surface. Different nuclear localized proteins may share the same NLS. An NLS has the opposite function of a NES. Persons of ordinary skill in the art will be able to modify or engineer a protein such as a nuclease or other enzyme to include a NES or a NLS.

The physical location of RNA in a cell may also be controlled. The ssRNA sequence 522 may be exported from its site of transcription in the nucleus to the cytoplasm or other destination outside the nucleus where the enzyme is present. RNA export is described in Sean Carmody and Susan Wente, *mRNA Nuclear Export at a Glance*, 122 J. of Cell Science 1933 (2009) and Alwin Kohler and Ed Hurt, *Exporting RNA from the Nucleus to the Cytoplasm*, 8 Nature Reviews Molecular Cell Biology 761 (2007).

Splicing may be used in place of or in addition to physical separation to protect the gene 516 from being cut by the enzyme 506. In one implementation, the gene 516 may include a sequence with a portion that is later removed by splicing. This additional portion changes the sequence of nucleotides in the gene 516 so that there is no cut site 528 present. The ssRNA sequence 522 will becomes an HDR template 514 through splicing, which also introduces the cut site 528.

Alternative splicing, or differential splicing, is a regulated process during gene expression that results in a single gene coding for multiple proteins. In this process, particular exons of a gene may be included within or excluded from the final, processed messenger RNA (mRNA) produced from that gene. Consequently, the proteins translated from alternatively spliced mRNAs will contain differences in their amino acid sequence and, often, in their biological functions. The production of alternatively spliced mRNAs is regulated by a system of trans-acting proteins that bind to cis-acting sites on the primary transcript itself. Such proteins include splicing activators that promote the usage of a particular splice site, and splicing repressors that reduce the usage of a particular site. There are multiple types of alternative splicing including exon skipping, mutually exclusive exons, alternative donor sites, alternative acceptor sites, and intron retention. Exon skipping is one way to cause splicing in the ssRNA sequence 522; in this case, an exon may be spliced out of the primary transcript. Persons having ordinary skill in the art will understand how to design the gene 516 so that it includes a splice site at a specified location. Alternative splicing may be implemented as a technique to prevent creation of a DSB in the gene 516 even if the gene 516 and enzyme 506 are not physically separated.

Self-excising elements may function similarly to splicing. The gene 516 may be designed to include a region that, when transcribed into RNA, includes one or more self-excising elements. Inclusion of the self-excising elements, for example in a way that disrupts the cut site 528, prevents the gene 516 from being recognized by the enzyme and the excision converts the ssRNA sequence 522 into the HDR template 514. One type of self-excising elements are ribozymes, which are RNA enzymes that function as reaction catalysts. Ribozymes are RNA sequences that catalyze a (trans-esterification) reaction to remove the ribozyme sequence itself from the rest of the RNA sequence. Essentially these are considered introns, which are intragenic regions spliced from mRNA to produce mature RNA with a continuous exon (coding region) sequence. Self-excising introns/ribozymes consist of group I and group II introns. Many group I introns in bacteria are known to self-splice and maintain a conserved secondary structure comprised of a paired element which uses a guanosine (GMP, GDP, or GTP) cofactor. An example of a group I intron is the *Staphylococcus* phage twort.ORF143. Group I and group II introns are considered self-splicing because they do not require proteins to initialize the reaction. Self-excising sequences are known and one of ordinary skill in the art will understand how to include a self-excising sequence in the gene 516. Aspects of self-excising ribozymes are shown in *In Vivo Protein Fusion Assembly Using Self Excising Ribozyme* available at http://2011.igem.org/Team:Waterloo (last visited Mar. 3, 2017).

A series of homologous bridges may also be used to generate a recombinant sequence that is the gene template for the ssRNA sequence 522. The homologous bridges may be present in the DNA at various, separate locations so that the gene 516 does not include a cut site 528. This technique is also known as multi-fragment cloning or extension cloning. The final HDR template 514 is made up of transcripts of the multiple overlapping segments. One suitable technique for combining the multiple-overlapping fragments into the HDR template 514 is Sequence and Ligation-Independent Cloning (SLIC). This technique is described in Mamie Li and Stephen Elledge, *Harnessing Homologous Recombination in vitro to Generate Recombinant DNA Via SLIC,* 4 Nature Methods 250 (2007). Another suitable technique for joining multiple-overlapping fragments is provided by Jiayuan Quan and Jingdong Tian, *Circular Polymerase Extension of Cloning of Complex Gene Libraries and Pathways,* 4(7) PLoS ONE e6441 (2009).

Methylation may be used to protect HDR templates from premature cutting by restriction enzymes because some restriction enzymes do not cut methylated DNA. Other nucleases such as Cas9 may also be prevented from cutting by methylation of a cutting region or PAM recognition site. DNA methylation is a process by which methyl groups are added to the DNA molecule. Methylation can change the activity of a DNA segment without changing the sequence. Two of DNA's four bases, cytosine and adenine, can be methylated. A methylase is an enzyme that recognizes a specific sequence and methylates one of the bases in or near that sequence. Methylation may be controlled by epigenetic editing using a targeting device that is a sequence-specific DNA binding domain which can be redesigned to recognize desired sequences. The targeting device may be fused to an effector domain, which can modify the epigenetic state of the targeted locus. Techniques for using epigenetic editing will be understood by one of ordinary skill in the art. Epigenome manipulations are described in Park, et al., *The epigenome: the next substrate for engineering.* 17 Genome Biology 183 (2016). HDR templates made of RNA may also be modified by methylation. S. Lin and R. Gregory, *Methyltransferases modulate RNA stability in embryonic stem cells,* 16(2) Nature Cell Biology 129 (2014).

In one implementation, the HDR template 514 is a ssDNA sequence complementary to the ssRNA sequence 522. The ssDNA sequence may be created by reverse transcriptase reading (RT) the ssRNA sequence 522 and synthesizing a complementary ssDNA sequence. RT is an enzyme used to generate cDNA from an RNA template, a process termed reverse transcription. RT is widely used in the laboratory to convert RNA to DNA for use in procedures such as molecular cloning, RNA sequencing, PCR, and genome analysis. RT enzymes are widely available from multiple commercial sources. Procedures for use of RT is well known to those of ordinary skill in the art.

The 3'-end sequence 530 and the 5'-end sequence 532 of the HDR template 514 are homologous to one strand of the dsDNA 502 over at least a portion of the first target site 504. The HDR template 514, in both ssDNA and ssRNA implementations, includes a middle portion 534 that, when incorporated into the dsDNA 502, acts as a record on a signal detected by the engineered signaling pathway 536. In an implementation, the middle portion 534 also introduces another target site as described elsewhere in this disclosure.

Enzyme 506 is illustrated here as a CRISPR/Cas complex with gRNA 508. Other types of enzymes discussed above may be used instead of the CRISPR/Cas complex. The single-stranded tail of the gRNA 508 may be extended with a sequence complementary to all or part of the HDR template 514. The HDR template 514 may partially hybridize to the tail of the gRNA 508 forming a double-stranded region 538. This brings a copy of the HDR template 514 into close physical proximity with the location of the DSB created by the CRISPR/Cas complex 506 which can increase HDR efficiency.

The extended tail of the gRNA 508 may also be designed so that it matches the binding domain of a transcription activator-like effector (TALE) protein. The TALE protein may also have a binding domain complementary to the HDR template 514. This will also bring the HDR template into close proximity with the location of the DSB. The tail of the gRNA 508 may be extended to create regions for attachment of multiple copies of the HDR template 514 or TALE proteins.

TALE proteins are proteins secreted by *Xanthomonas* bacteria via their type III secretion system when the bacteria infect various plant species. These proteins can bind promoter sequences in the host plant and activate the expression of plant genes that aid bacterial infection. They recognize plant DNA sequences through a central repeat domain consisting of a variable number of about 34 amino acid repeats. There appears to be a one-to-one correspondence between the identity of two critical amino acids in each repeat and each DNA base in the target site. The most distinctive characteristic of TAL effectors is a central repeat domain containing between 1.5 and 33.5 repeats that are usually 34 nt in length (the C-terminal repeat is generally shorter and referred to as a "half repeat"). A typical repeat sequence may be shared across many TALE proteins but the residues at the $12^{th}$ and $13^{th}$ positions are hypervariable (these two amino acids are also known as the repeat variable diresidue or RVD). This simple correspondence between amino acids in TAL effectors and DNA bases in their target sites makes them useful for protein engineering applications.

Subsequent to creation of a DSB in the target site 504, the molecule 538 that has hybridized to the tail of the gRNA 508 may be released. In some implementations, introduction of a nucleotide sequence complementary to the tail of the gRNA 508 or binding domain of the TALE protein may compete with the attached molecule 538 and cause disassociation of the HDR template 514, TALE protein, or other molecule. This competition may cause the HDR template 514 to become available for binding to the dsDNA 502 on either side of the DSB.

The cell 500 may also include one or more engineered signaling pathways 536. As used herein, "engineered signaling pathway" includes any pathway in which at least one portion of the pathway is intentionally modified with molecular biology techniques to be different from the wild type pathway and a signal (intracellular or extracellular) causes a change in a rate of transcription of a gene. The engineered signaling pathway 536 may induce a promoter such as the promoter 512 described above. The engineered signaling pathway 536 may also cause a transcription factor to bind to an operator such as the operator 514 described above and prevent transcription. In one implementation, the gene affected by the engineered signaling pathway 536 may be the gene 516 that encodes for the ssRNA sequence 522. Thus, the engineered signaling pathway 536 may function to control an amount of the HDR template 514 available in the cell 500. In one implementation, the gene affected by the engineered signaling pathway 536 may encode for an enzyme that creates DSBs in dsDNA such as enzyme 506. Thus, the number of enzymes which create DSBs in the target sites 504 may be regulated by the engineered signaling pathway 536. The engineered signaling pathway 536 may control the transcription of genes that encode other proteins associated with HDR.

The cell 500 may include multiple different engineered signaling pathways 536 each responding to a unique signal and each promoting or repressing expression of genes responsible for the creation of the HDR templates 522 and/or enzymes 506. Thus, intracellular or extracellular signals may be used to vary the levels of HDR templates 514 and/or enzymes 506 in the cell 500 thereby changing which target sites 504 are cut and which sequences are used to repair DSBs through HDR. Responding by up or down regulating any of multiple promoters and/or operators allows the cell 500 to record a log in its DNA of events and complex interactions of events sensed by engineered signaling pathways. In one implementation, the engineered signaling pathway 536 may include an external receptor 540 that can detect extracellular signals across a membrane 542. The membrane 542 may be a cell wall, lipid bilayer, artificial cell wall, or synthetic membrane.

The cell 500 may also include one or more additional dsDNA molecules 544 that may include a second target site 546. Similar to the first dsDNA molecule 502, the additional dsDNA molecule 544 may include only a single instance of the second target site 546. Alternatively, the additional dsDNA molecule 544 may include multiple copies of the same target site or multiple different target sites. The additional dsDNA molecule 544 may be introduced to the cell 500 by any of the techniques described above. In some implementations, the first dsDNA molecule 502 and the additional dsDNA molecule 544 may be introduced by the same procedure. A ratio of the first dsDNA molecule 502 and the additional dsDNA molecule 544 in the cell 500 may be controlled by regulating the respective copies of the dsDNA molecules added to the cell 500.

The additional dsDNA molecule 544 and the second target site 546 may have identical or similar sequences to the first dsDNA molecule 502 and the first target site 504. Thus, the additional dsDNA molecule 544 may be thought of as a "copy" of the first dsDNA molecule 502 in some implementations. This additional copy of an identical or similar molecule may provide redundancy by creating a second log that, absent errors, will record the same series of events in both dsDNA molecules 502, 544. In one implementation, the additional dsDNA molecule 544 may include a target site 546 with a different sequence than the first target site 504 in the first dsDNA molecule 502. Having different target sites 504, 546 in different dsDNA molecules 502, 544 allows for simultaneous, or alternating, encoding of binary data in two different encoding schemes. The two different encoding schemes may be non-overlapping or "orthogonal" so that the enzymes and HDR templates associated with one encoding scheme do not interact with the dsDNA molecule used for the other encoding scheme. For example, insertion of DNA into the first target site 504 may record the presence of signals related to temperature and insertion of DNA into the second target site 546 may record the presence of signals related to light levels. It is understood, that in actual implementation there may be many hundreds or thousands of dsDNA molecules with respective target sites. There may also be a corresponding number of different encoding schemes and different sequences for the respective target sites for creating a detailed log of multiple different signals.

In an implementation, the additional dsDNA molecule 544 may include an operon 548 that encodes components used for logging molecular events. An operon is a contiguous region of DNA that includes cis-regulatory regions (e.g., repressors, promoters) and the coding regions for one or more genes or functional mRNAs (e.g., siRNA, tracrRNA, gRNA, shRNA, etc). The operon 548 may be delivered in a circular vector, such as the additional dsDNA molecule 544, or may be inserted into genomic DNA of the cell 500 through gene editing techniques known to those of skill in the art. In an implementation, the operon 548 may include genes encoding all of the components used by the cell 500 for performing HDR. Thus, addition of a vector such as the dsDNA molecule 544 may enable a cell 500 that includes the necessary engineered signaling pathway 536 to respond to detected signals by adding homology repair templates 522 into a target site 546 on the added dsDNA molecule 544. In this implementation, the homology repair template 514, the enzyme 506, and any accessory proteins may be supplied by genes included in the operon 548. The genes in the operon 548 may be under the control of a single promoter 550 and operator 552.

In an implementation, the operon 548 may include any or all of a gene encoding an HDR template 554, a gene encoding an enzyme configured to make DSBs 556, and a gene that encodes a tracking molecule 558 (e.g., RNA, DNA, or protein) for monitoring "state" as described below. An operon 548 that includes genes encoding all of the products for performing HDR may be added to a cell-free system on a circular dsDNA molecule 544 that also includes a target site 546 to provide complete instructions for a molecular event logging system on one molecule.

The term "operably linked" as used herein means placing a gene under the regulatory control of a promoter, which then controls the transcription and optionally the translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

"Constitutive promoters" are typically active, i.e., promote transcription, under most conditions. "Inducible promoters" are typically active only under certain conditions, such as in the presence of a given molecule factor (e.g., IPTG) or a given environmental condition (e.g., particular $CO_2$ concentration, nutrient levels, light, heat). In the absence of that condition, inducible promoters typically do not allow significant or measurable levels of transcriptional activity. For example, inducible promoters may be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters are known to one of skill in the art.

Illustrative eukaryotic promoters known to one of skill in the art are listed below.

| Promoter | Primarily used for | Description | Additional considerations |
|---|---|---|---|
| CMV | General expression | Strong mammalian expression promoter from the human cytomegalovirus | May contain an enhancer region. Can be silenced in some cell types. |
| EF1a | General expression | Strong mammalian expression from human elongation factor 1 alpha | Tends to give consistent expression regardless of cell type or physiology. |
| SV40 | General expression | Mammalian expression promoter from the simian vacuolating virus 40 | May include an enhancer. |
| PGK1 (human or mouse) | General expression | Mammalian promoter from phosphoglycerate kinase gene. | Widespread expression, but may vary by cell type. Tends to resist promoter down regulation due to methylation or deacetylation. |
| Ubc | General expression | Mammalian promoter from the human ubiquitin C gene | As the name implies, this promoter is ubiquitous. |
| human beta actin | General expression | Mammalian promoter from beta actin gene | Ubiquitous. Chicken version is commonly used in promoter hybrids. |
| CAG | General expression | Strong hybrid mammalian promoter | Contains CMV enhancer, chicken beta actin promoter, and rabbit beta-globin splice acceptor. |
| TRE | General expression | Tetracycline response element promoter | Typically contains a minimal promoter with low basal activity and several tetracycline operators. Transcription can be turned on or off depending on what tet transactivator is used. |
| UAS | General expression | *Drosophila* promoter containing Gal4 binding sites | Requires the presence of Gal4 gene to activate promoter. |
| Ac5 | General expression | Strong insect promoter from *Drosophila* Actin 5c gene | Commonly used in expression systems for *Drosophila*. |
| Polyhedrin | General expression | Strong insect promoter from baculovirus | Commonly used in expression systems for insect cells. |
| CaMKIIa | Gene expression for optogenetics | Ca2+/calmodulin-dependent protein kinase II promoter | Used for neuronal/CNS expression. Modulated by calcium and calmodulin. |
| GAL1, 10 | General expression | Yeast adjacent, divergently transcribed promoters | Can be used independently or together. Regulated by GAL4 and GAL 80. |
| TEF1 | General expression | Yeast transcription elongation factor promoter | Analogous to mammalian EF1a promoter. |
| GDS | General expression | Strong yeast expression promoter from glyceraldehyde 3-phosphage dehydrogenase | Very strong, also called TDH3 or GAPDH. |
| ADH1 | General expression | Yeast promoter for alcohol dehydrogenase I | Full length version is strong with high expression. Truncated promoters are constitutive with lower expression. |
| CaMV35S | General expression | Strong plant promoter from the Cauliflower Mosaic Virus | Active in dicots, less active in monocots, with some activity in animal cells. |

-continued

| Promoter | Primarily used for | Description | Additional considerations |
|---|---|---|---|
| Ubi | General expression | Plant promoter from maize ubiquitin gene | Gives high expression in plants. |
| H1 | small RNA expression | From the human polymerase III RNA promoter | May have slightly lower expression than U6. May have better expression in neuronal cells. |
| U6 | small RNA expression | From the human U6 small nuclear promoter | Murine U6 is also used, but may be less efficient. |

Illustrative prokaryotic promoters known to one of skill in the art are listed below.

| Promoter | Primarily used for | Description | Expression | Additional considerations |
|---|---|---|---|---|
| T7 | in vitro transcription/ general expression | Promoter from T7 bacteriophage | Constitutive, but requires T7 RNA polymerase. | When used for in vitro transcription, the promoter drives either the sense OR antisense transcript depending on its orientation to your gene. |
| T7lac | High levels of gene expression | Promoter from T7 bacteriophage plus lac operators | Negligible basal expression when not induced, Requires T7 RNA polymerase, which is also controlled by lac operator. Can be induced by IPTG. | Commonly found in pET vectors. Very tightly regulated by the lac operators. Good for modulating gene expression through varied inducer concentrations. |
| Sp6 | in vitro transcription/ general expression | Promoter from Sp6 bacteriophage | Constitutive, but requires SP6 RNA polymerase. | SP6 polymerase has a high processivity. When used for in vitro transcription, the promoter drives either the sense OR antisense transcript depending on its orientation to your gene. |
| araBAD | General expression | Promoter of the arabinose metabolic operon | Inducible by arabinose and repressed catabolite repression in the presence of glucose or by competitive binding of the anti-inducer fucose | Weaker. Commonly found in pBAD vectors. Good for rapid regulation and low basal expression; however, not well-suited for modulating gene expression through varied inducer concentrations. |
| trp | High levels of gene expression | Promoter from *E. coli* tryptophan operon | Repressible | Gets turned off with high levels of cellular tryptophan. |
| lac | General expression | Promoter from lac operon | Constitutive in the absence of lac repressor (lacI or lacIq). Can be induced by IPTG or lactose. | Leaky promoter with somewhat weak expression. lacIq mutation increases expression of the repressor 10x, thus tightening regulation of lac promoter. Good for modulating gene expression through varied inducer concentrations. |
| Ptac | General expression | Hybrid promoter of lac and trp | Regulated like the lac promoter | Contains −35 region from trpB and −10 region from lac. Very tight regulation. Good for modulating gene expression through varied inducer concentrations. Generally better expression than lac alone. |
| pL | High levels of gene expression | Promoter from bacteriophage lambda | Can be temperature regulatable | Often paired with the temperature sensitive cI857 repressor. |

Figure 6:
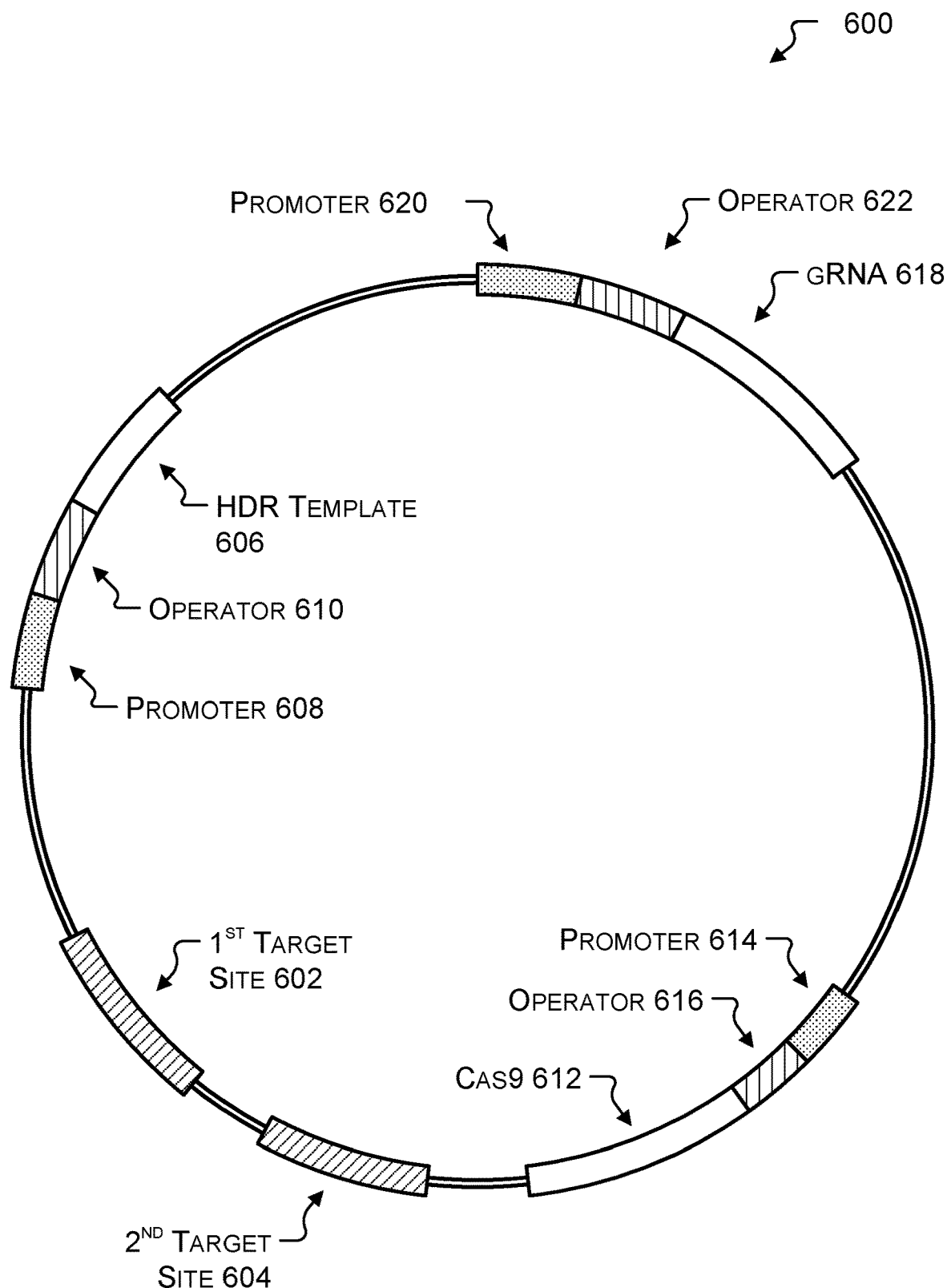
FIG. 6 shows an illustrative dsDNA plasmid containing components for controlling the synthesis of an HDR template and a nuclease.

FIG. 6 shows a dsDNA molecule 600 that contains genes for encoding the components used to incorporate an HDR template into a target site. The dsDNA molecule 600 may be the same or similar to the dsDNA molecule 502 or 544 introduced in FIG. 5. In an implementation, the dsDNA molecule 600 may be a vector or plasmid as described above. This dsDNA molecule 600 may be added to a cell by any of the techniques discussed in this disclosure such as transfection, transformation, conjugation, etc.

In an implementation, the dsDNA molecule 600 may encode one or more target sites for insertion of HDR templates such as a first target site 602 and a second target site 604. HDR templates integrated into the target sites 602, 604 may correspond to timing signals or molecular events experienced by the cell. The dsDNA molecule 600 can also encode multiple operons each including a promoter, an operator, and a gene. A gene encoding an HDR template 606 may be regulated by a promoter 608 and an operator 610. A gene encoding a Cas9 enzyme 612 may be regulated by a second promoter 614 and second operator 616. Cas9 is shown in this example but any enzyme capable of creating DSBs may be alternatively present in the dsDNA molecule 600. Cas9 targets a specific sequence for cutting based on the associated gRNA and the dsDNA molecule 600 may also include a gene for a gRNA 618 regulated by a third promoter 620 and a third operator 622. In this example, the HDR template 606, the nuclease Cas9 612, and the gRNA 618 are all controlled by different sets of promoters and operators. However, any two or all three may be combined together in a single operon controlled by the same regulatory sequences.

Insertion of an HDR template in response to a timing signal occurs when there is a DSB at an appropriate target site and sufficient copies of the HDR template are available to contact and recombine with the cut polynucleotide at the target site. Thus, the ability to integrate an HDR template in response to a timing signal may be regulated by controlling availability of the HDR template or the enzyme used to create the DSB at the appropriate target site. Addition of the dsDNA molecule 600 to a cell provides all of the components for recording timing signals. Presence of a timing signal whether due to manual manipulation of the cell or due to a periodic cycle within the cell can affect any of the promoters 608, 614, 620 or operators 610, 616, 622. Thus, integration of an HDR template into a target site 602, 604 can be regulated by controlling expression of any of the gene for the HDR template 606, the gene for the Cas9 nuclease 612, or the gene for the gRNA 618. The regulation may include inducing expression of one of the promoters 608, 614, 620, ceasing inhibition of one of the operators 610, 616, 622, or otherwise manipulating the regulatory elements associated with one of the relevant genes.

Figure 7:
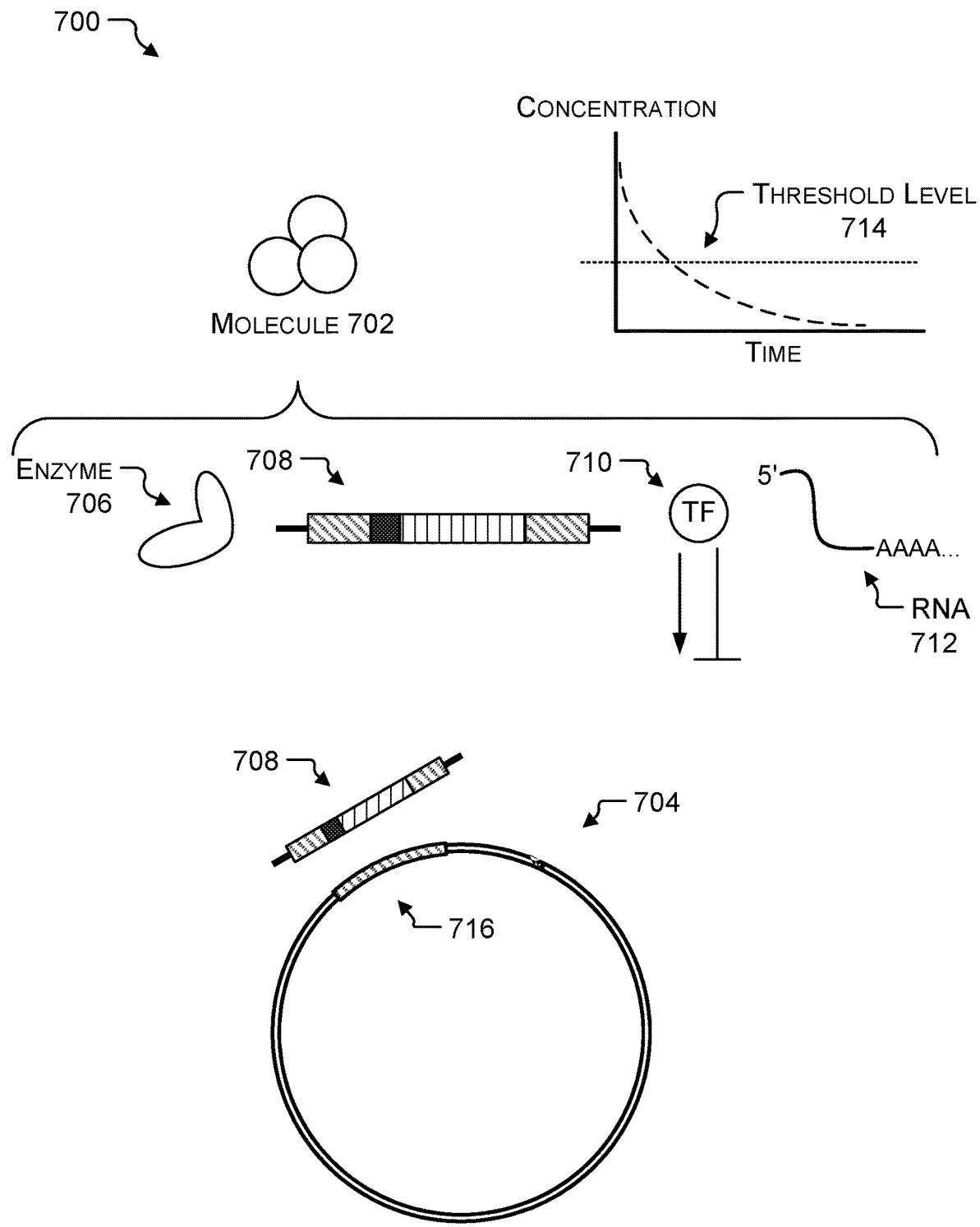
FIG. 7 shows an illustrative molecule that degrades with time and affects integration of an HDR template into a double-stranded polynucleotide.

FIG. 7 shows a diagram 700 including a molecule 702 that degrades in a cellular system at a known rate. The change in concentration of the molecule 702 due to degradation provides a source of timing that can be used to determine the timing of molecular events detected by the cellular system. The molecule 702 may be any one of a number of different types of molecules that are involved in repair of a DSB by using an HDR template.

For example, the molecule 702 may be all or part of an enzyme 704 configured to create a DSB in a double-stranded polynucleotide such as the double-stranded polynucleotide 704. The enzyme 706 may be any of the nucleases discussed above such as Cas9. Proteins such as Cas9 will degrade in cells due to the presence of proteases. This rate of degradation may be experimentally established for a given cellular system. For in vivo logging, it is possible to use externally pre-synthesized, purified Cas9 or include the gene for Cas9 in a vector or plasmid as shown in FIG. 6. As discussed above, the enzyme 706 creates a DSB at a cut site that is flanked by regions homologous to an HDR template. Hybridization of the homologous regions to the HDR template permits homologous directed repair of the DSB. The enzyme 706 is a protein; the stability of a protein can be altered by introducing mutations into the amino acid sequence that make the protein more or less resistant to denaturation or proteolytic degradation. Persons having ordinary skill in the art will appreciate various techniques to modify the duration that a protein remains active in a given cellular environment. Techniques such as directed evolution, DNA shuffling and two-hybrid screening are known in the art and may be used to rapidly screen large numbers of mutant proteins for the desired stability characteristics. In addition, protein degradation rate may be altered by attaching a short, organism-specific, oligonucleotide sequence to the 3'-end of the gene which encodes the protein as described in Andersen et al. (1998) Appl. Environ. Microbiol. 64:2240-2246. This sequence targets the encoded protein for rapid degradation by the cell. Thus, the rate of degradation of a protein may be adjusted to achieve a desired timing.

In an implementation, the molecule 702 may be an HDR template 708. As described above, HDR template 708 may be ssDNA or ssRNA. Natural degradation processes in a cell can cause free ssDNA or mRNA to degrade over time. The degradation speed may be increased by addition of proteasomes or nucleases. Thus, intentional design of the cellular system including the amount of proteases and/or nucleases may be used to tune or adjust the rate of degradation.

In an implementation, the molecule 702 can be a transcription factor 710. The transcription factor 710 can increase transcription of a gene encoding the HDR template 708 or a gene encoding enzyme configured to create a DSB in the double-stranded polynucleotide 704. For example, the transcription factor 710 may interact with any of the promoters 608, 614, 620 described in FIG. 6.

The molecule 702 can be a RNA molecule 712. For example, the RNA molecule 712 may be gRNA that functions with the Cas9 nuclease. Cas9 is able to take up the gRNA dynamically when available, thus the Cas9 enzyme may be present in abundance and the ability to create targeted DSBs may depend on the concentration of gRNA. After export to the cytoplasm, mRNA (including gRNA) is protected from degradation by a 5' cap structure and a 3' poly(A) tail. The rate of mRNA degradation is typically minutes in prokaryotes and hours-months in eukaryotes. A rate of degradation of the RNA 712 may be determined in part by a modification to a 3' poly(A) tail. A longer poly(A) tail generally correlates with greater stability of RNA and a shorter poly(A) tail generally leads to faster degradation of the RNA. Specifically, the degradation of RNA may be affected by the 3'-untranslated region (3'-UTR). The 3'-UTR can influence polyadenylation, translation efficiency, localization, and stability of the mRNA. The 3'-UTR contains both binding sites for regulatory proteins as well as microRNAs (miRNAs). By binding to specific sites within the 3'-UTR, miRNAs can decrease gene expression of various mRNAs by either inhibiting translation or directly causing degradation of the transcript. The 3'-UTR contains both binding sites for regulatory proteins as well as miRNAs. By binding to specific sites within the 3'-UTR, miRNAs can decrease gene expression of various mRNAs by either inhibiting translation or directly causing degradation of the transcript.

Mature microRNAs (miRNAs) are a class of naturally occurring, small non-coding RNA molecules, about 21-25 nt in length. They are found in plants, animals and some viruses, and have functions in RNA silencing and post-transcriptional regulation of gene expression. MicroRNAs are partially complementary to one or more messenger RNA (mRNA) molecules, and their main function is to down-regulate gene expression in a variety of manners, including translational repression, mRNA cleavage, and deadenylation.

Encoded by eukaryotic nuclear DNA in plants and animals and by viral DNA in certain viruses whose genome is based on DNA, miRNAs function via base-pairing with complementary sequences within mRNA molecules. As a result, the RNA 712 can be silenced, by one or more of the following processes: cleavage of the RNA 712 strand into two pieces, destabilization of the RNA 712 through shortening of its poly(A) tail, and less efficient translation of the RNA 712 into proteins by ribosomes. For example, miR16 contains a sequence complementary to the AU-rich element found in the 3'-UTR of many unstable mRNAs, such as TNF alpha or GM-CSF. It has been demonstrated that given complete complementarity between the miRNA and target mRNA sequence, Ago2 can cleave the mRNA and lead to direct mRNA degradation. Jing, Q. et al. *Involvement of microRNA in AU-rich element-mediated mRNA instability.* 120(5) Cell 623 (2005).

The genes encoding miRNAs are much longer than the processed mature miRNA molecule. Many miRNAs are known to reside in introns of their pre-mRNA host genes and share their regulatory elements, primary transcript, and have a similar expression profile. MicroRNAs are transcribed by RNA polymerase II as large RNA precursors called pri-miRNAs and comprise of a 5' cap and poly-A tail3. The pri-miRNAs are processed in the nucleus by the microprocessor complex, consisting of the RNase III enzyme Drosha4, and the double-stranded-RNA-binding protein, Pasha/DGCR85. The resulting pre-miRNAs are approximately 70-nt in length and are folded into imperfect stem-loop structures. The pre-miRNAs are then exported into the cytoplasm by the karyopherin exportin 5 (Exp5) and Ran-GTP complex. Ran (ras-related nuclear protein) is a small GTP binding protein belonging to the RAS superfamily that is essential for the translocation of RNA and proteins through the nuclear pore complex. The Ran GTPase binds Exp5 and forms a nuclear heterotrimer with pre-miRNAs. Once in the cytoplasm, the pre-miRNAs undergo an additional processing step by the RNAse III enzyme Dicer9 generating the miRNA, a double-stranded RNA approximately 22 nt in length.

Concentration of the molecule 702 may vary in the cellular system with respect to time. Starting from an initial concentration, degradation of the molecule 702 will eventually cause the concentration of the molecule 702 to drop below a threshold level 714. The threshold level 714 may be determined experimentally or known from the behavior of the molecule 702. If the molecule 702 functions to promote insertion of the HDR template 708 into the double-stranded polynucleotide 704, then insertion of the HDR template 708 into a target site 716 of the double-stranded polynucleotide 704 indicates that the incorporation occurred prior to the concentration of the molecule 702 dropping below the threshold level 714. Alternatively, if the molecule 702 functions as a repressor, for example a transcription factor 710 that binds to an operator, then incorporation of the HDR template 708 will indicate that enough time has passed such that the concentration of the molecule 702 has dropped below the threshold level 714.

This technique for controlling insertion of the HDR template 708 into the target site 716 of a double-stranded polynucleotide 704 based on the concentration of a molecule 702 with respect to a threshold level 714 may be combined with any of the other techniques described in this disclosure to control the timing of HDR based on the rate of degradation of the molecule 702.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations may be modified or omitted.

Process 800 shows an illustrative technique for introducing timing indicators into the DNA of a cell based on manual manipulation of the cell.

At 802, the cell is exposed to a timing indicator at a known time. The timing indicator may be a chemical or environmental condition that causes the cell to integrate an HDR template into a double-stranded polynucleotide. Exposure to the timing indicator may be performed "manually" by placing the cell in an environment which is known to generate the corresponding signal. For example, the cell could be bathed in a solution containing a particular chemical which causes a response in a signaling pathway of the cell. Because exposure is controlled, the time of exposure may be recorded so that later analysis can identify insertion of this first HDR template as having occurred at the time of exposure.

The exposure may include making sufficient copies of the first HDR template available so that HDR can occur, making a nuclease available, if the nuclease is Cas9, then the exposure may include making targeted gRNA available. The timing indicator, no matter how generated, may be detected by an engineered signaling pathway in the cell and this detection may cause the cell to increase transcription of either the first HDR template or an enzyme. Increasing transcription of the first HDR template ultimately results in more copies of the first HDR template being available for incorporation into the double-stranded polynucleotide in the cell. The first HDR template includes a first middle portion that is not homologous to the double-stranded polynucleotide, and thus, represents a new nucleotide sequence that will be inserted by homology directed repair. Similarly, increase in the number of functional enzymes that act at the cut site, increases the number of DSBs that are available to be repaired by the HDR templates. Either, or both, may ultimately result in more copies of the first middle portion of the first HDR template being incorporated into the double-stranded polynucleotide.

Engineered signaling pathways in the cell may be used to cause integration of HDR templates in response to light, temperature, change in pH, etc. Conditions of the cell may be controlled so that the trigger for integrating a time indicator does not occur unless intentionally caused. For example, the cells may be kept in the dark, the temperature may be tightly regulated, the pH may be maintained by buffering solution, etc.

The HDR temple may be generated by a gene under control of a regulated promoter that responds to the exposure. The mRNA gene product may be converted to DNA through use of RT to create a DNA molecule that is the final HDR template. In some implementations, the mRNA may itself serve as the HDR template without conversion to DNA.

In order to limit where the first enzyme cuts the double-stranded polynucleotide, the first target site may be unique in the double-stranded polynucleotide at the time of making the first DSB. The first target site may also be unique across a population of double-stranded polynucleotides that is available for the first enzyme to act on. For example, if there are multiple circular dsDNA molecules within a cell, the first target site may exist only once within the entire population of circular dsDNA molecules. Alternatively, the first target site may be unique per dsDNA molecule, but the first enzyme may have access to multiple different dsDNA molecules each including one instance of the first target site. It is understood by persons having ordinary skill in the art that the enzyme (even if referred to in the singular herein) may include a plurality of individual and equivalent enzyme molecules. In some implementations, the first target site may include a first subsequence that is repeated once resulting in a second subsequence that is the same as the first subsequence. For example, if the first subsequence is GTACTA then the second subsequence is the same and the sequence of the target site is GTACTAGTACTA (SEQ ID NO: 9).

The enzyme may be any of the illustrative types of enzymes identified in this disclosure such as a restriction enzyme, HE, a CRISPR/Cas system, a TALEN, or a zinc finger.

The HDR template may include a 3'-end sequence and a 5'-end sequence each encoding a second subsequence that is homologous to the first subsequence in the first target site. Thus, in this implementation the 3'-end sequence and the 5'-end sequence have the same sequence, but in other implementations they may have different sequences. The first HDR template may also include a middle portion that includes two adjacent instances of a third subsequence that forms the next target site after insertion into the double-stranded polynucleotide as shown in FIGS. 1 and 2.

This contact may result from diffusion and/or Brownian motion of the HDR template moving within the cell until it contacts the DSB on the double-stranded polynucleotide. Contacting the double-stranded polynucleotide with the first HDR template may involve movement of multiple copies of the first HDR template into a chamber that contains the double-stranded polynucleotide such as, for example, by a microfluidics system or localization to a cellular chamber such as the nucleus. In one implementation, contacting the double-stranded polynucleotide involves upregulating expression of a gene encoding for a RNA sequence that is itself the HDR template or that serves as a template for creation of the HDR template. Upregulating expression of the gene may include any of activating a promoter controlling transcription of the gene, upregulating the promoter controlling transcription, unblocking a promoter controlling transcription of the gene, and/or inhibiting action of a repressor or silencer.

At 804, the cell logs one or more molecular events. The cell can integrate a second HDR template into a repair formed by the first HDR template in the double-stranded polynucleotide in response to a molecular event. The repair formed by the first HDR template includes the next target site into which the second HDR template may be integrated. Thus, in this example, the cell logs a molecular event in a portion of polynucleotide that is created by adding the first HDR template in response to the timing indicator. The molecular event may be an intracellular or extracellular event that corresponds to a change in a biological condition of the cell or a change in the condition of the external environment. The molecular event is different than the timing indicator at least because the timing of the molecular event is not manually controlled and the molecular event is initiated by a sensed condition. The cell can iteratively integrate multiple copies of the second HDR template into the double-stranded polynucleotide while the molecular event continues.

Using nomenclature introduced earlier in this disclosure, the first HDR template may be represented as XaXXaX which can be inserted into the target site XX and includes, after insertion, the same target site XX in the middle. While, the second HDR template may be represented as XbXXbX with "b" representing the part of the second middle portion that is different from the first middle portion of the first HDR template (i.e., "a"≠"b"). Thus, presence of the polynucleotide sequence corresponding to "a" corresponds to the timing indicator and presence of "b" corresponds to a molecular event. The sequence XaXbXXbXaX can then provide a record that molecular event "b" occurred at or shortly after the time point indicated by "a." The sequences "a" and "b" both as they exist in HDR templates and following integration into a double-stranded polynucleotide are "identifier regions" that provide identification separate from the polynucleotide sequences used for forming homologies.

At 806, it is determined if there are any additional timing indications. For example, the cell may be exposed to the timing indicator at a plurality of known times. Each of the plurality of known times may be recorded in a look-up table or other form for use in later correlating records of molecular events with time points.

At 808, sequence data is obtained from the double-stranded polynucleotide. Sequencing, through any technique for DNA sequencing known to one of skill in the art, generates a sequence of the double-stranded polynucleotide including sequences introduced by the HDR template. The sequence data output from a polynucleotide sequencer is a computer file that is amenable to electronic analysis and manipulation.

In one implementation, all the DNA in the cell may be sequenced. In another implementation only the double-stranded polynucleotide may be sequenced. For example, if the double-stranded polynucleotide molecule is a vector, known primer sites on the vector may be used to sequence only the DNA of that vector and not the entirety of the DNA in the cell. In yet another implementation, polynucleotides in the region of the target site may be sequenced. For example, the target site in the double-stranded polynucleotide may be flanked with known sequences that can be used to design primers which specifically select and amplify the target site and any sequence integrated into the middle of the target site. Doing so captures any portions of HDR templates that were integrated into the target site.

At 810, the molecular event is correlated with the known time. The sequence data obtained at 808 can be interpreted to identify a record of a molecular event and or a timing indicator. The interpretation may be as simple as identifying that the sequence of the middle portion of the HDR template is present in the sequence data. Recall that the HDR template is designed and intentionally inserted into a cell through transfection or another process. Thus, the sequence is known and can be used as a search query run against the content of the sequence data. Interpreting the meaning of finding such a sequence in the sequence data depends on the construction of the cell and association between a given signal and the HDR template. Thus, if the cell is designed so that detection of a signal (e.g., light) leads to incorporation of an HDR template with a middle portion having a sequence AGT-TACGGA, then presence of the sequence AGTTACGGA in the sequence file serves as a record that the cell experienced light sufficient to trigger the relevant signaling pathway. The correlating may involve identifying in the sequence data a sequence from the second HDR template (i.e., molecular event) adjacent to a first sequence from the first HDR template (i.e., timing indication). In other words, the second HDR template is integrated into the double-stranded polynucleotide in the middle of the first HDR template that has been previously integrated. The sequences are "adjacent" if after integration into the double-stranded polynucleotide, nucleotides from one HDR template are contiguous with nucleotides from the other, or if there are only a small number of intervening nucleotides such as fewer than 10, 9, 8, 7, 6, 5, 4, 3, 2, or 1 nt.

Converting the identification of a sequence in sequence data to the identity of a signal and timing of the signal may be done by using a look-up table or other technique for correlating a DNA sequence with a type of signal and timing indicator. The correlation may be known based on the relationship between the engineered signaling pathway, a promoter affected by the engineered signaling pathway, and the sequence of the first and second HDR templates regulated by promoters. Reporting of the correlation and the timing may be performed, for example, by indicating the signal on a user interface of an electronic device such as a computer or a polynucleotide sequencer.

Illustrative Timing Techniques

Figure 8:
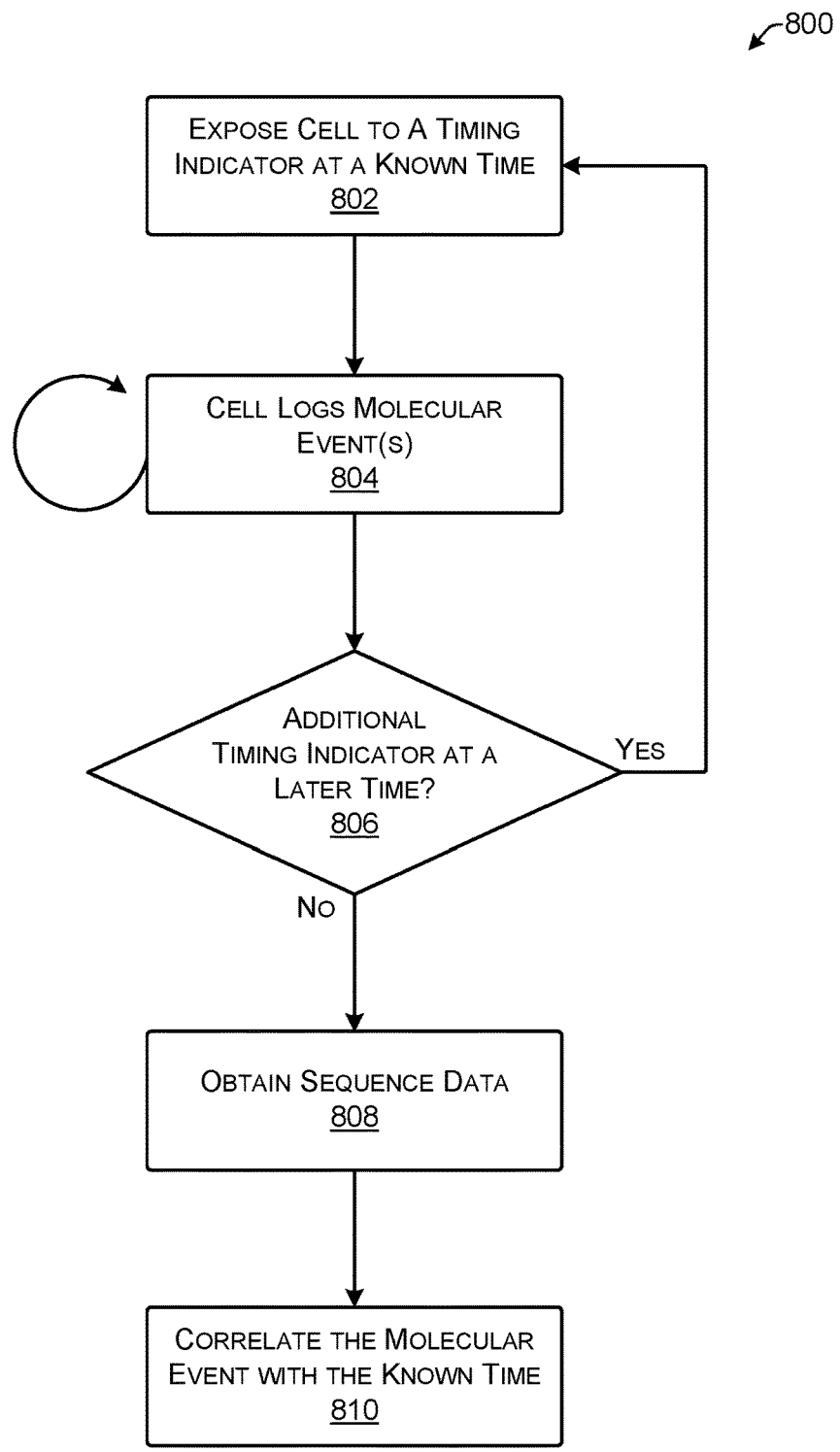
FIG. 8 shows an illustrative process for adding timing indicators into the DNA of a cell.
Figure 9:
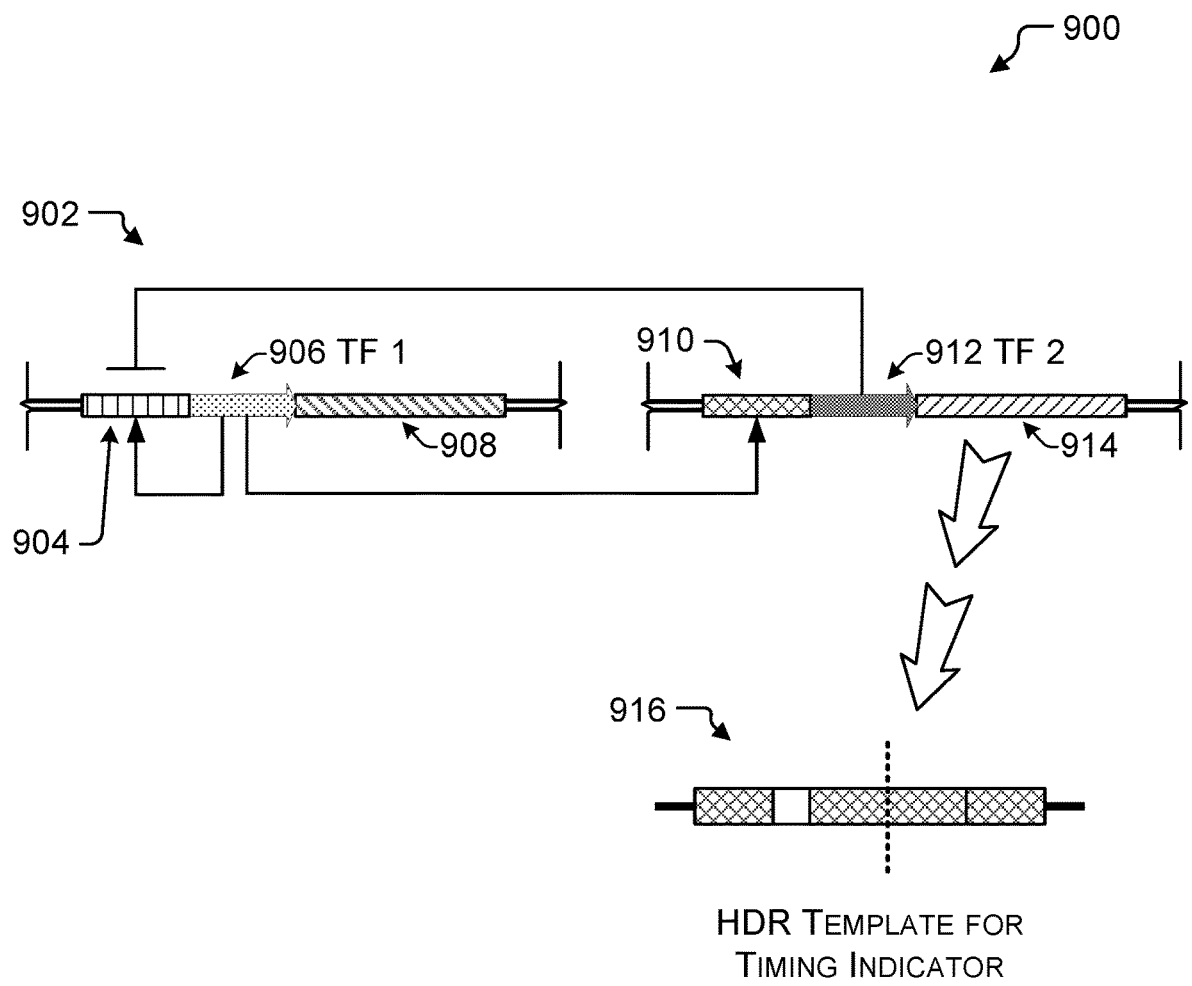
FIG. 9 shows an illustrative genetic circuit.

FIG. 9 shows a schematic 900 of a gene regulated by a genetic circuit creating an internal biological "clock" that results in creation of HDR templates at a timing driven by behavior of the genetic circuit. In addition to the manual timing described in FIG. 8, automatic timing based on biological clocks can be used to generate timing signals that are integrated into a polynucleotide.

There are many types of biological clocks both natural and synthetic. Natural autonomous cycles that may exist within a cell include the cell cycle, the metabolic cycle, photosynthesis activity, cycles caused by cell stress, etc. Natural cycles might come from neighboring cells such as electrical impulses from synapses. For cells that are part of a multi-cellular organism, there may be endocrine signals like cortisol (e.g., circadian rhythm), stress hormones, or development hormones (e.g., fruit ripening in plants). Any of these cycles may be harnessed to use periodic availability of particular molecules as timing signals that can regulate the ability of the cell to perform homology directed repair.

The cell cycle or cell-division cycle, for example, is the series of events that take place in a cell leading to its division and duplication of its DNA (DNA replication) to produce two daughter cells. In bacteria, which lack a cell nucleus, the cell cycle is divided into the B, C, and D periods. The B period extends from the end of cell division to the beginning of DNA replication. DNA replication occurs during the C period. The D period refers to the stage between the end of DNA replication and the splitting of the bacterial cell into two daughter cells. In cells with a nucleus, as in eukaryotes, the cell cycle is also divided into three periods: interphase, the mitotic (M) phase, and cytokinesis. During interphase, the cell grows, accumulating nutrients needed for mitosis, preparing it for cell division and duplicating its DNA. During the mitotic phase, the chromosomes separate. During the final stage, cytokinesis, the chromosomes and cytoplasm separate into two new daughter cells. To ensure the proper division of the cell, there are control mechanisms known as cell cycle checkpoints.

Two key classes of regulatory molecules, cyclins and cyclin-dependent kinases (CDKs), determine a cell's progress through the cell cycle. Cyclins form the regulatory subunits and CDKs the catalytic subunits of an activated heterodimer; cyclins have no catalytic activity and CDKs are inactive in the absence of a partner cyclin. When activated by a bound cyclin, CDKs perform a common biochemical reaction called phosphorylation that activates or inactivates target proteins to orchestrate coordinated entry into the next phase of the cell cycle. Different cyclin-CDK combinations determine the downstream proteins targeted. CDKs are constitutively expressed in cells whereas cyclins are synthesized at specific stages of the cell cycle, in response to various molecular signals.

Two families of genes, the cip/kip (CDK interacting protein/Kinase inhibitory protein) family and the INK4a/ARF (Inhibitor of Kinase 4/Alternative Reading Frame) family, prevent the progression of the cell cycle. Because these genes are instrumental in prevention of tumor formation, they are known as tumor suppressors.

The cip/kip family includes the genes p21, p27 and p57. They halt cell cycle in GI phase, by binding to, and inactivating, cyclin-CDK complexes. p21 is activated by p53 (which, in turn, is triggered by DNA damage e.g. due to radiation). p27 is activated by Transforming Growth Factor of β (TGF β), a growth inhibitor. The INK4a/ARF family includes p16INK4a, which binds to CDK4 and arrests the cell cycle in G1 phase, and p14ARF which prevents p53 degradation. Any of the regulatory molecules involved in the cell cycle may be used, for example by an engineered signaling pathway, to control an HDR template and associated homology directed repair behavior in order to create a genetic record that tracks the timing of the corresponding natural cellular cycle.

In addition to natural cycles or clocks, artificial cyclic events may be created by genetic circuits created through well-established synthetic biology techniques known to those of ordinary skill in the art. A synthetic genetic circuit(s) can be configured as a switch, a bi-stable switch, a toggle switch, an oscillator, a repressilator, a counter, an anticipator, a learner, a kill switch, a quorum sensor (sender or receiver), a two-way signaling system, and-gates, nor-gates, nand-gate, inverters, or-gates, engineered ecosystem circuits, single invertase memory modules, analog-to-digital converters, digital-to-analog converters or any combination thereof. A synthetic genetic circuit can be tunable and thus allow for modulation of expression of one or more reporter genes. In some embodiments, the synthetic genetic circuit can be designed using a program such as GenoCAD, Clotho framework, or j5. The synthetic genetic circuit can contain one or more reporter genes. Suitable reporter genes are generally known in the art. Such reporter genes include, but are not limited to, optically active proteins (e.g. green fluorescent protein and variants thereof (e.g. eGFP), red fluorescent protein and variants thereof (e.g. mCherry)), lacZ (produces beta-galatosidase), cat (produces chloramphenicol acetyltransferase), beta-lactamase, and other antibiotic resistance genes.

The reporter genes can be operatively coupled to one or more transcriptional control elements. As used herein, "transcriptional control element" can refer to any element of the synthetic genetic circuit, including proteins, DNA, RNA, or other molecules that can, either alone or in conjunction with other elements of the synthetic genetic circuit, stimulate and/or repress the transcription of one or more reporter genes within the synthetic genetic circuit. Such transcriptional control elements will be apparent to those in the art and include, but are not limited to operons and components thereof, bacterial repressors, eukaryotic promoters and elements therein, DNA binding proteins, signaling molecules, riboregulators, toe-hold switches, siRNA, and the like.

There are well-known gene networks that oscillate without the need for external chemical inducers. One oscillating synthetic genetic circuit that is a canonical feature within the field of synthetic biology is described in Stricker, J. et al., *A fast, robust and tunable synthetic gene oscillator,* 456 Nature 516 (2008) and Hasty, J., et al., *Synthetic Gene Network for Entraining and Amplifying Cellular Oscillations,* 88 Physical Review Letters 148101 (2002). A different network uses an orthogonal circuit containing negative feedback. This gene network causes elevated levels of a first signal protein only when levels of acyl-homoserine lactone (AHL) within the cell increased. However, when the target is further away, AHL input decreases, the circuit represses and concentration of signal protein attenuates. Voliotis, M., and Bowsher, C. G., *The magnitude and colour of noise in genetic negative feedback systems.* 40 Nucleic Acids Research 7084 (2012). Persons of ordinary skill in the art will understand how to construct these and other types of synthetic genetic circuits.

The illustrative gene oscillator 902 shown in FIG. 9 is one nonlimiting example of a synthetic genetic circuit. The gene oscillator 902 includes a first operon with a promoter 904 that controls expression of a first transcription factor 906 and a first gene 908. The first transcription factor 906 also up regulates the promoter 904 creating a positive feedback loop. Furthermore, the first transcription factor 906 also up regulates a second promoter 910 on a second operon. The second promoter 910 controls expression of a second transcription factor 912 and a second gene 914. The second transcription factor 912 suppresses the first promoter 904 which in turn reduces expression of the first transcription factor 906.

This arrangement creates oscillating behavior because initially the first transcription factor 906 will cause the first promoter 904 to create ever larger amounts of the first transcription factor 906 leading to increase in expression of the second gene 914 controlled by the second promoter 910. The second gene 914 is responsible for increasing homologous directed repair using an HDR template 916. However, increasing concentration of the first transcription factor 906 also leads to increased expression of the second transcription factor 912. Because the second transcription factor 912 suppresses activity of the first promoter 904, it will eventually lead to decreased expression of the second gene 914. Thus, the availability of the HDR template 916 will fluctuate with a known periodicity based on the behavior of the gene oscillator 902.

As described above, there are multiple ways in which increased integration of an HDR template may be regulated. For example, the second gene 914 may directly code for the HDR template 916 as RNA or as RNA that is later transcribed into DNA. Alternatively, the second gene 914 may be involved in increasing the number of DSBs into which the HDR template 916 may be integrated. This can be done by increasing the number of enzymes configured to create DSBs in a double-stranded polynucleotide. Thus, the second gene 914 may encode the protein that functions as a nuclease or may include another gene product that assists with the functioning of the nuclease such as, for example a gRNA that includes a protospacer element that guides Cas9 to a particular target site by hybridizing with one strand of the target site. The HDR template 916 may include features similar to any of the other HDR templates described in this disclosure. Incorporation of this HDR template 916 into a double-stranded polynucleotide creates a record of a timing indicator that occurs at a periodicity established by the design of the gene oscillator 902.

Figure 10:
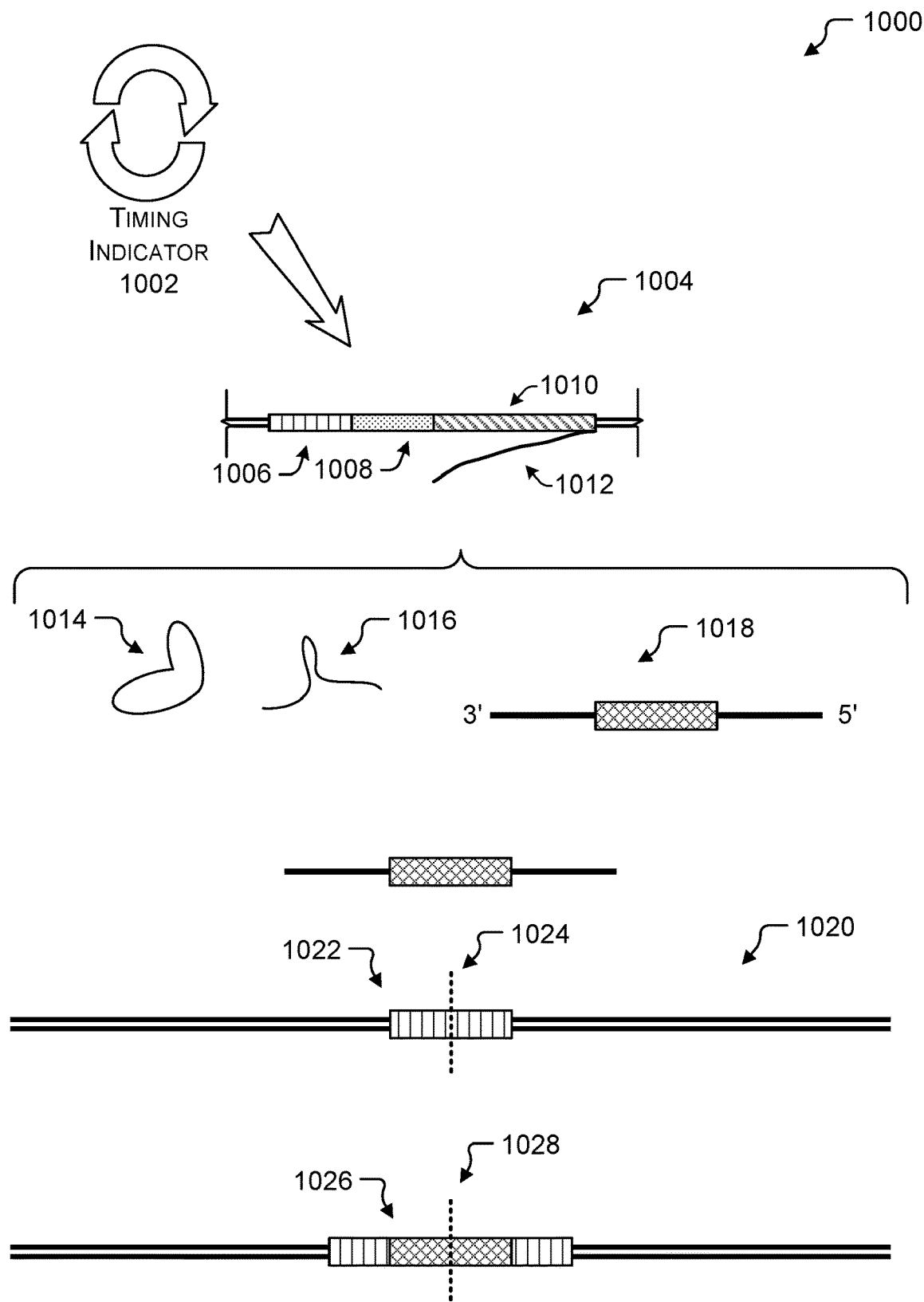
FIG. 10 shows incorporation of an HDR template into a double-stranded polynucleotide in response to a timing indicator.

FIG. 10 shows a diagram 1000 of a timing indicator 1002 controlling behavior of an operon 1004. The timing indicator 1002 may be based on a manually pulsed signal as described in conjunction with FIG. 8 or based on a natural biological cycle or a synthetic genetic circuit as described conjunction with FIG. 9. The operon 1004 can include a promoter 1006, an operator 1008, and a gene 1010. The gene encodes RNA 1012, the expression of which is up regulated at a frequency influenced by the timing indicator 1002.

The RNA 1012 may be translated into an enzyme 1014 that functions as a site-specific nuclease which creates DSBs at specific locations in double-stranded polynucleotides. Alternatively, the RNA 1012 may be gRNA 1016 that guides a Cas9 nuclease to a specific target site. Additionally, the RNA 1012 may be an HDR template 1018 or may be transcribed into ssDNA that functions as the HDR template 1018. Thus, through any of the mechanisms described above up regulation of the gene 1010 leads to increased integration of HDR templates into a specific target site on a double-stranded polynucleotide. This increase is affected either by increasing the enzymes that create the DSBs which are repaired through homology directed repair, guiding existing enzymes to specific locations in order to create the DSBs, or increasing copies of the HDR templates themselves.

A double-stranded polynucleotide 1020, which may be any of the double-stranded polynucleotides discussed elsewhere in this disclosure, includes a target site 1022 with a cut site 1024. Homology between the ends of the HDR template 1018 and the target site 1022 enable homology directed repair of a DSB created at the cut site 1024 as shown in FIGS. 1 and 2. This results in integration of a middle portion 1026 of the HDR template 1018 into the target site 1022 of the double-stranded polynucleotide 1020. Presence of the nucleotide sequence corresponding to this middle portion 1026 provides a genetic record of the timing indicator 1002. The middle portion 1026 of the HDR template 1018 can include a further cut site 1028. A DSB may be formed in this cut site 1028 by a different enzyme and the DSB may be repaired by a different HDR template. Thus, each cycle of the timing indicator 1002 creates an opportunity for integration of an HDR template configured for insertion into the middle portion 1026 of the HDR template 1018. Alternatively, the HDR template 1018 may be configured for insertion into the cut site 1028 included in its own middle portion 1026. This will lead to iterative insertion of the HDR template 1018 with each cycle of the timing indicator 1002. This configuration of a cell can create a record of time by recording the number of timing indicators 1002 that occurred. For example, five insertions of the HDR template 1018 indicates that five cycles of the timing indicator 1002 have elapsed. Alternatively, HDR templates corresponding to molecular events may also be integrated into the double-stranded polynucleotide 1020 and the presence of the HDR template 1018 corresponding to the timing indicator 1002 may provide an indication of the frequency and temporal spacing of the molecular events.

Figure 11:
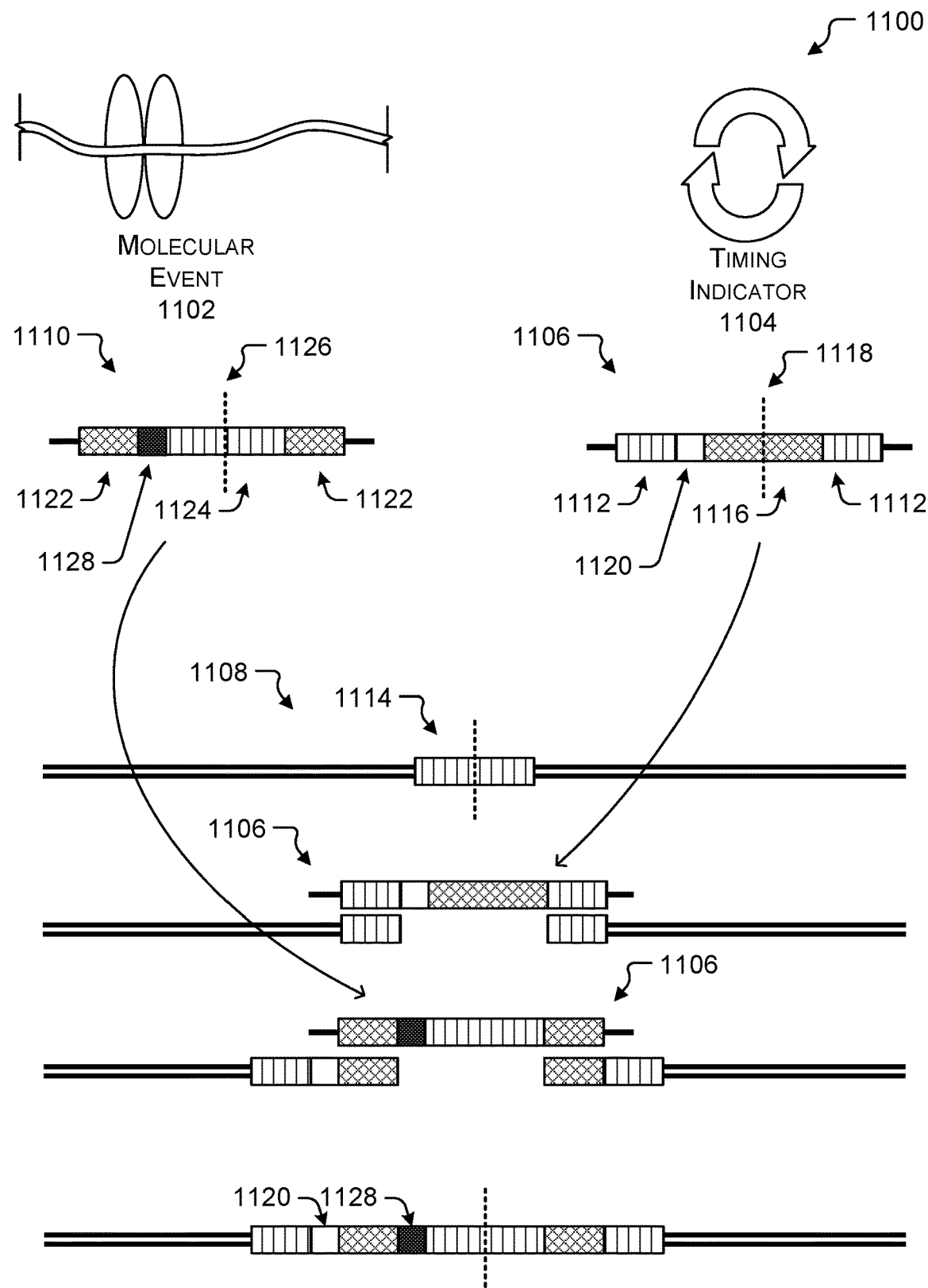
FIG. 11 shows insertion of an HDR template due to a molecular event into a region of a double-stranded polynucleotide integrated into the DNA of a cell in response to a timing indicator.

FIG. 11 shows a diagram 1100 illustrating insertion of an HDR template caused by molecular event 1102 following insertion of an HDR template in response to a timing indicator 1104. In this example, integration of a first HDR template 1106 caused by the timing indicator 1104 creates a location in the double-stranded polynucleotide 1108 for insertion of a second HDR template 1110 caused by the molecular event 1102. The molecular event 1102 may be the same or similar to any of the types of molecular events described previously in this disclosure. The timing indicator 1104 may be the same or similar to any of the other timing indicators described in this disclosure.

The timing indicator 1104 leads to creation of the first HDR template 1106 or to creation of enzymes that facilitate integration of the first HDR template 1106 into the double-stranded polynucleotide 1108. The first HDR template 1106 includes homology regions 1112 that are homologous to a target site 1114 on the double-stranded polynucleotide 1108. Thus, when a DSB is formed in the target site 1114, the first HDR template 1106 is able to repair the DSB through homology directed repair. This repair introduces the sequence in the middle of the first HDR template 1106 into the sequence of the double-stranded polynucleotide 1108. The first HDR template 1106 includes a middle section 1116 that can form homologies with portions of the second HDR template 1110. This middle section 1116 of the first HDR template 1106 may also include a cut site 1118 configured to be cut by a nuclease. The first HDR template 1106 includes an identifier region 1120 that is not homologous to the target site 1114 or to any portion of the first HDR template 1106. This identifier region 1120 may also be unique in that this sequence is not the same as any portion of the double-stranded polynucleotide 1108 or any portion of the first HDR template 1106. Thus, incorporation of the identifier region 1120 in the double-stranded polynucleotide 1108 provides an indication of an occurrence of the timing indicator 1104 that can be uniquely identified and that will be retained even following further iterative insertions at the cut site 1118 introduced by the first HDR template 1106.

The molecular event 1102 leads to creation of the second HDR template 1110 or to changes (e.g., increase in number or activity of nucleases) that increase the ability of already existing HDR templates 1110 to be incorporated into the double-stranded polynucleotide 1108. The second HDR template 1110 includes homology regions 1122 that are homologous to the middle portion 1116 of the first HDR template 1106. This allows insertion of the first HDR template 1106 to provide a location for subsequent insertion of the second HDR template 1110. Insertion of the second HDR template 1110 introduces into the double-stranded polynucleotide 1108 the portions of the second HDR template 1110 that are flanked by the homologous regions 1122. This includes a middle portion 1124 that may be homologous to the homologous portions 1112 of the first HDR template 1106. The middle portion 1124 can also include a cut site 1126. This cut site 1126 may be the same as the cut site present in the target site 1114 of the double-stranded polynucleotide 1108. Thus, the second HDR template 1110 may include a portion that introduces the same target site 1114 originally present in the double-stranded polynucleotide 1108. This makes it so that after integration of the second HDR template 1110, the double-stranded polynucleotide 1108 is once again capable of incorporating the first HDR template 1106 the next time a timing indicator 1104 occurs. Furthermore, the second HDR template 1110 may include its own identifier region 1128. Similar to the identifier region 1120 in the first HDR template 1106, this identifier region 1128 may be both unique and lacking homologies in either the second HDR template 1106 or the double-stranded polynucleotide 1108. Thus, each instance of the identifier region 1128 in the double-stranded polynucleotide 1108 provides a record showing that the molecular event 1102 occurred.

Because the first HDR template 1106 introduces a target site 1116 that is capable of incorporating the second HDR template 1110 and the second HDR template 1110 introduces a target site 1124 which is capable of incorporating the first HDR template 1106, this leads to alternative integration of the two HDR templates 1106, 1110. In this implementation, each time the timing indicator 1104 occurs, the molecular event 1102 may be logged. For example, if the timing indicator 1104 occurs with the frequency of about 24 hours, and the molecular event 1102 is temperature, then the temperature sensed by the cell may be recorded every 24 hours. Different temperatures may be recorded by having multiple different HDR templates that each respond to engineered signaling pathways triggered by different temperature ranges. Each of these various HDR templates may include the same homologous portions 1102 and same middle portion 1124 so that the ability to have alternative integration with the first HDR template 1106 is not altered. However, the identifier region 1128 may be different for each temperature range in order to create a nucleotide log that records changes in temperature.

Figure 12:
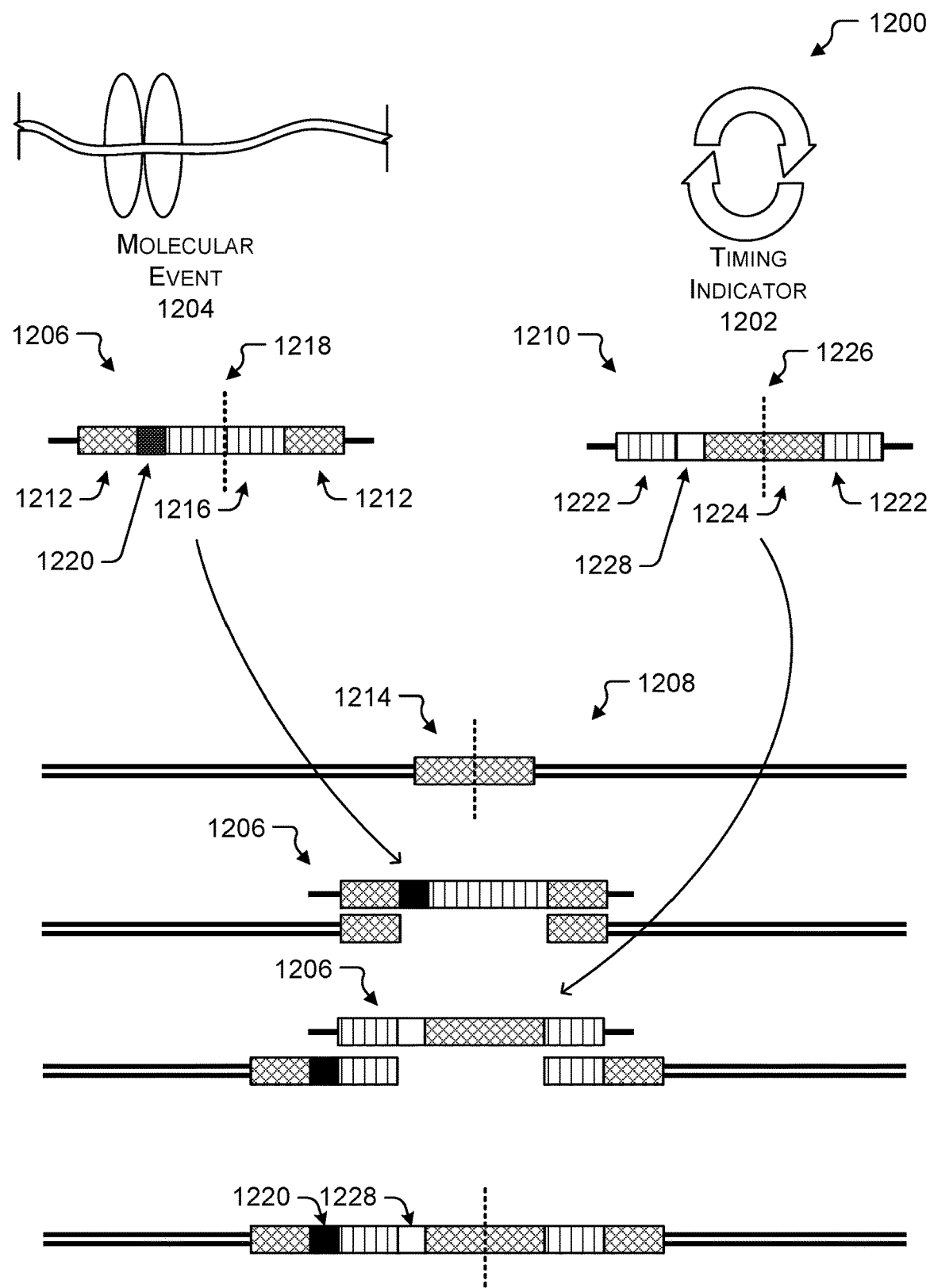
FIG. 12 shows insertion of an HDR template in response to a timing indicator integrated into a region of a double-stranded polynucleotide added to a cell due to a molecular event.

FIG. 12 shows a diagram 1200 illustrating insertion of an HDR template caused by a timing indicator 1202 following insertion of an HDR template in response to a molecular event 1204. In this example, integration of a first HDR template 1206 caused by the molecular event 1204 creates a location in the double-stranded polynucleotide 1208 for insertion of a second HDR template 1210 caused by the timing indicator 1202. Diagram 1200 in FIG. 12 is similar to diagram 1100 in FIG. 11 but shows a different sequence of the HDR template integration. Here, integration of the first HDR template 1206 in response to the molecular event 1204 occurs first and creates a target site for insertion of the second HDR template 1210 triggered by the timing indicator 1202.

The first HDR template 1206 includes homologous regions 1212 that form homologies with a target site 1214 on the double-stranded polynucleotide 1208. Like the HDR templates described in FIG. 11, the first HDR template 1206 also includes a middle region 1216, a cut site 1218, and an identifier region 1220. Integration of the first HDR template 1206 into the double-stranded polynucleotide 1208 creates a target site into which the second HDR template 1210 may be inserted based on the occurrence of the timing indicator 1202.

The second HDR template 1210 also includes homologous regions 1222, a middle region 1224, a cut site 1226, and an identifier region 1228. The homologous regions 1222 are homologous to the middle region 1216 of the first HDR template 1206. And, the middle region 1224 of the second HDR template introduces a target site into the double-stranded polynucleotide 1208 for insertion of the first HDR template 1206 if made available due to a molecular event 1204. Thus, in this implementation each time an event is sensed and this corresponding HDR template 1206 is integrated into the double-stranded polynucleotide 1208, it is possible to make a log of the time as represented by the timing indicator 1202 with the identification region 1228 included in the second HDR template 1210. This identification region 1228 may be slightly different in different versions of the second HDR template 1204 based on triggering by timing indicators 1202 that occur at different times. Thus, the specific sequence of the identification region 1228 varies based on which version of the second HDR template 1210 is abundant and that varies based on time. Thus, after recording of each molecular event 1204 it is possible to record a time which will be approximately the time that the molecular event occurred.

Figure 13:
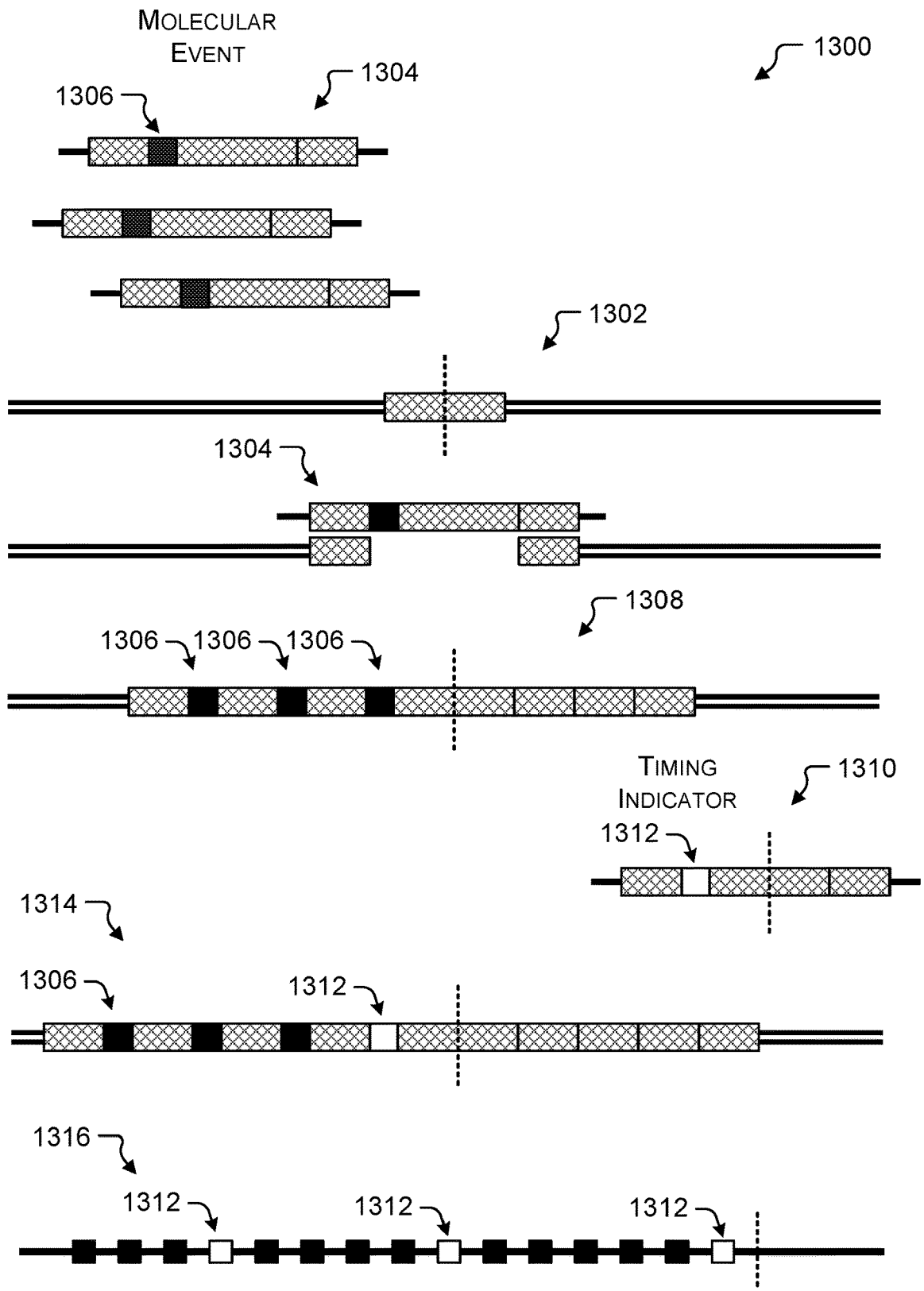
FIG. 13 shows an HDR template corresponding to a timing indicator added into a double-stranded polynucleotide that is continuously logging a molecular event.

FIG. 13 shows a diagram 1300 of integration of polynucleotide sequences representing timing indicators in a double-stranded polynucleotide 1302 that is continuously logging a molecular event. FIG. 11 and FIG. 12 show two different implementations in which alternating copies of HDR templates caused by molecular events and caused by timing indicators may be incorporated into a double-stranded polynucleotide. The diagram 1300 illustrates a similar architecture but shows how sequential and iterative logging of molecular events can be combined with logging of time points. In one implementation, a cell may be continuously logging a molecular event such as temperature, pH, presence of a chemical, salinity, etc. through techniques discussed earlier in this disclosure. Later evaluation of such a log may provide a record of how the environmental conditions of the cell changed and the order in which different conditions were experienced, but will not provide a ready way to correlate that with the times at which such conditions were experienced by the cell.

Occurrence of the molecular event may trigger creation and or introduction of a first HDR template 1304 into a double-stranded polynucleotide 1302. Multiple copies of the first HDR template 1304 may be created each time the event is sensed or the amount of copies may be proportional to the strength of the signal corresponding to the event. The double-stranded polynucleotide 1302 may include a target site in a cut site as described earlier. The first HDR template 1304 triggered in response to the molecular event can include an identifier region 1306. The first HDR template 1304 may be structured so that integration of one copy of the HDR template as a target site for subsequent, iterative insertion of the HDR template 1304.

The double-stranded polynucleotide following integration of multiple copies of the first HDR template 1304 is represented as a schematic 1308. This schematic 1308 shows how the nucleotide sequence of the double-stranded polynucleotide includes multiple copies of the identifier region 1306. This iterative insertion of the first HDR template 1304 may continue so long as the signal caused by the molecular event is present.

A timing indicator operating on a periodic or non-periodic but known frequency can cause a second HDR template 1310 to be present and/or available for integration into the double-stranded polynucleotide at a frequency corresponding to the timing indicator. This second HDR template 1310 can include an identifier region 1312 that is different from the identifier region 1306 present in the first HDR template 1304 associated with the molecular event. The second HDR template 1310 may have the same 3'-end, 5'-end, and middle portions as the first HDR template 1304. This allows the second HDR template 1310 to be integrated into a portion of the double-stranded polynucleotide 1302 created by repair of a DSB with the first HDR template 1304.

Schematic 1314 shows a structure of the double-stranded polynucleotide after the first HDR template 1304 has been inserted three times and the second HDR template 1310 has been inserted once. Schematic 1316 shows a structure of the double-stranded polynucleotide in somewhat simplified form after three cycles of the timing indicator have resulted in incorporation of the second HDR template 1310 three different times. Temporal patterns of the logging of the molecular event become evident when the identifier region 1312 of the second HDR template 1310 is present in the double-stranded polynucleotide. In this example, the schematic 1316 shows an increasing frequency of integration of the first HDR template 1304. Prior to the first instance of the identifier region 1312 caused by the timing indicator, three copies of the first HDR template 1304 are added. After the first identifier region 1312, four copies of the first HDR template 1304 are added before the next timing indicator occurs. Following the second incorporation of the identifier region 1312 and prior to the third, five copies of the first HDR template 1304 are added to the double-stranded polynucleotide. If the timing indicator occurs on a periodic schedule, then the frequency of the molecular event is increasing over time or, depending on the relationship between the engineered signaling pathway and the first HDR template 1304, the strength of the signal for the molecular event may be increasing over time.

One having ordinary skill in the art will appreciate that variations on this pattern can indicate different temporal relationships between behavior of the molecular event and the timing indicator. Thus, by creating a system in which both HDR templates corresponding to the sensed event and HDR templates corresponding to the timing indicator can be integrated into the same double-stranded polynucleotide, increased information about the timing of the molecular event is available from the double-stranded polynucleotide.

Illustrative System and Computing Devices

Figure 14:
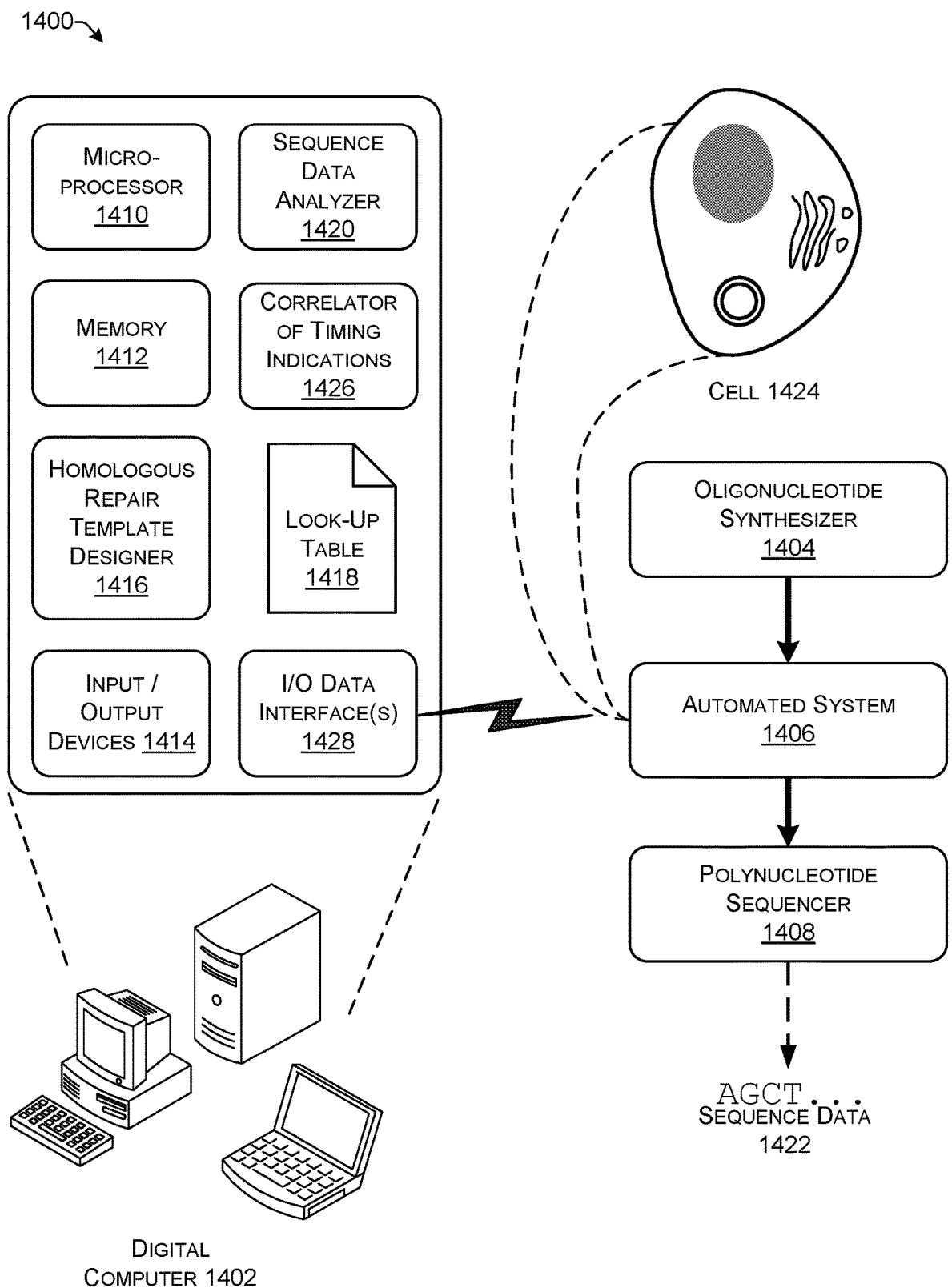
FIG. 14 shows an illustrative system for implementing the techniques described in this disclosure.

FIG. 14 shows an illustrative architecture 1400 for implementing and interacting with DNA molecules recording logs and timing of molecular events by use of HDR and timing indicators as described above. The architecture may include any of a digital computer 1402, an oligonucleotide synthesizer 1404, an automated system 1406, and/or a polynucleotide sequencer 1408. The architecture 1400 may also include other components besides those discussed herein.

As used herein, "digital computer" means a computing device including at least one hardware microprocessor 1410 and memory 1412 capable of storing information in a binary format. The digital computer 1402 may be a supercomputer, a server, a desktop computer, a notebook computer, a tablet computer, a game console, a mobile computer, a smartphone, or the like. The hardware microprocessor 1410 may be implemented in any suitable type of processor such as a single core processor, a multicore processor, a central processing unit (CPU), a graphical processing unit (GPU), or the like. The memory 1412 may include removable storage, non-removable storage, local storage, and/or remote storage to provide storage of computer readable instructions, data structures, program modules, and other data. The memory 1412 may be implemented as computer-readable media Computer-readable media includes, at least, two types of media, namely computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer readable instructions, data structures, program modules, or other data in a modulated data signal, such as a carrier wave, or other transmission mechanism. As defined herein, computer-readable storage media and communications media are mutually exclusive.

The digital computer 1402 may also include one or more input/output devices(s) 1414 such as a keyboard, a pointing device, a touchscreen, a microphone, a camera, a display, a speaker, a printer, and the like.

An HDR template designer 1416 may be included as part of the digital computer 1402, for example, as instructions stored in the memory 1412. The HDR template designer 1416 may design HDR templates based on sequences of target sites, sequences of dsDNA molecules, enzyme recognition sites, etc. In one implementation, the HDR template designer 1416 may design HDR templates to avoid cross talk between different signal recording pathways. The HDR template designer 1416 may also compare percent similarity and hybridization conditions for potential HDR templates as well as portions of the HDR templates. For example, the HDR template designer 1416 may design HDR templates to avoid the formation of hairpins as well as to prevent or minimize annealing between HDR templates. The HDR template designer 1416 may also design HDR templates to maximize a difference between the 3'-end sequence, 5'-end sequence, and/or middle sequence. For example, the difference may be G:C content and the HDR template designer 1416 may design sequences with a preference for increasing the G:C content difference between the end sequences and the middle sequence.

The digital computer 1402 may also include a look-up table 1418. However, the look-up table 1418 may be part of a hardware device that is physically separate from the digital computer 1402. The look-up table 1418 includes the correspondence between the sequence of an HDR template and a signal or a time point. For example, the information that expression of a given HDR template is up regulated in the presence of a given signal is one example of a correspondence that may be stored in the look-up table 1418. Users may make entries into the look-up table 1418 that indicate the times a given timing indicator was manually pulsed. The look-up table 1418 may store any number of different associations between signals/timing indicators and HDR templates. The look-up table 1418 may be pre-calculated and stored in static program storage, calculated (or "prefetched") as part of a program's initialization phase (e.g., memorization), or even stored in hardware in an application-specific platform.

A sequence data analyzer 1420 may analyze sequence data 1422 generated by the polynucleotide sequencer 1408. The sequence data analyzer 1420 may be implemented as instructions stored in the memory 1412. Thus, sequence data 1422 may be provided to the sequence data analyzer 1420 which analyzes the sequence data 1422 at least in part by comparison to nucleotide sequences contained in the look-up table 1418. The sequence data analyzer 1420 may identify which signals were detected by a cell 1424 and may identify timing indicators included in the DNA of the cell 1424. Depending on the design of the cell 1424, the sequence data analyzer 1420 may also identify a signal strength, relative signal strength, order of different signals, signal duration, timing of signals, or other characteristic of one or more signals represented in the sequence data 1422. As used herein, "cell" includes biological cells, minimal cells, artificial cells, and synthetic cells. A detectable molecular event is recognized by the cell, and the cell responds by modifying its genetic material.

Information about timing indicators and nucleotide sequences may be correlated with "wall-clock" time or the timing of a clock in the digital computer 1402 by a correlator of timing indications 1426. This correlator of timing indications 1426 may reference information from the look-up table 1418. For example, the sequence data 1422 may be searched to identify a polynucleotide sequence identified in the look-up table 1418 as corresponding to a genetic oscillator that has periodicity of 2.5 to 2.7 hours. Then, the correlator of time indications 1426 can use a known start time to derive a range of wall-clock times for various insertions of HDR templates generated by the timing of the genetic oscillator. Because the periodicity of the genetic oscillator is approximate, the range of possible values for wall-clock time will increase as the number of timing cycles increases. The correlator of timing indications 1426 can account for this range of possible times and provide estimated wall-clock times or a range of possible wall-clock times for various molecular events logged by the cell 1424.

In order to manipulate the DNA and potentially RNA that makes up the HDR templates and dsDNA, the digital computer 1402 may communicate with other devices through one or more I/O data interfaces 1428. The I/O data interface(s) 1428 can exchange instructions and data with other devices such as the oligonucleotide synthesizer 1404, the automated system 1406, and the polynucleotide sequencer 1408.

The oligonucleotide synthesizer 1404 chemically synthesizes oligonucleotides based on instructions received as electronic data. The synthesized oligonucleotides may be used as HDR templates, as dsDNA molecules that provide target sites, as plasmids, vectors, or other components. Thus, in some implementations, the sequence of nucleotides which is provided to the oligonucleotide synthesizer 1404 may come from the HDR template designer 1416.

A number of methods for DNA synthesis and commercial oligonucleotide synthesizers are available. Methods for DNA synthesis include solid-phase phosphoramidite synthesis, microchip-based oligonucleotide synthesis, ligation-mediated assembly, polymerases chain reaction PCR-mediated assembly, and the like. For example, such synthesis can be performed using an ABI 394 DNA Synthesizer (Applied Biosystems, Foster City, Calif.). One having ordinary skill in the art will understand how to use an oligonucleotide synthesizer to generate an oligonucleotide with a desired sequence.

The term "oligonucleotide" as used herein is defined as a molecule including two or more nucleotides. Oligonucleotides include probes and primers. Oligonucleotides used as probes or primers may also include nucleotide analogues such as phosphorothioates, alkylphosphorothioates, peptide nucleic acids, or intercalating agents. The introduction of these modifications may be advantageous in order to positively influence characteristics such as hybridization kinetics, reversibility of the hybrid-formation, stability of the oligonucleotide molecules, and the like.

The automated system 1406 may include any type of robotics, automation, or other system for automating one or more manipulations that may be performed on the dsDNA with the enzymes and/or the HDR templates. The automated system 1406 may be used in conjunction with manual operations such that the totality of operations needed to be performed to practice the techniques of this disclosure are done so in a hybrid manner in which some are performed by the automated system 1406 and others manually.

In one implementation, the automated system 1406 may include a microfluidics system. An illustrative microfluidics system may be configured to move small volumes of liquid according to techniques well-understood by those of ordinary skill in the art. As used herein, the automated system 1406 may include other equipment for manipulating DNA beyond that expressly shown in FIG. 14 such as, for example, a thermocycler.

The automated system 1406 may include a cell-free system that can be implemented in part by microfluidics. The cell-free system may also be implemented as an artificial cell or a minimal cell. As used herein the term "cell" encompasses natural cells, artificial cells, and minimal cells unless context clearly indicates otherwise. The automated system 1406 may include one or more natural cells such as a cell in culture. A culture of cells in the automated system 1406 may be manipulated by an automated cell culture system. An artificial cell or minimal cell is an engineered particle that mimics one or many functions of a biological cell. Artificial cells are biological or polymeric membranes which enclose biologically active materials. As such, nanoparticles, liposomes, polymersomes, microcapsules, detergent micelles, and a number of other particles may be considered artificial cells. Micro-encapsulation allows for metabolism within the membrane, exchange of small molecules and prevention of passage of large substances across it. Membranes for artificial cells can be made of simple polymers, crosslinked proteins, lipid membranes or polymer-lipid complexes. Further, membranes can be engineered to present surface proteins such as albumin, antigens, Na/K-ATPase carriers, or pores such as ion channels. Commonly used materials for the production of membranes include hydrogel polymers such as alginate, cellulose and thermoplastic polymers such as hydroxyethyl methacrylate-methyl methacrylate (HEMA-MMA), poly-acrylonitrile-polyvinyl chloride (PAN-PVC), as well as variations of the above-mentioned materials.

Minimal cells, also known as proto-cells, are cells that help all the minimum requirements for life. Minimal cells may be created by a top-down approach that knocks out genes in a single-celled organism until a minimal set of genes necessary for life are identified. *Mycoplasma mycoides, E. coli*, and *Saccharomyces cerevisiae*, are examples of organisms that may be modified to create minimal cells. One of ordinary skill in the art will recognize multiple techniques for generating minimal cells.

The cell-free system includes components for DNA replication and repair such as nucleotides, DNA polymerase, and DNA ligase. The cell-free system will also include dsDNA that includes at least one initial target site for creating a DSB. The dsDNA may be present in the vector that includes one or more operons. The cell-free system will also include buffers to maintain pH and ion availability. Furthermore, the cell-free system may also include the enzymes used for creating DSBs in dsDNA and the HDR templates used for repairing dsDNA. Some cell-free systems may include genes encoding the enzymes and HDR templates. To prevent enzymes from remaining when their respective cutting functions are no longer desired, the cell-free system may include proteolytic enzymes that specifically break down nucleases.

In a cell-free system, particular components may be added when needed either by moving volumes of liquid together with microfluidics or by increasing the expression of gene products that leads to synthesis of enzymes, HDR templates, etc.

The automated system 1406 may include a structure, such as at least one chamber, which holds one or more DNA molecules. The chamber may be implemented as any type of mechanical, biological, or chemical arrangement which holds a volume of liquid, including DNA, to a physical location. For example, a single flat surface having a droplet present thereon, with the droplet held by surface tension of the liquid, even though not fully enclosed within a container, is one implementation of a chamber.

The automated system 1406 may perform many types of manipulations on DNA molecules. For example, the automated system 1406 may be configured to move a volume of liquid from one chamber to another chamber in response to a series of instructions from the I/O data interface 1428.

The polynucleotide sequencer 1408 may sequence DNA molecules using any technique for sequencing polynucleotides known to those skilled in the art including classic dideoxy sequencing reactions (Sanger method), sequencing by synthesis using reversibly terminated labeled nucleotides, pyrosequencing, nanopore sequencing, SOLiD sequencing, chemical-sensitive field effect transistor (chemFET) sequencing, and ion semiconductor sequencing. The polynucleotide sequencer 1408 may be configured to sequence all or part of a dsDNA molecule modified according to any of the techniques described above and provide the sequence data 1422 to the digital computer 1402.

A cell 1424 may be prepared for sequencing by extracting nucleic acids according to standard methods in the art. For example, DNA from a cell can be isolated using various lytic enzymes, chemical solutions, or extracted by nucleic acid binding resins following instructions provided by a manufacturer. DNA contained in extracted sample may be detected by amplification procedures such as PCR or hybridization assays according to methods widely known in the art.

The sequence data 1422 generated by sequencing can be sent from the polynucleotide sequencer 1408 to the digital computer 1402 for analysis by the sequence data analyzer 1420, the correlator of timing indications 1426, and also for presentation on an output device 1414.

Illustrative Site-Specific Nucleases

Restriction enzymes (restriction endonucleases) are present in many species and are capable of sequence-specific binding to DNA (at a target or recognition site), and cleaving DNA at or near the site of binding. Over 3000 restriction enzymes have been studied in detail, and more than 600 of these are available commercially. Naturally occurring restriction endonucleases are categorized into four groups (Types I, II III, and IV) based on their composition and enzyme cofactor requirements, the nature of their target site, and the position of their DNA cleavage site relative to the target site. All types of enzymes recognize specific short DNA sequences and carry out the endonucleolytic cleavage of DNA to give specific fragments with terminal 5'-phosphates. One type of restriction enzyme, Type II enzymes, cleave within or at short specific distances from a recognition site; most require magnesium; single function (restriction) enzymes independent of methylase. Type II enzymes form homodimers, with recognition sites that are usually undivided and palindromic and 4-8 nucleotides in length. They recognize and cleave DNA at the same site, and they do not use ATP or AdoMet for their activity—they usually require only $Mg^{2+}$ as a cofactor. Common type II restriction enzymes include HhaI, HindIII, NotI, EcoRI, and BglI. Restriction enzymes may cut dsDNA in a way that leaves either blunt ends or sticky ends. Protocols for creating a DSB in dsDNA with restriction enzymes are well known to those skilled in the art. Restriction digest is a common molecular biology technique and is typically performed using the reagents and protocols provided in a commercially available restriction digest kit. Examples of companies that provide restriction digest kits include New England Bio- Labs, Promega, Sigma-Aldrich, and Thermo Fisher Scientific. Each of these companies provides restriction digest protocols on their website.

Homing endonucleases (HEs), which are also known as meganucleases, are a collection of double-stranded DNases that have large, asymmetric recognition sites (12-40 nt) and coding sequences that are usually embedded in either introns or inteins. Introns are spliced out of precursor RNAs, while inteins are spliced out of precursor proteins. They catalyze the hydrolysis of genomic DNA within the cells that synthesize them, but do so at few, or even a single, location(s) per genome. HE recognition sites are extremely rare. For example, an 18 nt recognition sequence will occur only once in every $7 \times 10^{10}$ nucleotides of random sequence. This is equivalent to only one site in 20 mammalian-sized genomes. However, unlike restriction endonucleases, HEs tolerate some sequence degeneracy within their recognition sequence. Thus, single base changes do not abolish cleavage but reduce its efficiency to variable extents. As a result, their observed sequence specificity is typically in the range of 10-12 nt. Examples of suitable protocols using HEs may be found in Flick, K. et al., *DNA Binding in Cleavage by the Nuclear Introns-Encoded Homing Endonuclease I-Ppol*, 394 Nature 96 (1998) and Chevalier, B. et al., *Design, Activity. and Structure of a Highly Specific Artificial Endonuclease*, 10 Molecular Cell 895 (2002).

Zinc finger nucleases (ZFNs) are synthetic proteins consisting of an engineered zinc finger DNA-binding domain fused to the cleavage domain of the FokI restriction endonuclease. ZFNs can be used to induce DSBs in specific DNA sequences and thereby promote site-specific homologous recombination and targeted manipulation of genomic loci in a variety of different cell types. The introduction of a DSB into dsDNA may enhance the efficiency of recombination with an exogenously introduced HDR template. ZFNs consist of a DNA-binding zinc finger domain (composed of three to six fingers) covalently linked to the non-specific DNA cleavage domain of the bacterial FokI restriction endonuclease. ZFNs can bind as dimers to their target DNA sites, with each monomer using its zinc finger domain to recognize a half-site. Dimerization of ZFNs is mediated by the FokI cleavage domain which cleaves within a five or six nucleotide "spacer" sequence that separates the two inverted "half sites." Because the DNA-binding specificities of zinc finger domains can in principle be re-engineered using one of various methods, customized ZFNs can be constructed to target nearly any DNA sequence. One of ordinary skill in the art will know how to design and use ZFNs to create DSBs in dsDNA at a desired target site. Some suitable protocols are available in Philipsbom, A. et al., *Microcontact printing of axon guidance molecules for generation of graded patterns*, 1 Nature Protocols 1322 (2006); John Young and Richard Harland, *Targeted Gene Disruption with Engineered Zinc Finger Nucleases (ZFNs)*, 917 Xenopus Protocols 129 (2012), and Hansen, K. et al. *Genome Editing with CompoZr Custom Zinc Finger Nucleases (ZFNs)*, 64 J. Vis. Exp. 3304 (2012).

TALENs are restriction enzymes that can be engineered to cut specific sequences of DNA. They are made by fusing a TAL effector DNA-binding domain to a DNA cleavage domain (i.e., a nuclease which cuts DNA strands). Transcription activator-like effectors (TALEs) can be engineered to bind practically any desired DNA sequence, so when combined with a nuclease, DNA can be cut at specific locations. The restriction enzymes can be introduced into cells, for use in gene editing or for genome editing in situ. The DNA binding domain contains a repeated highly conserved 33-34 amino acid sequence with divergent $12^{th}$ and $13^{th}$ amino acids. These two positions, referred to as the Repeat Variable Diresidue (RVD), are highly variable and show a strong correlation with specific nucleotide recognition. This straightforward relationship between amino acid sequence and DNA recognition has allowed for the engineering of specific DNA-binding domains by selecting a combination of repeat segments containing the appropriate RVDs. Notably, slight changes in the RVD and the incorporation of "nonconventional" RVD sequences can improve targeting specificity. One of ordinary skill in the art will know how to design and use TALENs to create DSBs in dsDNA at a desired target site. Some suitable protocols are available in Hermann. M. et al., *Mouse Genome Engineering Using Designer Nucleases*, 86 J. Vis. Exp. 50930 (2014) and Sakuma, T. et al., *Efficient TALEN Construction and Evaluation Methods for Human Cell and Animal Applications*, 18(4) Genes Cells 315 (2013).

In the CRISPR/Cas nuclease system, the CRISPR locus, encodes RNA components of the system, and the Cas (CRISPR-associated) locus, encodes proteins. CRISPR loci in microbial hosts contain a combination of CRISPR-associated (Cas) genes as well as non-coding RNA elements capable of programming the specificity of the CRISPR-mediated polynucleotide cleavage.

The Type II CRISPR is one of the most well characterized systems and carries out targeted double-stranded breaks in four sequential steps. First, two non-coding RNAs, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. In engineered CRISPR/Cas9 systems, gRNA also called single-guide RNA ("sgRNA") may replace crRNA and tracrRNA with a single RNA construct that includes the protospacer element and a linker loop sequence. Standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). In the context of this disclosure, a guanine (G) is considered complementary to a uracil (U), and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary. Use of gRNA may simplify the components needed to use CRISPR/Cas9 for genome editing. The Cas9 species of different organisms have different PAM sequences. For example, *Streptococcus pyogenes* (Sp) has a PAM sequence of 5'-NGG-3', *Staphylococcus aureus* (Sa) has a PAM sequence of 5'-NGRRT-3' or 5'-NGRRN-3', *Neisseria meningitidis* (NM) has a PAM sequence of 5'-NNNNGATT-3', *Streptococcus thermophilus* (St) has a PAM sequence of 5'-NNAGAAW-3', *Treponema denticola* (Td) has a PAM sequence of 5'-NAAAAC-3'.

Finally, Cas9 mediates cleavage of target DNA to create a DSB within the protospacer. Activity of the CRISPR/Cas system in nature comprises three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien polynucleotide. The alien polynucleotides come from viruses attaching the bacterial cell. Thus, in the bacterial cell, several of the so-called 'Cas' proteins are involved with the natural function of the CRISPR/Cas system and serve roles in functions such as insertion of the alien DNA, etc.

CRISPR may also function with nucleases other than Cas9. Two genes from the Cpf1 family contain a RuvC-like endonuclease domain, but they lack Cas9's second HNH endonuclease domain. Cpf1 cleaves DNA in a staggered pattern and requires only one RNA rather than the two (tracrRNA and crRNA) needed by Cas9 for cleavage. Cpf1's preferred PAM is 5'-TTN, differing from that of Cas9 (3'-NGG) in both genomic location and GC-content. Mature crRNAs for Cpf1-mediated cleavage are 42-44 nucleotides in length, about the same size as Cas9's, but with the direct repeat preceding the spacer rather than following it. The Cpf1 crRNA is also much simpler in structure than Cas9's; only a short stem-loop structure in the direct repeat region is necessary for cleavage of a target. Cpf1 also does not require an additional tracrRNA. Whereas Cas9 generates blunt ends 3 nt upstream of the PAM site, Cpf1 cleaves in a staggered fashion, creating a five nucleotide 5' overhang 18-23 nt away from the PAM.

Other CRISPR-associated proteins besides Cas9 may be used instead of Cas9. For example, CRISPR-associated protein 1 (Cas1) is one of the two universally conserved proteins found in the CRISPR prokaryotic immune defense system. Cas1 is a metal-dependent DNA-specific endonuclease that produces double-stranded DNA fragments. Cas1 forms a stable complex with the other universally conserved CRISPR-associated protein, Cas2, which is part of spacer acquisition for CRISPR systems.

There are also CRISPR/Cas9 variants that do not use a PAM sequence such as NgAgo. NgAgo functions with a 24-nucleotide ssDNA guide and is believed to cut 8-11 nucleotides from the start of this sequence. The ssDNA is loaded as the protein folds and cannot be swapped to a different guide unless the temperature is increased to non-physiological 55 C. A few nucleotides in the target DNA are removed near the cut site. Techniques for using NgAgo are described in Gao, F. et al., *DNA-guided Genome Editing Using the Natronobacterium Gregoryi Argonaute,* 34 Nature Biotechnology 768 (2016).

DSBs may be formed by making two single-stranded breaks at different locations creating a cut DNA molecule with sticky ends. Single-strand breaks or "nicks" may be formed by modified versions of the Cas9 enzyme containing only one active catalytic domain (called "Cas9 nickase"). Cas9 nickases still bind DNA based on gRNA specificity, but nickases are only capable of cutting one of the DNA strands. Two nickases targeting opposite strands are required to generate a DSB within the target DNA (often referred to as a "double nick" or "dual nickase" CRISPR system). This requirement dramatically increases target specificity, since it is unlikely that two off-target nicks will be generated within close enough proximity to cause a DSB. Techniques for using a dual nickase CRISPR system to create a DSB are described in Ran, et al., *Double Nicking by RNA-Guided CRISPR Cas9 for Enhanced Genome Editing Specificity,* 154 Cell 6:1380 (2013).

In certain embodiments, any of the enzymes described in this disclosure may be a "functional derivative" of a naturally occurring protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of an enzyme or a fragment thereof include but are not limited to mutants, fusions, covalent modifications of the protein or a fragment thereof. The enzyme, or a fragment thereof, as well as derivatives or a fragment thereof, may be obtainable from a cell or synthesized chemically or by a combination of these two procedures. The cell may be a cell that naturally produces the enzyme. A cell that naturally produces enzyme may also be genetically engineered to produce the endogenous enzyme at a higher expression level or to produce the enzyme from an exogenously introduced polynucleotide, which polynucleotide encodes an enzyme that is the same or different from the endogenous enzyme. In some cases, a cell does not naturally produce the enzyme and is genetically engineered to produce the enzyme. The engineering may include adding the polynucleotide encoding the enzyme under the control of a promoter. The promoter may be an inducible promoter that is activated in response to a signal. The promoter may also be blocked by a different signal or molecule.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document, "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A system for creating a temporal record in a polynucleotide log, the system comprising: a gene oscillator that creates a signal at a periodicity; a double-stranded polynucleotide having a target site; an enzyme configured to create a double strand break (DSB) in the double-stranded polynucleotide at a cut site in the target site; and a gene encoding a homology directed repair (HDR) template configured for insertion into the cut site, the HDR template including a middle portion that is not homologous to the target site, the gene expressing the HDR template based on presence of the signal relative to a threshold level, wherein the HDR template is incorporated into the double-stranded polynucleotide with a frequency that is based on the periodicity.

Clause 2. The system of clause 1, wherein the system comprises a single eukaryotic cell or a single prokaryotic cell.

Clause 3. The system of clause 1 or 2, wherein the enzyme comprises CRISPR/Cas and a gRNA having a protospacer element that hybridizes with one strand of the target site.

Clause 4. The system of any of clauses 1-3, wherein the middle portion comprises a second cut site and the system further comprises a second enzyme configured to create a DSB at the second cut site and a second gene encoding a second HDR configured for insertion into the second cut site, the second gene expressing the HDR template in response to a second signal generated by a molecular event.

Clause 5. The system of any of clauses 1-4, wherein the signal comprises a transcription factor that increases expression of the gene when the signal is above the threshold level.

Clause 6. The system of any of clauses 1-5, wherein the signal comprises a transcription factor that represses expression of the gene when the signal is above the threshold level.

Clause 7. The system of any of clauses 1-6, further comprising a vector containing the target site, a gene encoding the enzyme, and the gene encoding the HDR template.

Clause 8. A method comprising: exposing a cell to a timing indicator at a time, wherein the cell is configured to integrate a first homology directed repair (HDR) template into a double-stranded polynucleotide in response to exposing the cell to the timing indicator and to integrate a second HDR template into a repair formed by the first HDR template in the double-stranded polynucleotide in response to a molecular event; obtaining sequence data from the double-stranded polynucleotide after exposing the cell to the timing indicator and after the molecular event; and correlating the molecular event with the time based at least partly on analyzing the sequence data.

Clause 9. The method of clause 8, wherein the timing indicator comprises a change in light, a change in heat, a change in pH, availability of the first HDR template, or availability of an enzyme that creates a double strand break (DSB) in the double-stranded polynucleotide at a position configured for repair by the first HDR template.

Clause 10. The method of clause 8 or 9, wherein the molecular event is different than the timing indicator.

Clause 11. The method of any of clauses 8-10, further comprising exposing the cell to the timing indicator at a plurality of known times.

Clause 12. The method of any of clauses 8-11, wherein correlating the molecular event with the time includes identifying in the sequence data a sequence from the second HDR template adjacent to a first sequence from the first HDR template and adjacent to a second sequence from the first HDR template.

Clause 13. The method of any of clauses 8-12, wherein, in response to exposing the cell to the timing indicator, the cell is configured to upregulate expression of a gene encoding: the first HDR template, or at least a portion of an enzyme that creates a double strand break (DSB) in the double-stranded polynucleotide at a cut site that is configured to be repaired by the first HDR template.

Clause 14. The method of any of clauses 8-13, wherein the cell is further configured to iteratively integrate multiple copies of the second HDR template into the double-stranded polynucleotide while the molecular event continues.

Clause 15. A cellular system comprising: a molecule that degrades in the cellular system at a rate; a double-stranded polynucleotide; a first homology directed repair (HDR) template that is inserted into the double-stranded polynucleotide when the molecule is present in the cellular system at more than a threshold level; and a second HDR template that is inserted into the double-stranded polynucleotide when a signal caused by a molecular event is present.

Clause 16. The cellular system of clause 15, wherein the molecule comprises at least a portion of an enzyme configured to create a double strand break (DSB) in the double-stranded polynucleotide at a cut site flanked by regions homologous to the first HDR template.

Clause 17. The cellular system of clause 15 or 16, wherein the molecule comprises the first HDR template.

Clause 18. The cellular system of any of clauses 15-17, wherein the molecule comprises a transcription factor which increases transcription of a gene encoding the first HDR template or a gene encoding an enzyme configured to create a double strand break (DSB) in the double-stranded polynucleotide at a cut site flanked by regions homologous to the first HDR template.

Clause 19. The cellular system of any of clauses 15-18, wherein the molecule is ribonucleic acid (RNA) and the rate is determined in part by a 3'-poly(A) tail of the RNA.

Clause 20. The cellular system of any of clauses 15-19, wherein the second HDR template is inserted into a cut site introduced in the double-stranded polynucleotide by insertion of the first HDR template.

CONCLUSION

The terms "a," "an," "the" and similar referents used in the context of describing the invention (especially in the context of the following claims) are to be construed to cover both the singular and the plural, unless otherwise indicated herein or clearly contradicted by context. The term "based on" is to be construed to cover both exclusive and nonexclusive relationships. For example, "A is based on B" means that A is based at least in part on B and may be based wholly on B. By "about" is meant a quantity, level, value, number, frequency, percentage, dimension, size, amount, weight or length that varies by as much as 10, 9, 8, 7, 6, 5, 4, 3, 2 or 1% to a reference quantity, level, value, number, frequency, percentage, dimension, size, amount, weight or length.

All methods described herein can be performed in any suitable order unless otherwise indicated herein or otherwise clearly contradicted by context. The use of all examples and exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

Furthermore, references have been made to publications, patents and/or patent applications (collectively "references") throughout this specification. Each of the cited references is individually incorporated herein by reference for their particular cited teachings as well as for all that they disclose.

The invention claimed is:

1. A system for creating a temporal record in a polynucleotide log, the system comprising:
   a gene oscillator configured to create a signal at a periodicity;
   a double-stranded polynucleotide having a target site;
   an enzyme configured to create a double strand break (DSB) in the double-stranded polynucleotide at a cut site in the target site; and
   a gene encoding a homology directed repair (HDR) template configured for insertion into the cut site, the HDR template including a middle portion that is not homologous to the target site, the gene expressing the HDR template based on presence of the signal relative to a threshold level,
   wherein the HDR template is configured for incorporation into the double-stranded polynucleotide with a frequency that is based on the periodicity,
   wherein the middle portion comprises a second cut site and the system further comprises a second enzyme configured to create a DSB at the second cut site and a second gene encoding a second HDR configured for insertion into the second cut site, the second gene configured to express the HDR template in response to a second signal generated by a molecular event.

2. The system of claim 1, wherein the enzyme comprises CRISPR/Cas and a gRNA having a protospacer element that is configured to hybridize with one strand of the target site.

3. The system of claim 1, wherein the signal comprises a transcription factor.

4. The system of claim 1, further comprising a vector containing the target site, a gene encoding the enzyme, and the gene encoding the HDR template.

5. A method comprising:
   exposing a cell to a timing indicator at a time, wherein the cell is configured to perform homology directed repair (HDR) and wherein the timing indicator is a condition;
   responsive to exposure to the timing indicator, integrating by the cell through change of behavior of a gene regulatory element a first HDR template into a double-stranded polynucleotide in the cell, wherein integration of the first HDR template adds a target site to the double-stranded polynucleotide;
   waiting for occurrence of a molecular event wherein, responsive to occurrence of the molecular event, the cell integrates a second HDR template into the target site added by the first HDR template in the double-stranded polynucleotide, wherein the first HDR template and the second HDR template are both single-stranded polynucleotides;
   obtaining sequence data from the double-stranded polynucleotide after exposing the cell to the timing indicator and after the molecular event; and
   correlating the molecular event with the time based at least partly on analyzing the sequence data.

6. The method of claim 5, wherein the timing indicator comprises a chemical condition or an environmental condition external to the cell, and the chemical condition or the environmental condition comprises a change in light, a change in heat, or a change in pH.

7. The method of claim 5, wherein correlating the molecular event with the time includes identifying in the sequence data a sequence from the second HDR template adjacent to a first sequence from the first HDR template and adjacent to a second sequence from the first HDR template.

8. The method of claim 5, wherein, in response to the exposing the cell to the timing indicator, the cell upregulates expression of a gene encoding:
   the first HDR template; or
   at least a portion of an enzyme that creates a double strand break (DSB) in the double-stranded polynucleotide at a cut site which is configured to be repaired by the first HDR template.

9. The method of claim 5, wherein the cell iteratively integrates multiple copies of the second HDR template into the double-stranded polynucleotide during the occurrence of the molecular event.

10. The method of claim 5, wherein the condition that is the timing indicator comprises a chemical or environmental condition external to the cell; or a condition created by a synthetic genetic circuit in the cell.

11. The method of claim 5, wherein the timing indicator comprises a synthetic genetic circuit and wherein the synthetic genetic circuit comprises a switch, a bi-stable switch, a toggle switch, an oscillator, a repressilator, a counter, an anticipator, a learner, a kill switch, a quorum sensor (sender or receiver), a two-way signaling system, and-gates, nor-gates, nand-gate, inverters, or-gates, engineered ecosystem circuits, single invertase memory modules, analog-to-digital converters, or digital-to-analog converters.

12. The method of claim 5, wherein the HDR template has 3' and 5' ends that are complementary to the double-stranded polynucleotide in the cell and has a middle region that is not homologous to the double-stranded polynucleotide in the cell.

13. The method of claim 5, wherein the molecular event comprises: exposure to a chemical, a change in temperature, exposure to light, exposure to darkness, exposure to radiation, the presence of an antigen, or a change in ionic concentration.

14. The method of claim 5, wherein mechanisms for integrating the first HDR template and the second HDR template into the double-stranded polynucleotide are independently selected from the group of HDR mechanisms comprising homologous recombination, single-strand annealing, and breakage-induced replication.

15. A cellular system comprising:
   a molecule that degrades in the cellular system at a rate;
   a double-stranded polynucleotide;
   a first homology directed repair (HDR) template that is configured for insertion into the double-stranded polynucleotide when the molecule is present in the cellular system at more than a threshold level; and
   a second HDR template that is configured for insertion into the double-stranded polynucleotide when a signal caused by a molecular event is present, wherein the second HDR template is configured for insertion into a cut site introduced in the double-stranded polynucleotide by insertion of the first HDR template.

16. The cellular system of claim 15, wherein the molecule comprises one of:
   at least a portion of an enzyme configured to create a double strand break (DSB) in the double-stranded polynucleotide at a cut site flanked by regions homologous to the first HDR template; or
   the first HDR template.

17. The cellular system of claim 15, wherein the molecule comprises a transcription factor which increases transcription of a gene that encodes the first HDR template or a gene that encodes an enzyme configured to create a double strand break (DSB) in the double-stranded polynucleotide at a cut site flanked by regions homologous to the first HDR template.

18. The cellular system of claim 15, wherein the molecule is ribonucleic acid (RNA) and the rate is determined in part by a 3'-poly(A) tail of the RNA.

* * * * *

```
                        SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: X1 example

<400> SEQUENCE: 1
tagccgtatc gagcatcgat g                                             21

<210> SEQ ID NO 2
<211> LENGTH: 11
<212> TYPE: DNA
<213> ORGANISM: Artificial Sequence
<220> FEATURE:
<223> OTHER INFORMATION: X2 example
<220> FEATURE:
<221> NAME/KEY: misc_feature
<222> LOCATION: (4)..(7)
<223> OTHER INFORMATION: n is a, c, g, or t

<400> SEQUENCE: 2
cgcnnnngat t                                                        11

<210> SEQ ID NO 3
<211> LENGTH: 21
<212> TYPE: DNA
<213> ORGANISM: Artificial Sequence
<220> FEATURE:
<223> OTHER INFORMATION: Y1 example

<400> SEQUENCE: 3
gatcgatgga ctctgcatct a                                             21

<210> SEQ ID NO 4
<211> LENGTH: 11
<212> TYPE: DNA
<213> ORGANISM: Artificial Sequence
<220> FEATURE:
<223> OTHER INFORMATION: Y2 example
<220> FEATURE:
<221> NAME/KEY: misc_feature
<222> LOCATION: (4)..(7)
<223> OTHER INFORMATION: n is a, c, g, or t

<400> SEQUENCE: 4
tcgnnnngat t                                                        11

<210> SEQ ID NO 5
<211> LENGTH: 21
<212> TYPE: DNA
<213> ORGANISM: Artificial Sequence
<220> FEATURE:
<223> OTHER INFORMATION: Z1 example
```

```
<400> SEQUENCE: 5
cgggacgatc gatcgggcta g                                              21

<210> SEQ ID NO 6
<211> LENGTH: 11
<212> TYPE: DNA
<213> ORGANISM: Artificial Sequence
<220> FEATURE:
<223> OTHER INFORMATION: Z2 example
<220> FEATURE:
<221> NAME/KEY: misc_feature
<222> LOCATION: (4)..(7)
<223> OTHER INFORMATION: n is a, c, g, or t

<400> SEQUENCE: 6
actnnnngat t                                                         11

<210> SEQ ID NO 7
<211> LENGTH: 64
<212> TYPE: DNA
<213> ORGANISM: Artificial Sequence
<220> FEATURE:
<223> OTHER INFORMATION: Homology directed repair sequences of X1Y1Y2X2
<220> FEATURE:
<221> NAME/KEY: misc_feature
<222> LOCATION: (46)..(49)
<223> OTHER INFORMATION: n is a, c, g, or t
<220> FEATURE:
<221> NAME/KEY: misc_feature
<222> LOCATION: (57)..(60)
<223> OTHER INFORMATION: n is a, c, g, or t

<400> SEQUENCE: 7
tagccgtatc gagcatcgat ggatcgatgg actctgcatc tatcgnnnng attcgcnnnn    60
gatt                                                                 64

<210> SEQ ID NO 8
<211> LENGTH: 64
<212> TYPE: DNA
<213> ORGANISM: Artificial Sequence
<220> FEATURE:
<223> OTHER INFORMATION: Homology directed repair sequences Y1X1X2Y2
<220> FEATURE:
<221> NAME/KEY: misc_feature
<222> LOCATION: (46)..(49)
<223> OTHER INFORMATION: n is a, c, g, or t
<220> FEATURE:
<221> NAME/KEY: misc_feature
<222> LOCATION: (57)..(60)
<223> OTHER INFORMATION: n is a, c, g, or t

<400> SEQUENCE: 8
gatcgatgga ctctgcatct atagccgtat cgagcatcga tgcgcnnnng atttcgnnnn    60
gatt                                                                 64

<210> SEQ ID NO 9
<211> LENGTH: 12
<212> TYPE: DNA
<213> ORGANISM: Artificial Sequence
<220> FEATURE:
<223> OTHER INFORMATION: Repeated subsequence in target sequence example

<400> SEQUENCE: 9
gtactagtac ta                                                        12
```